US008497135B2

(12) United States Patent
Klinefelter

(10) Patent No.: US 8,497,135 B2
(45) Date of Patent: Jul. 30, 2013

(54) DIAGNOSTIC KITS TO DETECT SP22 AND SP22 ANTIBODIES

(75) Inventor: Gary R. Klinefelter, Fuguay-Varina, NC (US)

(73) Assignee: U.S. Environmental Protection Agency, Research Triangle Park, NC (US)

( * ) Notice: Subject to any disclaimer, the term of this patent is extended or adjusted under 35 U.S.C. 154(b) by 308 days.

(21) Appl. No.: 12/279,135

(22) PCT Filed: Feb. 13, 2007

(86) PCT No.: PCT/US2007/062056
§ 371 (c)(1),
(2), (4) Date: Dec. 22, 2008

(87) PCT Pub. No.: WO2007/095530
PCT Pub. Date: Aug. 23, 2007

(65) Prior Publication Data
US 2009/0317828 A1    Dec. 24, 2009

Related U.S. Application Data

(60) Provisional application No. 60/772,737, filed on Feb. 13, 2006.

(51) Int. Cl.
*G01N 33/558* (2006.01)

(52) U.S. Cl.
USPC ........ 436/514; 422/420; 422/430; 435/283.1; 435/287.1; 435/287.7; 435/970; 436/518; 436/528; 436/164; 436/172; 436/808

(58) Field of Classification Search
USPC ............ 436/518, 808, 810; 435/283.1, 287.1, 435/287.7; 422/50, 420, 430
See application file for complete search history.

(56) References Cited

U.S. PATENT DOCUMENTS

| | | | |
|---|---|---|---|
| 3,854,470 A | 12/1974 | Augspurger | |
| 3,866,598 A | 2/1975 | Augspurger | |
| 4,326,505 A | 4/1982 | Cropsey | |
| 4,764,502 A | 8/1988 | diZerega | |
| 4,816,257 A | 3/1989 | Buster et al. | |
| 4,943,522 A | 7/1990 | Eisinger et al. | |
| 5,175,148 A | 12/1992 | O'Rand et al. | |
| 5,346,990 A | 9/1994 | Spaulding | |
| 5,569,581 A | 10/1996 | Killian et al. | |
| 5,602,005 A | 2/1997 | Herr et al. | |
| 5,677,133 A * | 10/1997 | Oberhardt | 435/7.1 |
| 5,725,481 A | 3/1998 | Buck et al. | |
| 6,197,940 B1 | 3/2001 | Klinefelter | |
| 6,258,364 B1 | 7/2001 | Herr et al. | |
| 6,355,235 B1 | 3/2002 | Cone et al. | |
| 6,391,654 B1 | 5/2002 | Bateman | |
| 6,403,092 B1 | 6/2002 | Pizzo et al. | |
| 6,472,226 B1 * | 10/2002 | Barradine et al. | 436/518 |
| 6,541,206 B1 * | 4/2003 | Huszar | 435/6.19 |
| 6,965,016 B2 | 11/2005 | Klinefelter | |
| 7,211,403 B2 * | 5/2007 | Barradine et al. | 435/7.21 |
| 2002/0052011 A1 | 5/2002 | Klinefelter | |

FOREIGN PATENT DOCUMENTS

| | | |
|---|---|---|
| EP | 0291194 B2 | 7/2003 |
| WO | WO-90/09802 A1 | 9/1990 |
| WO | WO-97/27218 | 7/1997 |
| WO | WO-99/54354 | 10/1999 |
| WO | WO 99/54354 A1 | 10/1999 |

OTHER PUBLICATIONS

Lavers, A.E. et al., "Localization of SP22 on Human Sperm of Differing Quality," J. of Andrology, p. 123, (2001); XP009114883.
Klinefelter, G.R. et al., "Localization of the Sperm Protein SP22 and Inhibition of Fertility in vivo and in vitro," J. of Andrology, 23(1):48-63 (2002); XP002992370.
Supplementary European Search Report for EP 07717612.1, mailed May 8, 2009.
International Search Report for PCT/US2007/062056, mailed Feb. 4, 2008.
Abbas, et al. "Cellular and Molecular Immunology, fourth edition" W.B. Saunders Company, 56-58 (2000).
Abdel-Hamid, I., et al.; "Development of a flow-through immunoassay system," Sensors and Actuators B: Chemical 49(3):202-210 (Jul. 1, 1998).
Ahmad, et al., "Thymosin alpha-1 and FA-1 monoclonal antibody affect fertilizing capacity of human sperm by modulating protein phosphorylation pattern." J of Reproductive Immunology, vol. 29(1): 1-17 (1995).
American Heritage Dictinary definition of reducing downloaded Aug. 29, 2006 from dictionary.reference.com, 2 pages.
Brooks, D.E., "Characterization of a 22 kDa Protein with Widespread Tissue Distribution but Which is Uniquely Present in Secretions of the Test is and Epididymis and on the Surface of Spermtozoa," Biochimia et Biophyica Acta 841:59-70 (1985).
Colman, P.M., "Effects of amino acid sequence changes on antibody-antigen interactions," Research in Immunology 145:33-36 (1994).
Gilbert, S.F. Developmental Biology, 4th edition, Sinauer Associates, Inc., pp. 4-5 (1994).
Kaydos et al., "Haloacid Induced Alterations in Fertility and the Sperm Biomarker SP22 in the Rat are Additive: Validation of an ELISA," Toxicological Sciences 81:430-442 (2004).
Klinefelter et al., "Bromochloroacetic Acid Exerts Qualitative Effects on Rat Sperm: Implications for a Novel Biomarker," Toxicological Sciences 68:164-173 (2002).
Klinefelter, G.R., et al., "Discriminant Analysis indicates a Single Sperm Protein (SP22) is Predictive of Fertility Following Exposure to Epididymal Toxicants," Journal of Andrology 18(2):139-150 (1997).
Klinefelter, G.R., "Saga of a Sperm Fertility Biomarker," Animal Reproduction Sciences, 105:90-103 (2008).
Linder et al., "Dibromoacetic Acid Affects Reproductive Competence and Sperm Quality in the Male Rat," Fundam Appl Toxicol., 28(1):9-17 (1995).
Linder et al., "Histopathologic changes in the testes of rats exposed to dibromoacetic acid," Reprod Toxicol., 11(1):47-56 (1997).
Linder et al., "Spermatotoxity of dichloroacetic acid," Reprod Toxicol., 11(5)681-8 (1997).
Merriam-Webster OnLine definition of fertle downloaded Aug. 29, 2006 from m-w.com, 3 pages.
Merriam-Webster OnLine definition of fertlity downloaded Aug. 29, 2006 from m-w.com, 2 pages.

(Continued)

*Primary Examiner* — Chris L Chin
(74) *Attorney, Agent, or Firm* — Foley Hoag LLP

(57) ABSTRACT

Oral, topical and injectable contraceptives, which are based on sperm protein 22 kDa (SP22) polypeptides and antibodies and infertility diagnostics and kits are provided.

12 Claims, 34 Drawing Sheets

OTHER PUBLICATIONS

Nagakubo et al., "DJ-1, a novel oncogene which transforms mouse NIH3T3 cells in cooperation with rats," Biochem & Biophys Res. Comm,. 231(2):509-513 (1997).

Naz, et al., "Monoclonal Antibody to a Human Germ Cell Membrane Glycoprotein That Inhibits Fertilization." Science, vol. 225(20): 342-344 (1984).

Okada, et al., "DJ-1, a Target Protein for an Endocrine Disrupter, Participates in the Fertilization in Mice." Biol Pharm. Bull., 25(7):853-856 (2002).

Primakoff, P., "Sperm proteins being studies for use in a contraceptive vaccine," American Journal of Reproductive Immunology, 31(4):208-210 (1994).

Wagenfeld, A., et al., "Molecular Cloning and Expression of Rat Contraception Associated Protein 1 (CAP1), a Protein Putatively Involved in Fertilization," Biochemical and Biophysical Research Communications 251:545-549 (1998).

Welch, J.E., et al., "SP22: A Novel Fertility Protein from a Highly Conserved Gene Family," Journal of Andrology 19(4):385-393 (1998).

Welsch, J.E., et al., "A 22 kDa Sperm Protein (SP22) Correlated with Rat Fertility Exhibits Homology with the J-1/thiJ Family of Proteins," Molecular Biology of the Cell 8:325a (1997).

Yee et al., Contraceptive Vaccines with Sperm Proteins, pp. 693-712, (1995).

EP Supplemental Search Report 07 71 7612 mailed May 8, 2009.

Examination Report for EP 07 717 612.1 dated Apr. 6, 2011.

Office Action for U.S. Appl. No. 11/572,453 dated Sep. 2, 2010.

Hoodbhoy, et al. "Insights into the molecular basis of sperm-egg recognition in mammals," Reproduction Review, 127: 417-422 (2004).

Examination Report for EP 07717612.1 dated Mar. 11, 2011.

Examination Report for EP 05775065.5 dated Dec. 19, 2011.

Final Office Action for U.S. Appl. No. 12/814,080 dated Oct. 10, 2011.

* cited by examiner

FIGURE 1A

```
1    xxxxxxxxxxxxxxxxxxxxxxxxxxxxxxxxxxxxxxxxxatggcatccaaaagagctctggtcatc  66
1    x  x  x  x  x  x  x  x  x  x  x  x  x  M  A  S  K  R  A  L  V  I    22
67   ctagccaaaggagcagaggagatggagacagtgattcctgtggacatcatgcggcgagctgggatt  132
23   L  A  K  G  A  E  E  M  E  T  V  I  P  V  D  I  M  R  R  A  G  I    44
133  aaagtcaccgttgcaggcttggctgggaaggaccccgtgcagtgtagccgtgatgtagtgatttgt  198
45   K  V  T  V  A  G  L  A  G  K  D  P  V  Q  C  S  R  D  V  V  I  C    66
199  ccggataccagtctggaagaagcaaaaacacaggaccatacgatgtggttgttcttccaggagga   264
67   P  D  T  S  L  E  E  A  K  T  Q  G  P  Y  D  V  V  V  L  P  G  G    88
265  aatctgggtgcacagaacttatctgagtcggctttggtgaaggagatcctcaaggagcaggagaac  330
89   N  L  G  A  Q  N  L  S  E  S  A  L  V  K  E  I  L  K  E  Q  E  N    110
331  aggaagggcctcatagctgccatctgtgcgggtcctacggcctgctggctcacgaagtaggcttt   396
111  R  K  G  L  I  A  A  I  C  A  G  P  T  A  L  L  A  H  E  V  G  F    132
397  ggatgcaaggttacatcgcacccattggctaaggacaaaatgatgaacggcagtcactacagctac  462
133  G  C  K  V  T  S  H  P  L  A  K  D  K  M  M  N  G  S  H  Y  S  Y    154
463  tcagagagccgtgtggagaaggacggcctcatcctcaccagccgtgggcctgggaccagcttcgag  528
155  S  E  S  R  V  E  K  D  G  L  I  L  T  S  R  G  P  G  T  S  F  E    176
528  tttgcgctggccattgtggaggcactcagtggcaaggacatggctaaccaagtgaaggccccgctt  594
177  F  A  L  A  I  V  E  A  L  S  G  K  D  M  A  N  Q  V  K  A  P  L    198
595  gttctcaaagactagagagccaagccctggaccctggaccccaggctgagcaggcattggaagc    660
199  V  L  K  D  *                                                       202
661  ccactagagagaccacagcccagtgaacctggcattggaagcccactagtgtgtccacagcccagt  726
727  gaacctcaggaactaacgtgtgaagtagcccgctgctcaggaatctcgccctggctctgtactatt  792
793  ctgagccttgctagtagaatanacagttccccaagctc                               830
```

FIGURE 1B

```
SP22    1   MASKRALVILAKGAEEMETVIPVDIMRRAGIKVTVAGLAGKDPVQCSRDV  50
            ||||||||||||||||||||||||||:|||||||||||||||||||||||
DJ-1    1   MASKRALVILAKGAEEMETVIPVDVMRRAGIKVTVAGLAGKDPVQCSRDV  50
                                                       Peptide 1

SP22    51  VICPDTSLEEAKTQGPYDVVVLPGGNLGAQNLSESALVKEILKEQENRKG  100
            |||||-|||:||  |||||||||||||||||||||||:||||||||||||
DJ-1    51  VICPDASLEDAKKEGPYDVVVLPGGNLGAQNLSESAAVKEILKEQENRKG  100
                                                       Peptide 2

SP22    101 LIAAICAGPTALLAHEVGFGCKVTSHPLAKDKMMNGSHYSYSESRVEKD   149
            |||||||||||||||:| |:|||:||||||||| ||:||| |||||
DJ-1    101 LIAAICAGPTALLAHEIGCGSKVTTHPLAKDKMMNGGHYTYSENRVEKD   149
                                                       Peptide 3

SP22    150 GLILTSRGPGTSFEFALAIVEALSGKDMANQVKAPLVLKD    189
            |||||||||||||||||||||||| ||:=| |||||||||
DJ-1    150 GLILTSRGPGTSFEFALAIVEALNGKEVAAQVKAPLVLKD    189
            Peptide 4
```

FIGURE 2

```
  1  A gctgtgcagagccgtctggcagggttgacctcctaaagggatattccatctttattaatcattag  65

66  A tagtgtggtcagagacttagcaccattggtctccccaacctggtccagacatttcagcagttta  130

131  A tcggaacagcaacaacagcaacaaaaccttcaaaatttacaagtctttaagaaatagaaATGgca  195
     B        tggcttcgcgtgggtggaggaggcgcggctgcaggtctttaagaaatagaaATGgca
  1                                                              M   A    2

196    tccaaaagagctctggtcatcctagccaaaggagcagaggagatggagacagtgattcctgtgga  260
  3      S   K   R   A   L   V   I   L   A   K   G   A   E   E   M   E   T   V   I   P   V   D  24

261    catcatgcggcgagctgggattaaagtcaccgttgcaggcttggctgggaaggacccgtgcagt  325
 25      I   M   R   R   A   G   I   K   V   T   V   A   G   L   A   G   K   D   P   V   Q   45
                                          Peptide 1

326    gtagccgtgatgtagtgatttgtccggataccagtctggaagaagcaaaaacacagggaccatac  390
 46      C   S   R   D   V   V   I   C   P   D   T   S   L   E   E   A   K   T   Q   G   P   Y  67

391    gatgtggttgttcttccaggaggaaatctgggtgcacagaacttatctgagtcggctttggtgaa  455
 68      D   V   V   V   L   P   G   G   N   L   G   A   Q   N   L   S   E   S   A   L   V   K  89

456    ggagatcctcaaggagcaggagaacaggaagggcctcatagctgccatctgtgcgggtcctacgg  520
 90      E   I   L   K   E   Q   E   N   R   K   G   L   I   A   A   I   C   A   G   P   T     110
             Peptide 2                                              *

521    ccctgctggctcacgaagtaggctttggatgcaaggttacatcgcacccattggctaaggacaaa  585
111      A   L   L   A   H   E   V   G   F   G   C   K   V   T   S   H   P   L   A   K   D   K 132
                                                    Peptide 3

586    atgatgaacggcagtcactacagctactcagagagccgtgtggagaaggacggcctcatcctcac  650
133      M   M   N   G   S   H   Y   S   Y   S   E   S   R   V   E   K   D   G   L   I   L   T 154
                                                                      Peptide 4

651    cagccgtgggcctgggaccagcttcgagtttgcgctggccattgtggaggcactcagtggcaagg  715
155      S   R   G   P   G   T   S   F   E   F   A   L   A   I   V   E   A   L   S   G   K     175

716    acatggctaaccaagtgaaggccccgcttgttctcaaagacTAGagagcccaagccctggaccct  780
176      D   M   A   N   Q   V   K   A   P   L   V   L   K   D   *                              189

781    ggaccccaggctgagcaggcattggaagcccactagtgtgtccacagcccagtgaacctggcat  845

846    tggaagcccactagtgtgtccacagcccagtgaacctcaggaactaacgtgtgaagtagcccgct  910

911    gctcaggaatctcgccctggctctgtactattctgagccttgctagtagaataaacagttcccca  975

976    agctc*c*tgacggct*                                                  985
```

FIGURE 4
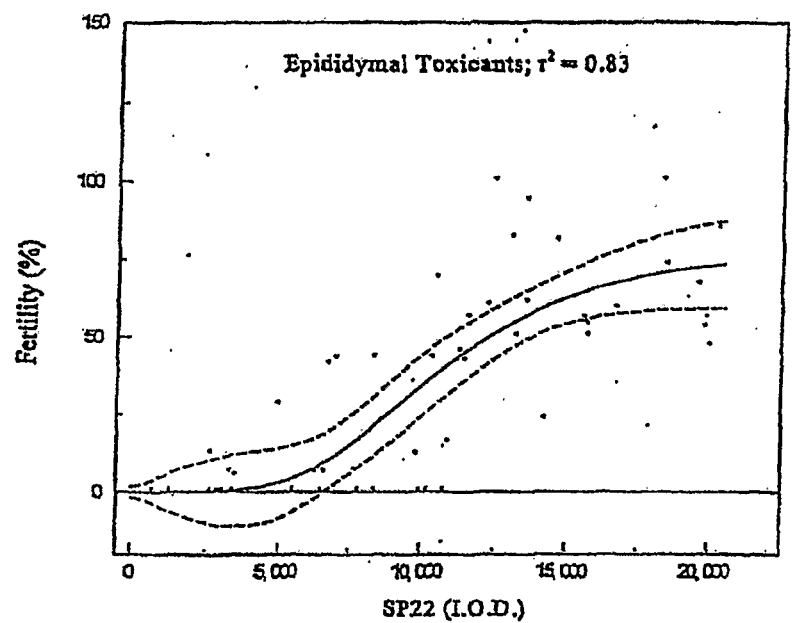
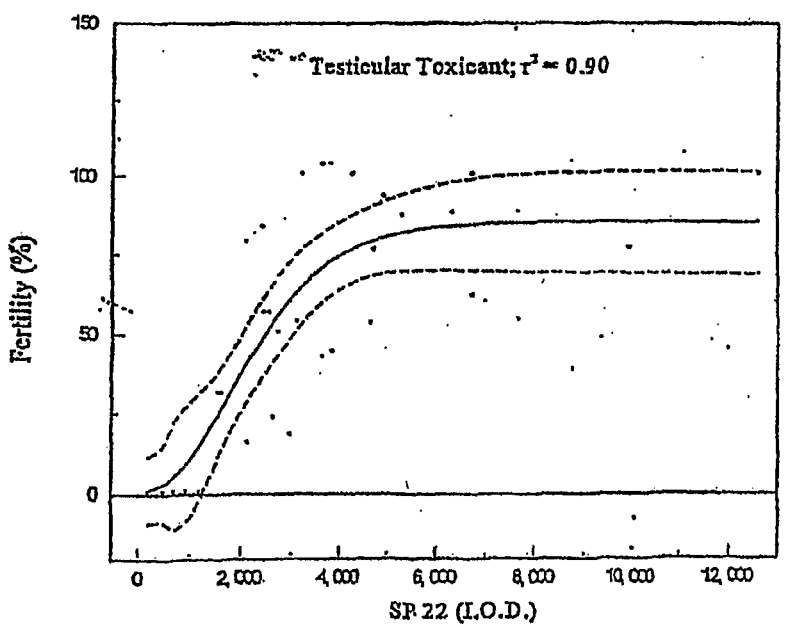

Figure 23
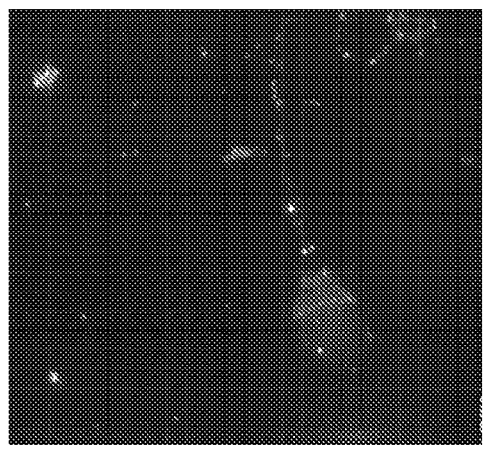
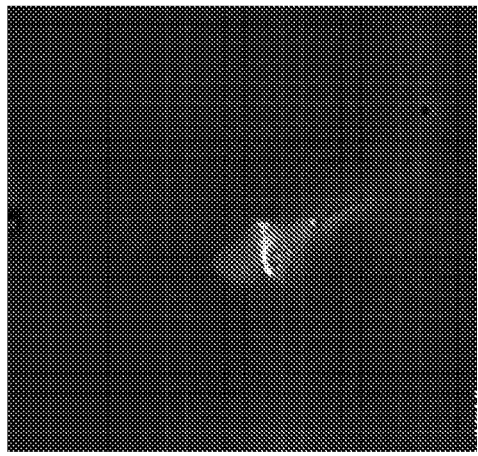
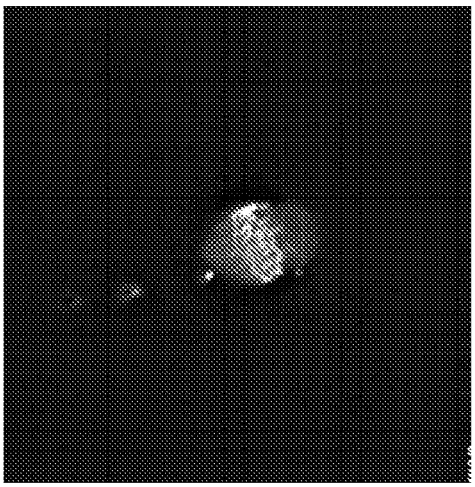

SEQUENCE LISTING

<160> NUMBER OF SEQ ID NOS: 76

<210> SEQ ID NO 1
<211> LENGTH: 791
<212> TYPE: DNA
<213> ORGANISM: Rattus norvegicus
<220> FEATURE:
<221> NAME/KEY: CDS
<222> LOCATION: (1)..(567)

```
<400> SEQUENCE: 1 atg gca tcc aaa aga gct ctg gtc atc cta gcc aaa gga gca gag gag      48
Met Ala Ser Lys Arg Ala Leu Val Ile Leu Ala Lys Gly Ala Glu Glu
1               5                   10                  15 atg gag aca gtg att cct gtg gac atc atg cgg cga gct ggg att aaa      96
Met Glu Thr Val Ile Pro Val Asp Ile Met Arg Arg Ala Gly Ile Lys
            20                  25                  30 gtc acc gtt gca ggc ttg gct ggg aag gac ccc gtg cag tgt agc cgt     144
Val Thr Val Ala Gly Leu Ala Gly Lys Asp Pro Val Gln Cys Ser Arg
        35                  40                  45 gat gta gtg att tgt ccg gat acc agt ctg gaa gaa gca aaa aca cag     192
Asp Val Val Ile Cys Pro Asp Thr Ser Leu Glu Glu Ala Lys Thr Gln
    50                  55                  60 gga cca tac gat gtg gtt gtt ctt cca gga gga aat ctg ggt gca cag     240
Gly Pro Tyr Asp Val Val Val Leu Pro Gly Gly Asn Leu Gly Ala Gln
65                  70                  75                  80 aac tta tct gag tcg gct ttg gtg aag gag atc ctc aag gag cag gag     288
Asn Leu Ser Glu Ser Ala Leu Val Lys Glu Ile Leu Lys Glu Gln Glu
                85                  90                  95 aac agg aag ggc ctc ata gct gcc atc tgt gcg ggt cct acg gcc ctg     336
Asn Arg Lys Gly Leu Ile Ala Ala Ile Cys Ala Gly Pro Thr Ala Leu
            100                 105                 110 ctg gct cac gaa gta ggc ttt gga tgc aag gtt aca tcg cac cca ttg     384
Leu Ala His Glu Val Gly Phe Gly Cys Lys Val Thr Ser His Pro Leu
        115                 120                 125 gct aag gac aaa atg atg aac ggc agt cac tac agc tac tca gag agc     432
Ala Lys Asp Lys Met Met Asn Gly Ser His Tyr Ser Tyr Ser Glu Ser
    130                 135                 140 cgt gtg gag aag gac ggc ctc atc ctc acc agc cgt ggg cct ggg acc     480
Arg Val Glu Lys Asp Gly Leu Ile Leu Thr Ser Arg Gly Pro Gly Thr
145                 150                 155                 160 agc ttc gag ttt gcg ctg gcc att gtg gag gca ctc agt ggc aag gac     528
Ser Phe Glu Phe Ala Leu Ala Ile Val Glu Ala Leu Ser Gly Lys Asp
                165                 170                 175 atg gct aac caa gtg aag gcc ccg ctt gtt ctc aaa gac tagagagccc     577
Met Ala Asn Gln Val Lys Ala Pro Leu Val Leu Lys Asp
            180                 185 aagccctgga ccctggaccc ccaggctgag caggcattgg aagcccacta gagagaccac     637
agcccagtga acctggcatt ggaagcccac tagtgtgtcc acagcccagt gaacctcagg     697
aactaacgtg tgaagtagcc cgctgctcag gaatctcgcc ctggctctgt actattctga     757
gccttgctag tagaataaac agttccccaa gctc                                 791

<210> SEQ ID NO 2
<211> LENGTH: 189
<212> TYPE: PRT
<213> ORGANISM: Rattus norvegicus

<400> SEQUENCE: 2

Met Ala Ser Lys Arg Ala Leu Val Ile Leu Ala Lys Gly Ala Glu Glu
1               5                   10                  15

Met Glu Thr Val Ile Pro Val Asp Ile Met Arg Arg Ala Gly Ile Lys
            20                  25                  30

Val Thr Val Ala Gly Leu Ala Gly Lys Asp Pro Val Gln Cys Ser Arg
        35                  40                  45

Asp Val Val Ile Cys Pro Asp Thr Ser Leu Glu Glu Ala Lys Thr Gln
    50                  55                  60

Gly Pro Tyr Asp Val Val Val Leu Pro Gly Gly Asn Leu Gly Ala Gln
```

```
                65                  70                  75                  80
Asn Leu Ser Glu Ser Ala Leu Val Lys Glu Ile Leu Lys Glu Gln Glu
                    85                  90                  95
Asn Arg Lys Gly Leu Ile Ala Ala Ile Cys Ala Gly Pro Thr Ala Leu
                    100                 105                 110
Leu Ala His Glu Val Gly Phe Gly Cys Lys Val Thr Ser His Pro Leu
                    115                 120                 125
Ala Lys Asp Lys Met Met Asn Gly Ser His Tyr Ser Tyr Ser Glu Ser
            130                 135                 140
Arg Val Glu Lys Asp Gly Leu Ile Leu Thr Ser Arg Gly Pro Gly Thr
145                 150                 155                 160
Ser Phe Glu Phe Ala Leu Ala Ile Val Glu Ala Leu Ser Gly Lys Asp
                    165                 170                 175
Met Ala Asn Gln Val Lys Ala Pro Leu Val Leu Lys Asp
            180                 185

<210> SEQ ID NO 3
<211> LENGTH: 189
<212> TYPE: PRT
<213> ORGANISM: Homo sapiens

<400> SEQUENCE: 3

Met Ala Ser Lys Arg Ala Leu Val Ile Leu Ala Lys Gly Ala Glu Glu
1               5                   10                  15
Met Glu Thr Val Ile Pro Val Asp Val Met Arg Arg Ala Gly Ile Lys
                20                  25                  30
Val Thr Val Ala Gly Leu Ala Gly Lys Asp Pro Val Gln Cys Ser Arg
            35                  40                  45
Asp Val Val Ile Cys Pro Asp Ala Ser Leu Glu Asp Ala Lys Lys Glu
        50                  55                  60
Gly Pro Tyr Asp Val Val Val Leu Pro Gly Gly Asn Leu Gly Ala Gln
65                  70                  75                  80
Asn Leu Ser Glu Ser Ala Ala Val Lys Glu Ile Leu Lys Glu Gln Glu
                    85                  90                  95
Asn Arg Lys Gly Leu Ile Ala Ala Ile Cys Ala Gly Pro Thr Ala Leu
                    100                 105                 110
Leu Ala His Glu Ile Gly Cys Gly Ser Lys Val Thr Thr His Pro Leu
                    115                 120                 125
Ala Lys Asp Lys Met Met Asn Gly Gly His Tyr Thr Tyr Ser Glu Asn
            130                 135                 140
Arg Val Glu Lys Asp Gly Leu Ile Leu Thr Ser Arg Gly Pro Gly Thr
145                 150                 155                 160
Ser Phe Glu Phe Ala Leu Ala Ile Val Glu Ala Leu Asn Gly Lys Glu
                    165                 170                 175
Val Ala Ala Gln Val Lys Ala Pro Leu Val Leu Lys Asp
            180                 185

<210> SEQ ID NO 4
<211> LENGTH: 989
<212> TYPE: DNA
<213> ORGANISM: Rattus norvegicus
<220> FEATURE:
<221> NAME/KEY: CDS
<222> LOCATION: (190)..(756)

<400> SEQUENCE: 4
gctgtgcaga gccgtctggc agggttgacc tcctaaaggg atattccatc tttattaatc    60
```

-continued

```
attagtagtg tggtcagaga cttagcacca ttggtctccc ccaacctggt ccagacattt      120
cagcagttta tcggaacagc aacaacagca acaaaacctt caaaatttac aagtctttaa      180 gaaatagaa atg gca tcc aaa aga gct ctg gtc atc cta gcc aaa gga gca      231
         Met Ala Ser Lys Arg Ala Leu Val Ile Leu Ala Lys Gly Ala
          1               5                  10 gag gag atg gag aca gtg att cct gtg gac atc atg cgg cga gct ggg        279
Glu Glu Met Glu Thr Val Ile Pro Val Asp Ile Met Arg Arg Ala Gly
 15              20                  25                  30 att aaa gtc acc gtt gca ggc ttg gct ggg aag gac ccc gtg cag tgt        327
Ile Lys Val Thr Val Ala Gly Leu Ala Gly Lys Asp Pro Val Gln Cys
                 35                  40                  45 agc cgt gat gta gtg att tgt ccg gat acc agt ctg gaa gaa gca aaa        375
Ser Arg Asp Val Val Ile Cys Pro Asp Thr Ser Leu Glu Glu Ala Lys
             50                  55                  60 aca cag gga cca tac gat gtg gtt gtt ctt cca gga gga aat ctg ggt        423
Thr Gln Gly Pro Tyr Asp Val Val Val Leu Pro Gly Gly Asn Leu Gly
         65                  70                  75 gca cag aac tta tct gag tcg gct ttg gtg aag gag atc ctc aag gag        471
Ala Gln Asn Leu Ser Glu Ser Ala Leu Val Lys Glu Ile Leu Lys Glu
     80                  85                  90 cag gag aac agg aag ggc ctc ata gct gcc atc tgt gcg ggt cct acg        519
Gln Glu Asn Arg Lys Gly Leu Ile Ala Ala Ile Cys Ala Gly Pro Thr
 95                  100                 105                 110 gcc ctg ctg gct cac gaa gta ggc ttt gga tgc aag gtt aca tcg cac        567
Ala Leu Leu Ala His Glu Val Gly Phe Gly Cys Lys Val Thr Ser His
                 115                 120                 125 cca ttg gct aag gac aaa atg atg aac ggc agt cac tac agc tac tca        615
Pro Leu Ala Lys Asp Lys Met Met Asn Gly Ser His Tyr Ser Tyr Ser
             130                 135                 140 gag agc cgt gtg gag aag gac ggc ctc atc ctc acc agc cgt ggg cct        663
Glu Ser Arg Val Glu Lys Asp Gly Leu Ile Leu Thr Ser Arg Gly Pro
         145                 150                 155 ggg acc agc ttc gag ttt gcg ctg gcc att gtg gag gca ctc agt ggc        711
Gly Thr Ser Phe Glu Phe Ala Leu Ala Ile Val Glu Ala Leu Ser Gly
     160                 165                 170 aag gac atg gct aac caa gtg aag gcc ccg ctt gtt ctc aaa gac            756
Lys Asp Met Ala Asn Gln Val Lys Ala Pro Leu Val Leu Lys Asp
175                 180                 185 tagagagccc aagccctgga ccctggaccc ccaggctgag caggcattgg aagcccacta     816
gtgtgtccac agcccagtga acctggcatt ggaagcccac tagtgtgtcc acagcccagt     876
gaacctcagg aactaacgtg tgaagtagcc cgctgctcag gaatctcgcc ctggctctgt     936
actattctga gccttgctag tagaataaac agttccccaa gctcctgacg gct             989

<210> SEQ ID NO 5
<211> LENGTH: 851
<212> TYPE: DNA
<213> ORGANISM: Rattus norvegicus
<220> FEATURE:
<221> NAME/KEY: CDS
<222> LOCATION: (52)..(618)

<400> SEQUENCE: 5
tggcttcgcg tgggtggagg aggcgcggct gcaggtctttt aagaaataga a atg gca     57
                                                           Met Ala
                                                            1 tcc aaa aga gct ctg gtc atc cta gcc aaa gga gca gag gag atg gag        105
Ser Lys Arg Ala Leu Val Ile Leu Ala Lys Gly Ala Glu Glu Met Glu
         5                  10                  15 aca gtg att cct gtg gac atc atg cgg cga gct ggg att aaa gtc acc        153
Thr Val Ile Pro Val Asp Ile Met Arg Arg Ala Gly Ile Lys Val Thr
```

```
Thr Val Ile Pro Val Asp Ile Met Arg Arg Ala Gly Ile Lys Val Thr
    20                  25                  30 gtt gca ggc ttg gct ggg aag gac ccc gtg cag tgt agc cgt gat gta    201
Val Ala Gly Leu Ala Gly Lys Asp Pro Val Gln Cys Ser Arg Asp Val
 35                  40                  45                  50 gtg att tgt ccg gat acc agt ctg gaa gaa gca aaa aca cag gga cca    249
Val Ile Cys Pro Asp Thr Ser Leu Glu Glu Ala Lys Thr Gln Gly Pro
                 55                  60                  65 tac gat gtg gtt gtt ctt cca gga gga aat ctg ggt gca cag aac tta    297
Tyr Asp Val Val Val Leu Pro Gly Gly Asn Leu Gly Ala Gln Asn Leu
                     70                  75                  80 tct gag tcg gct ttg gtg aag gag atc ctc aag gag cag gag aac agg    345
Ser Glu Ser Ala Leu Val Lys Glu Ile Leu Lys Glu Gln Glu Asn Arg
                 85                  90                  95 aag ggc ctc ata gct gcc atc tgt gcg ggt cct acg gcc ctg ctg gct    393
Lys Gly Leu Ile Ala Ala Ile Cys Ala Gly Pro Thr Ala Leu Leu Ala
            100                 105                 110 cac gaa gta ggc ttt gga tgc aag gtt aca tcg cac cca ttg gct aag    441
His Glu Val Gly Phe Gly Cys Lys Val Thr Ser His Pro Leu Ala Lys
115                 120                 125                 130 gac aaa atg atg aac ggc agt cac tac agc tac tca gag agc cgt gtg    489
Asp Lys Met Met Asn Gly Ser His Tyr Ser Tyr Ser Glu Ser Arg Val
                135                 140                 145 gag aag gac ggc ctc atc ctc acc agc cgt ggg cct ggg acc agc ttc    537
Glu Lys Asp Gly Leu Ile Leu Thr Ser Arg Gly Pro Gly Thr Ser Phe
            150                 155                 160 gag ttt gcg ctg gcc att gtg gag gca ctc agt ggc aag gac atg gct    585
Glu Phe Ala Leu Ala Ile Val Glu Ala Leu Ser Gly Lys Asp Met Ala
        165                 170                 175 aac caa gtg aag gcc ccg ctt gtt ctc aaa gac tagagagccc aagccctgga  638
Asn Gln Val Lys Ala Pro Leu Val Leu Lys Asp
    180                 185 ccctggaccc ccaggctgag caggcattgg aagcccacta gtgtgtccac agcccagtga  698
acctggcatt ggaagcccac tagtgtgtcc acagcccagt gaacctcagg aactaacgtg  758
tgaagtagcc cgctgctcag gaatctcgcc ctggctctgt actattctga gccttgctag  818
tagaataaac agttccccaa gctcctgacg gct                                851

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Val Ala Gly Leu Ala Gly Lys Asp Pro Val Gln Cys Ser Arg
1               5                   10                  15

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Gly Leu Ile Leu Thr Ser Arg
1               5
```

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Glu Glu Ala Lys Thr Gln Gly Pro Tyr Asp Val Val Val Leu
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Lys Glu Ile Leu Lys Glu Gln Glu Asn Arg Lys Gly Leu Ile
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Phe Gly Cys Lys Val Thr Ser His Pro Leu Ala Lys Asp Lys
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Ser Phe Glu Phe Ala Leu Ala Ile Val Glu Ala Leu Ser Gly
1               5                   10                  15

<210> SEQ ID NO 12
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Arg Asp Val Val Ile Cys Pro Asp Thr Ser Leu Glu Glu Ala Lys
1               5                   10                  15

Thr Gln Gly Pro Tyr Asp Val Val Val Leu Pro Gly Gly Asn Leu Gly
            20                  25                  30

Ala Gln Asn Leu Ser Glu Ser Ala Leu Val Lys Glu Ile Leu Lys Glu
        35                  40                  45

Gln Glu Asn Arg Lys Gly Leu Ile
    50                  55

<210> SEQ ID NO 13

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Met Ala Ser Lys Arg Ala Leu Val Ile Leu Ala Lys Gly Ala Glu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Arg Ala Leu Val Ile Leu Ala Lys Gly Ala Glu Glu Met Glu
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Val Ile Leu Ala Lys Gly Ala Glu Glu Met Glu Thr Val Ile
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Ala Lys Gly Ala Glu Glu Met Glu Thr Val Ile Pro Val Asp
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Ala Glu Glu Met Glu Thr Val Ile Pro Val Asp Ile Met Arg
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Met Glu Thr Val Ile Pro Val Asp Ile Met Arg Arg Ala Gly
```

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Val Ile Pro Val Asp Thr Met Arg Arg Ala Gly Ile Lys Val
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Pro Val Asp Ile Met Arg Arg Ala Gly Ile Lys Val Thr Val Ala
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ile Met Arg Arg Ala Gly Ile Lys Val Thr Val Ala Gly Leu Ala
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ala Gly Ile Lys Val Thr Val Ala Gly Leu Ala Gly Lys Asp
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ile Lys Val Thr Val Ala Gly Leu Ala Gly Lys Asp Pro Val Gln
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 24

Thr Val Ala Gly Leu Ala Gly Lys Asp Pro Val Gln Cys Ser Arg
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Leu Ala Gly Lys Asp Pro Val Gln Cys Ser Arg Asp Val Val
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Lys Asp Pro Val Gln Cys Ser Arg Asp Val Val Ile Cys Pro
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Pro Val Gln Cys Ser Arg Asp Val Val Ile Cys Pro Asp Thr Ser
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys Ser Arg Asp Val Val Ile Cys Pro Asp Thr Ser Leu Glu Glu
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Val Val Ile Cys Pro Asp Thr Ser Leu Glu Glu Ala Lys Thr
1               5                   10                  15

<210> SEQ ID NO 30
<211> LENGTH: 15
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 30

Ile Cys Pro Asp Thr Ser Leu Glu Glu Ala Lys Thr Gln Ser Pro
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Thr Ser Leu Glu Glu Ala Lys Thr Gln Gly Pro Tyr Asp Val
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Glu Glu Ala Lys Thr Gln Gly Pro Tyr Asp Val Val Val Leu
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Lys Thr Gln Gly Pro Tyr Asp Val Val Val Leu Pro Gly Gly
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Gly Pro Tyr Asp Val Val Val Leu Pro Gly Gly Asn Leu Gly
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Asp Val Val Val Leu Pro Gly Gly Asn Leu Gly Ala Gln Asn
1               5                   10                  15

```
<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Val Leu Pro Gly Gly Asn Leu Gly Ala Gln Asn Leu Ser Glu
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Pro Gly Gly Asn Leu Gly Ala Gln Asn Leu Ser Glu Ser Ala Leu
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asn Leu Gly Ala Gln Asn Leu Ser Glu Ser Ala Leu Val Lys Glu
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Gln Asn Leu Ser Glu Ser Ala Leu Val Lys Glu Ile Leu Lys
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Ser Glu Ser Ala Leu Val Lys Glu Ile Leu Lys Glu Gln Glu
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41
```

```
Ser Ala Leu Val Lys Glu Ile Leu Lys Glu Gln Glu Asn Arg Lys
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Val Lys Glu Ile Leu Lys Glu Gln Glu Asn Arg Lys Gly Leu Ile
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Leu Lys Glu Gln Glu Asn Arg Lys Gly Leu Ile Ala Ala Ile
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Glu Gln Glu Asn Arg Lys Gly Leu Ile Ala Ala Ile Cys Ala Gly
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asn Arg Lys Gly Leu Ile Ala Ala Ile Cys Ala Gly Pro Thr Ala
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Leu Ile Ala Ala Ile Cys Ala Gly Pro Thr Ala Leu Leu Ala
1               5                   10                  15

<210> SEQ ID NO 47
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 47

Ala Ala Ile Cys Ala Gly Pro Thr Ala Leu Leu Ala His Glu Val
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Cys Ala Gly Pro Thr Ala Leu Leu Ala His Glu Val Gly Phe Gly
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Pro Thr Ala Leu Leu Ala His Glu Val Gly Phe Gly Cys Lys Val
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Leu Ala His Glu Val Gly Phe Gly Cys Lys Val Thr Ser His
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

His Glu Val Gly Phe Gly Cys Lys Val Thr Ser His Pro Leu Ala
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Phe Gly Cys Lys Val Thr Ser His Pro Leu Ala Lys Asp Lys
1               5                   10                  15

<210> SEQ ID NO 53
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Cys Lys Val Thr Ser His Pro Leu Ala Lys Asp Lys Met Met Asn
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Thr Ser His Pro Leu Ala Lys Asp Lys Met Met Asn Gly Ser His
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Pro Leu Ala Lys Asp Lys Met Met Asn Gly Ser His Tyr Ser Tyr
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Lys Asp Lys Met Met Asn Gly Ser His Tyr Ser Tyr Ser Glu Ser
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Met Met Asn Gly Ser His Tyr Ser Tyr Ser Glu Ser Arg Val Glu
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Ser His Tyr Ser Tyr Ser Glu Ser Arg Val Glu Lys Asp Gly
```

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Tyr Ser Tyr Ser Glu Ser Arg Val Glu Lys Asp Gly Leu Ile Leu
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Ser Glu Ser Arg Val Glu Lys Asp Gly Leu Ile Leu Thr Ser Arg
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Arg Val Glu Lys Asp Gly Leu Ile Leu Thr Ser Arg Gly Pro Gly
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Lys Asp Gly Leu Ile Leu Thr Ser Arg Gly Pro Gly Thr Ser Phe
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Leu Ile Leu Thr Ser Arg Gly Pro Gly Thr Ser Phe Glu Phe Ala
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Thr Ser Arg Gly Pro Gly Thr Ser Phe Glu Phe Ala Leu Ala Ile
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Pro Gly Thr Ser Phe Glu Phe Ala Leu Ala Ile Val Glu Ala
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Thr Ser Phe Glu Phe Ala Leu Ala Ile Val Glu Ala Leu Ser Gly
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Glu Phe Ala Leu Ala Ile Val Glu Ala Leu Ser Gly Lys Asp Met
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Leu Ala Ile Val Glu Ala Leu Ser Gly Lys Asp Met Ala Asn Gln
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Val Glu Ala Leu Ser Gly Lys Asp Met Ala Asn Gln Val Lys Ala
1               5                   10                  15

<210> SEQ ID NO 70
<211> LENGTH: 15
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 70

Leu Ser Gly Lys Asp Met Ala Asn Gln Val Lys Ala Pro Leu Val
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Lys Asp Met Ala Asn Gln Val Lys Ala Pro Leu Val Leu Lys Asp
1               5                   10                  15

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 72

His His His His His His
1               5

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Lys Asp Pro Val Gln Cys Ser Arg Asp Val Val Ile Cys Pro Asp
1               5                   10                  15

Thr Ser

<210> SEQ ID NO 74
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Asn Leu Ser Glu Ser Ala Leu Val Lys Glu Ile Leu Lys Glu Gln
1               5                   10                  15

Glu Asn Arg Lys Gly Leu Ile
            20

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 75

Val Thr Val Ala Gly Leu Ala Gly Lys Asp Pro Val Gln Cys Ser Arg
1               5                   10                  15

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Glu Glu Ala Lys Thr Gln Gly Pro Tyr Asp Val
1               5                   10
```

DIAGNOSTIC KITS TO DETECT SP22 AND SP22 ANTIBODIES

RELATED APPLICATIONS

This application claims priority to PCT Application No. PCT/US07/062056, filed Feb. 13, 2007, which claims the benefit of U.S. Application No. 60/772,737, filed Feb. 13, 2006. These applications are incorporated herein by reference in their entireties.

BACKGROUND

Approximately one in six couples find themselves involuntarily infertile. This translates to between two and four million couples in the United States alone. Although numerous tests are available for diagnosing infertility problems, 16% of all couples that seek medical treatment are diagnosed with what is described clinically as "unexplained infertility".

Tests to evaluate fertility in men have relied on conventional sperm analysis, in which sperm count and sperm motility are the primary factors. However, in conventional sperm analysis there are no strict threshold levels separating fertility from infertility, except in the situation wherein there are no moving sperm, which is always associated with infertility. A sperm count of twenty million sperm per milliliter or greater is generally considered to be in the fertile range, whereas a lower count is considered subfertile. There is some disagreement on this in that some laboratories and clinicians use rates of thirty million sperm per milliliter or forty million sperm per milliliter as the fertility threshold. These values are not fixed in that it has been determined that twenty percent of human males with counts below twenty million sperm per milliliter will father children and as many as fifteen percent of human males with normal sperm counts may have some degree of sperm dysfunction due to other reasons which interfere with fertility. A sperm specimen with normal sperm count or with normal sperm motility does not invariably establish fertility in that individual. In addition, there is disagreement as to what constitutes the lower limit of sperm motility that can be considered normal or fertile, with estimates ranging between forty to sixty percent of the sperm in a given sample. In summary, conventional sperm analysis is not one hundred percent accurate, and is not a reliable indicator of male fertility. Thus, there remains a need for diagnostic tests for determining fertility in males that are both accurate and easy to use.

SUMMARY

In one aspect, the invention features methods for detecting infertility in a male subject by detecting the level of SP22 in a sperm sample from the male subject, wherein a decreased level of SP22 relative to the normal level is indicative of infertility. In a preferred embodiment, the level of SP22 is determined using an immunoassay.

In another aspect, the invention features methods for determining the fertilization potential of a male subject comprising separating a subset of sperm from a sperm sample, wherein the subset of sperm have an average motility that is higher than the average motility of sperm in the sample, and determining the presence of SP22 on sperm of the subset of sperm.

In another aspect, the invention features methods for monitoring the fertility status of a subject undergoing SP22 vaccination comprising detecting SP22 antibody levels in a female subject, wherein an increased level of SP22 antibody (relative to the level of a non-vaccinated subject) indicates that the subject is protected against fertilization. In a preferred embodiment, the level of SP22 antibody is determined using an immunoassay.

In another aspect, the invention features kits for determining the level of SP22 in a sperm sample from a male subject. A kit of the invention may be used to determine male fertility or the fertilization potential of a male subject. A kit of the invention may comprise an SP22 antibody, an application zone for adding a sperm sample, and a detection zone for determining if SP22 is present on the surface of sperm in the sperm sample. A kit may further comprise a barrier zone separating the application zone and the detection zone, wherein the barrier zone separates a subset of sperm having an average motility higher than the average motility of the sperm sample.

In another aspect, the invention also features kits for determining the level of SP22 antibody in a female subject. A kit of the invention may comprise a device for collecting a vaginal sample and a monitoring device comprising SP22 conjugated to a detectable marker.

In another aspect, the invention provides pharmaceutical compositions comprising an effective spermicidal amount of an antibody that binds to SP22 (SEQ ID NO: 2) and a pharmaceutically acceptable carrier. In preferred embodiments, the antibody specifically binds to amino acids 40-57, amino acids 58-72, amino acids 88-102, amino acids 80-102, amino acids 118-132, amino acids 160-174, and/or amino acids 47-102 of SEQ ID NO: 2. The pharmaceutical composition, which may be in the form of a cream, lotion, gel, foam, sponge, suppository or lubricant, may be administered with an applicator. Preferred pharmaceutical compositions comprise at least one other active ingredient, including a second spermicidal agent, an anti-fungal agent, an anti-bacterial agent, and an anti-viral agent. In a further aspect, the invention features a kit comprising an applicator and said pharmaceutical composition.

In another aspect, the invention features methods for preventing conception in a subject, comprising administering to the subject a pharmaceutical composition comprising an effective spermicidal amount of an antibody that binds to SP22 (SEQ ID NO: 2) and a pharmaceutically acceptable carrier. In one embodiment, the pharmaceutical composition is administered to a female subject. In a preferred embodiment, the administration is intravaginal, for example via an applicator or suppository or on a barrier type device, such as a condom, diaphragm, cap, or sponge.

In yet another aspect, the invention features a vaccine composition comprising an SP22 polypeptide and a pharmaceutically acceptable carrier. In one embodiment, the SP22 polypeptide comprises amino acids 34-48 of SEQ ID NO: 2. In another embodiment, the SP22 polypeptide comprises amino acids 40-57 of SEQ ID NO: 2. In another embodiment, the SP22 polypeptide comprises amino acids 58-72 of SEQ ID NO: 2. In another embodiment, the SP22 polypeptide comprises amino acids 88-102 of SEQ ID NO: 2. In another embodiment, the SP22 polypeptide comprises amino acids 80-102 of SEQ ID NO: 2. In another embodiment, the SP22 polypeptide comprises amino acids 118-132 or amino acids 136-150 of SEQ ID NO: 2. In a further embodiment, the SP22 polypeptide comprises amino acids 160-174 of SEQ ID NO: 2. In a still further embodiment, the SP22 polypeptide comprises amino acids 47-102 of SEQ ID NO: 2. The vaccine composition may be formulated in a pill, tablet, capsule, suppository, lozenge, granule, powder or syrup. Alternatively, the vaccine composition may be formulated into an injectable formulation and may further comprise an adjuvant.

The invention further features contraceptive methods comprising administering to a subject a vaccine composition comprising an SP22 polypeptide and a pharmaceutically acceptable carrier in an effective amount to stimulate production of antibodies that are immunologically reactive against SP22 protein. The vaccine composition may be administered to a male or female subject either orally, intravenously, intramuscularly, subcutaneously, intranasally or intravaginally.

Further features and advantages of the instant disclosed inventions will now be discussed in conjunction with the following Detailed Description and Claims.

BRIEF DESCRIPTION OF THE DRAWINGS

FIG. 1A shows the nucleotide (SEQ ID NO: 1) and amino acid (SEQ ID NO: 2) sequences of SP22. FIG. 1B is a comparison of amino acid sequences of SP22 and DJ-1 (SEQ ID NO: 3). Underlined amino acid sequences represent the four peptides identified following Edman degradation of SP22. SP22 amino acids identical to DJ-1 amino acids are indicated by solid bars, conservative substitutions are indicated by a colon, and divergent residues are indicated by gaps.

FIG. 2 is an alignment of nucleotide sequences of two spliced variants of SP22; SP22A (SEQ ID NO: 4) and SP22B (SEQ ID NO: 5). The divergent 5' ends of the SP22 nucleotide sequences are designated A (plain text) and B (italics). The canonical polyadenylation signal (AATAAA) is underlined. Observed multiple polyadenylation sites are indicated by asterisks. FIG. 2 also shows the amino acid sequences of SP22 (SEQ ID NO: 2).

FIG. 4 provides graphs showing the correlation between fertility in rats and SP22 protein levels following exposure of male rats to epididymal toxicants (top) and testicular toxicants (bottom). It should be noted that the biphasic, threshold relationship is maintained regardless of the type of insult.

FIG. 19A shows a control subcutaneous immunization; 19B shows subcutaneous immunization with Peptide X (QNLS-ESALVKEILKEQENRKGLI; amino acids 80-102 of SEQ ID NO: 2) (SEQ ID NO: 74); 19C shows a control intravaginal immunization; and 19D shows intravaginal immunization with Peptide X.

FIG. 23A depicts immunolocalization of affinity purified N-terminal truncated rSP22 antibody on ejaculated rabbit sperm. FIG. 23B shows that immunostaining over the equatorial segment of the rabbit sperm head is reduced when Peptide C is added to the antibody suggesting that at least a portion of the Peptide C sequence is exposed on the sperm surface. FIG. 23C shows that immunostaining over the equatorial segment is dramatically reduced although still apparent when Peptide X (or D) is added to the antibody. This suggests that most of the immunostaining observed with this antibody is attributed to the Peptide D/X epitope. In reality, the expression in B) reflects the antibody's binding to the Peptide D/X epitope and the expression in C) reflects the antibody's binding to the Peptide C epitope.

DETAILED DESCRIPTION

1. General

Figure 3A:
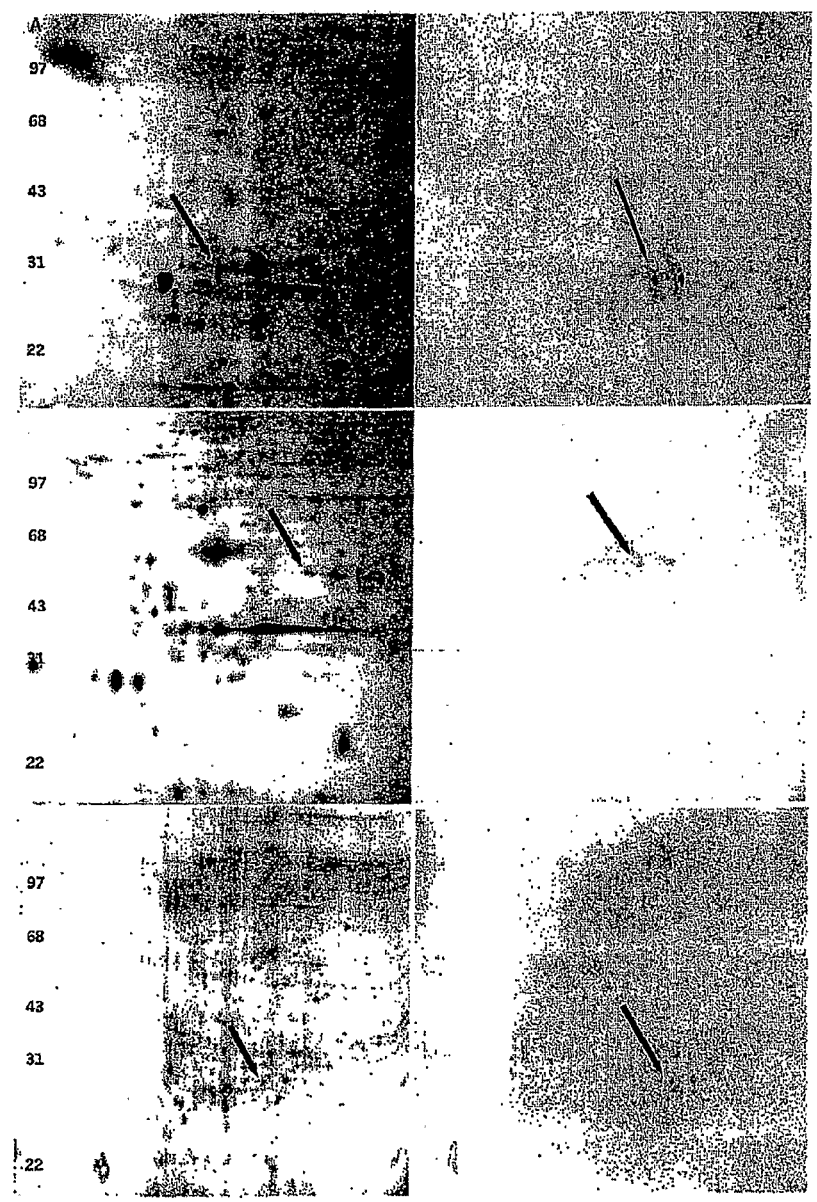
FIG. 3A shows silver stained two dimensional gels and corresponding immunoblots showing immunolocalization of SP22 using anti-SP22 peptide immunoglobulin (Ig) in rat cauda epididymal sperm extract (top), rat cauda sperm membrane preparation (middle), and rat testis sperm extract (bottom).

The invention features SP22 antibody based diagnostics that can be used, for example, to diagnose infertility in males or determine the fertilization potential of a male subject. The invention also features diagnostics to evaluate the effectiveness of an SP22 immunization. The invention further features kits for determining the level of SP22 present in a sperm sample in a male subject. A decreased level of SP22 relative to the normal level is indicative of infertility. In addition, the invention features a kit for monitoring the fertility status of a subject undergoing SP22 vaccination comprising detecting SP22 antibody levels in a female subject. An increased level of SP22 antibody (relative to the level of a non-vaccinated subject) indicates that the subject is protected against fertilization.

2. Definitions

For convenience, certain terms employed in the specification, examples, and appended claims are provided below. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

As used herein, the term "adjuvant" refers to a substance that elicits an enhanced immune response when used in combination with a specific antigen.

As used herein the term "antibody" refers to an immunoglobulin and any antigen-binding portion of an immunoglobulin (e.g. IgG, IgD, IgA, IgM and IgE) i.e., a polypeptide that contains an antigen binding site, which specifically binds ("immunoreacts with") an antigen. Antibodies can comprise at least one heavy (H) chain and at least one light (L) chain inter-connected by at least one disulfide bond. The term "$V_H$" refers to a heavy chain variable region of an antibody. The term "$V_L$" refers to a light chain variable region of an antibody. In exemplary embodiments, the term "antibody" specifically covers monoclonal and polyclonal antibodies. A "polyclonal antibody" refers to an antibody which has been derived from the sera of animals immunized with an antigen or antigens. A "monoclonal antibody" refers to an antibody produced by a single clone of hybridoma cells. Techniques for generating monoclonal antibodies include, but are not limited to, the hybridoma technique (see Kohler & Milstein (1975) *Nature* 256:495-497); the trioma technique; the human B-cell hybridoma technique (see Kozbor, et al. (1983) *Immunol. Today* 4:72), the EBV hybridoma technique (see Cole, et al., 1985 In: *Monoclonal Antibodies and Cancer Therapy*, Alan R. Liss, Inc., pp. 77-96) and phage display.

Polyclonal or monoclonal antibodies can be further manipulated or modified to generate chimeric or humanized antibodies. "Chimeric antibodies" are encoded by immunoglobulin genes that have been genetically engineered so that the light and heavy chain genes are composed of immunoglobulin gene segments belonging to different species. For example, substantial portions of the variable (V) segments of the genes from a mouse monoclonal antibody, e.g., obtained as described herein, may be joined to substantial portions of human constant (C) segments. Such a chimeric antibody is likely to be less antigenic to a human than a mouse monoclonal antibody.

As used herein, the term "humanized antibody" (HuAb) refers to a chimeric antibody with a framework region substantially identical (i.e., at least 85%) to a human framework, having CDRs from a non-human antibody, and in which any constant region has at least about 85-90%, and preferably about 95% polypeptide sequence identity to a human immunoglobulin constant region. See, for example, PCT Publication WO 90/07861 and European Patent No. 0451216. All parts of such a HuAb, except possibly the CDRs, are substantially identical to corresponding parts of one or more native human immunoglobulin sequences. The term "framework region" as used herein, refers to those portions of immunoglobulin light and heavy chain variable regions that are relatively conserved (i.e., other than the CDRs) among different immunoglobulins in a single species, as defined by Kabat, et al. (1987) *Sequences of Proteins of Immunologic Interest*, 4$^{th}$ Ed., US Dept. Health and Human Services. Human constant region DNA sequences can be isolated in accordance with well known procedures from a variety of human cells, but preferably from immortalized B cells. The variable regions or CDRs for producing humanized antibodies may be derived from monoclonal antibodies capable of binding to the antigen, and will be produced in any convenient mammalian source, including mice, rats, rabbits, or other vertebrates.

The term "antibody" also encompasses antibody fragments. Examples of antibody fragments include Fab, Fab', Fab'-SH, F(ab')$_2$, and Fv fragments; diabodies and any antibody fragment that has a primary structure consisting of one uninterrupted sequence of contiguous amino acid residues, including without limitation: single-chain Fv (scFv) molecules, single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s). Suitable leucine zipper sequences include the jun and fos leucine zippers taught by Kostelney et al., *J. Immunol.*, 148: 1547-1553 (1992) and the GCN4 leucine zipper described in U.S. Pat. No. 6,468,532. Fab and F(ab')$_2$ fragments lack the Fc fragment of intact antibody and are typically produced by proteolytic cleavage, using enzymes such as papain (to produce Fab fragments) or pepsin (to produce F(ab')$_2$ fragments).

An antibody "specifically binds" to an antigen or an epitope of an antigen if the antibody binds preferably to the antigen over most other antigens. For example, the antibody may have less than about 50%, 20%, 10%, 5%, 1% or 0.1% cross-reactivity toward one or more other epitopes.

The term "contraceptive" as used herein refers to SP22 antifertility vaccines or SP22 antibodies which may be taken orally, applied topically or injected to prevent the occurrence of pregnancy.

An "effective amount" is an amount sufficient to produce a beneficial or desired clinical result upon treatment. An effective amount can be administered to a patient in one or more doses. In terms of treatment, an effective amount is an amount that is sufficient to increase or decrease fertility in a patient. Several factors are typically taken into account when determining an appropriate dosage to achieve an effective amount. These factors include age, sex and weight of the patient, the condition being treated, the severity of the condition and the form and effective concentration of the agent administered.

The term "epitope" refers to that region of an antigen to which an antibody binds preferentially and specifically. A monoclonal antibody binds preferentially to a single specific epitope of a molecule that can be molecularly defined. An epitope of a particular protein may be constituted by a limited number of amino acid residues, e.g. 5-15 residues, that are either in a linear or non-linear organization on the protein.

"Equivalent" when used to describe nucleic acids or nucleotide sequences refers to nucleotide sequences encoding functionally equivalent polypeptides. Equivalent nucleotide sequences will include sequences that differ by one or more nucleotide substitutions, additions or deletions, such as allelic variants; and will, therefore, include sequences that differ from the nucleotide sequence of the nucleic acids of SP22 due to the degeneracy of the genetic code.

"Homology" or alternatively "identity" refers to sequence similarity between two peptides or between two nucleic acid molecules. Homology may be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. The term "percent identical" refers to sequence identity between two amino acid sequences or between two nucleotide sequences. Identity may be determined by comparing a position in each sequence which may be aligned for purposes of comparison. When an equivalent position in the compared sequences is occupied by the same base or amino acid, then the molecules are identical at that position; when the equivalent site is occupied by the same or a similar amino acid residue (e.g., similar in steric and/or electronic nature), then the molecules may be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and may be used with, e.g., default settings. ENTREZ is available through the National Center for Biotechnology Information, National Library of Medicine, National Institutes of Health, Bethesda, Md. In one embodiment, the percent identity of two sequences may be determined by the GCG program with a gap weight of 1, e.g., each amino acid gap is weighted as if it were a single amino acid or nucleotide mismatch between the two sequences. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See *Meth. Mol. Biol.* 70: 173-187 (1997). Also, the GAP program using the Needleman and Wunsch alignment method may be utilized to align sequences. An alternative search strategy uses MPSRCH software, which runs on a MASPAR computer. MPSRCH uses a Smith-Waterman algorithm to score sequences on a massively parallel computer. This approach improves the ability to pick up distantly related matches, and is especially tolerant of small gaps and nucleotide sequence errors. Nucleic acid-encoded amino acid sequences may be used to search both protein and DNA databases. Databases with individual sequences are described in *Methods in Enzymology*, ed. Doolittle, supra. Databases include Genbank, EMBL, and DNA Database of Japan (DDBJ).

"Label" and "detectable label" refer to a molecule capable of detection including, but not limited to radioactive isotopes, fluorophores, chemiluminescent moieties, enzymes, enzyme substrates, enzyme cofactors, enzyme inhibitors, dyes, metal ions, ligands (e.g., biotin or haptens) and the like. "Fluorophore" refers to a substance or a portion thereof which is capable of exhibiting fluorescence in the detectable range. Particular examples of labels which may be used under the invention include fluorescein, rhodamine, dansyl, umbelliferone, Texas red, luminol, NADPH, alpha- or beta-galactosidase and horseradish peroxidase.

The terms "polynucleotide", and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term "recombinant" polynucleotide means a polynucleotide of genomic, cDNA, semisynthetic, or synthetic origin which either does not occur in nature or is linked to another polynucleotide in a nonnatural arrangement. An "oligonucleotide" refers to a single stranded polynucleotide having less than about 100 nucleotides, less than about, e.g. 75, 50, 25, or 10 nucleotides.

The terms "polypeptide", "peptide" and "protein" (if single chain) are used interchangeably herein to refer to polymers of amino acids. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

"SP22 polypeptide" as used herein refers to Sperm Protein 22 kDa. The sequence of SP22 polypeptide is as set forth in SEQ ID NO: 2 and is encoded by SEQ ID NO: 1. The term also encompasses any fragments, variants, analogs, agonists, chemical derivatives, functional derivatives or functional fragments of a SP22 polypeptide. "SP22 immunogens" are SP22 polypeptides which are capable of eliciting an immune response in a subject.

A "variant" of a SP22 polypeptide refers to a molecule which is substantially similar to SP22. Variant peptides may be covalently prepared by direct chemical synthesis of the variant peptide, using methods well known in the art. Variants of SP22 may further include, for example, deletions, insertions or substitutions of residues within the amino acid sequence. Any combination of deletion, insertion, and substitution may also be made to arrive at the final construct, provided that the final construct possesses the desired activity. These variants may be prepared by site-directed mutagenesis, (as exemplified by Adelman et al., *DNA* 2: 183 (1983)) of the nucleotides in the DNA encoding the peptide molecule thereby producing DNA encoding the variant and thereafter expressing the DNA in recombinant cell culture. The variants typically exhibit the same qualitative biological activity as the wild type SP22 polypeptide. It is known in the art that one may also synthesize all possible single amino acid substitutions of a known polypeptide (Geysen et al., *Proc. Nat. Acad. Sci.* (*USA*) 18:3998-4002 (1984)). While the effects of different substitutions are not always additive, it is reasonable to expect that two favorable or neutral single substitutions at different residue positions in a SP22 polypeptide can safely be combined without losing any SP22 activity. Methods for the preparation of degenerate polypeptides are as described in Rutter, U.S. Pat. No. 5,010,175; Haughter et al., *Proc. Nat. Acad. Sci.* (*USA*) 82:5131-5135 (1985); Geysen et al., *Proc. Nat. Acad. Sci.* (*USA*) 18:3998-4002 (1984); WO86/06487; and WO86/00991. In devising a substitution strategy, a person of ordinary skill would determine which residues to vary and which amino acids or classes of amino acids are suitable replacements. One may also take into account studies of sequence variations in families or naturally occurring homologous proteins. Certain amino acid substitutions are more often tolerated than others, and these are often correlated with similarities in size, charge, etc., between the original amino acid and its replacement. Insertions or deletions of amino acids may also be made, as described above. The substitutions are preferably conservative, see, e.g., Schulz et al., *Principle of Protein Structure* (Springer-Verlag, New York (1978)); and Creighton, *Proteins: Structure and Molecular Properties* (W. H. Freeman & Co., San Francisco (1983)); both of which are hereby incorporated by reference in their entireties. Conservative substitutions may be defined herein as exchanges within one of the following five groups:

I. Small aliphatic, nonpolar or slightly polar residues: Ala, Ser, Thr, Pro, Gly
II. Polar, negatively charged residues and their amides: Asp, Asn, Glu, Gln
III. Polar, positively charged residues: His, Arg., Lys
IV. Large, aliphatic nonpolar residues: Met, Leu, Ile, Val, Cys
V. Large aromatic residues: Phe, Try, Trp Within the foregoing groups the following five substitutions are considered "highly conservative": Asp/Glu; His/Arg/Lys; Phe/Tyr/Trp; Met/Leu/Ile/Val.

Semi-conservative substitutions are defined to be exchanges between two of groups (I)-(V) above which are limited to supergroup (A), comprising (I), (II), and (III) above, or to supergroup (B), comprising (IV) and (V) above. Substitutions are not limited to the genetically encoded, or even the naturally occurring amino acids.

Conservative amino acid substitutions according to the present invention, e.g., as presented above, are known in the art and would be expected to maintain the biological and structural properties of the polypeptide after such amino acid substitutions. Most deletions, insertions, and substitutions according to the present invention are those which do not produce radical changes in the characteristics of the polypeptide. One skilled in the art will appreciate that the effect of substitution can be evaluated by routine screening assays, either immunoassays or bioassays.

A "chemical derivative" of SP22 polypeptide can contain additional chemical moieties not normally part of the SP22 amino acid sequence. Such chemical modifications may be introduced into the SP22 by reacting targeted amino acid residues of the polypeptide with an organic derivatizing agent that is capable of reacting with selected side chains or terminal residues. Amino terminal residues can be reacted with succinic or other carboxylic acid anhydrides. Other suitable reagents for derivatizing alpha-amino-containing residues include amidoesters such as methyl picolinimidate; pyridoxal phosphate; pyridoxal; chloroborohydride; trinitrobenzenesulfonic acid; O-methylisourea; 2,4-pentanedione; and transaminase-catalase reacted with glyoxylate. Specific modifications of tyrosyl residues per se have been studied extensively, with particular interest in introducing spectral labels into tyrosyl residues by reaction with aromatic diazonium compounds or tetranitromethane. Most commonly, N-acetylimidazole and tetranitromethane are use to form O-acetyl tyrosyl species and 3-nitro derivatives, respectively. Carboxyl side groups such as aspartyl or glutamyl can be selectively modified by reaction with carbodiimides (R'N—C—N—R') such as 1-cyclohexy-3-[2-morpholinyl-(4-ethyl)]carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonium ions.

The term "substantially homologous" when used in connection with amino acid sequences, refers to sequences which are substantially identical to or similar in sequence with each other, giving rise to a homology of conformation and thus to retention, to a useful degree, of one or more biological (including immunological) activities. The term is not intended to imply a common evolution of the sequences.

A "subject" refers to a male or female mammal, including human and non-human mammals (e.g., horses, cows, pigs, rodents).

A "vector" is a self-replicating nucleic acid molecule that transfers an inserted nucleic acid molecule into and/or between host cells. The term includes vectors that function primarily for insertion of a nucleic acid molecule into a cell, replication of vectors that function primarily for the replication of nucleic acid, and expression vectors that function for transcription and/or translation of the DNA or RNA. Also included are vectors that provide more than one of the above functions. As used herein, "expression vectors" are defined as polynucleotides which, when introduced into an appropriate host cell, can be transcribed and translated into a polypeptide(s). An "expression system" usually connotes a suitable host cell comprised of an expression vector that can function to yield a desired expression product.

3. SP22 Polypeptide and Uses Thereof

As disclosed herein, SP22 polypeptides are significantly correlated and predictive of fertility. In particular, Example 5 provides evidence that levels of SP22 protein recovered in detergent extracts of cauda epididymal sperm from rats exposed to testicular toxicants or epididymal toxicants were highly correlated with the fertility of the sperm in in vitro insemination experiments.

An alignment of SP22 amino acid sequences with the human DJ-1 protein (Nagakubo et al., *Biochem Biophys Res Commun.* 231(2):509-13 (1997)) shows that they are different proteins, although 91% identical (FIG. 1B).

SP22 polypeptides or polynucleotides may be formulated into a vaccine and administered to a subject to induce an immune response (e.g. cellular or humoral) against SP22 in that subject.

Figure 11:
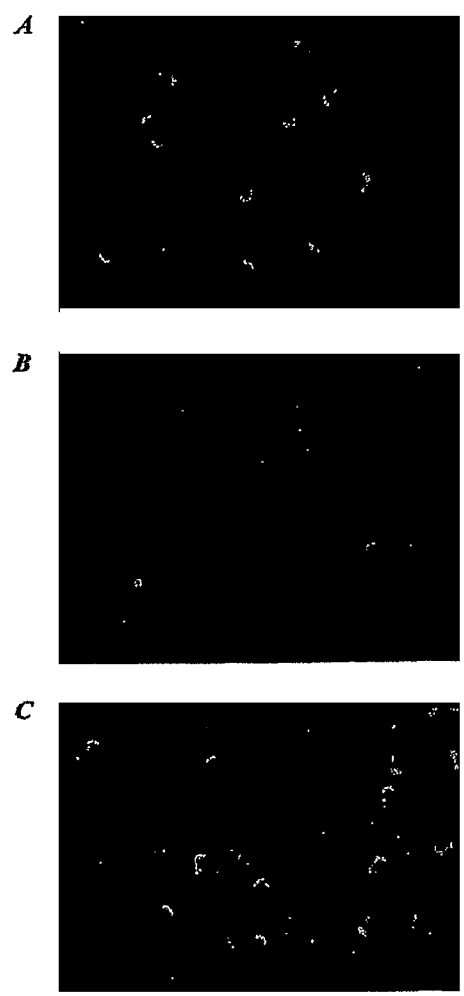
FIG. 11A is a micrograph depicting immunolocalization of SP22 on fresh, unfixed rat cauda epididymal sperm in the presence of anti-SP22 peptide Ig. Anti-SP22 peptide Ig was diluted 1:200 prior to use.
FIG. 11B is a micrograph depicting the immunolocalization of SP22 using anti-SP22 peptide Ig and Peptide A (20 micrograms).
FIG. 11C is a micrograph depicting the immunolocalization of SP22 using anti-SP22 peptide Ig and Peptide B (20 micrograms). Peptide A competes effectively with the Ig to ablate the staining, indicating that Peptide A, but not Peptide B, is an exposed surface peptide.
Figure 12:
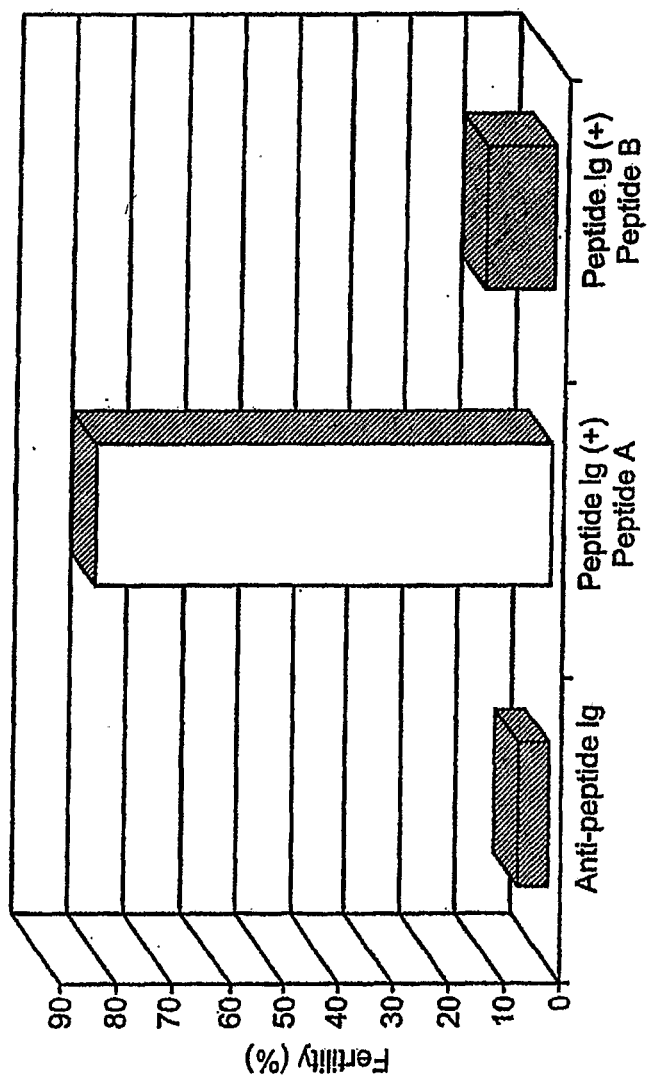
FIG. 12 is a bar graph comparing levels of fertility in rats inseminated with cauda epididymal rat sperm previously incubated with anti-SP22 peptide Ig for five minutes prior to insemination with levels of fertility in rats inseminated with cauda epididymal rat sperm incubated with anti-SP22 peptide Ig and Peptide A (20 micrograms) or Peptide B (20 micrograms). Anti-SP22 peptide Ig was diluted 1:50 prior to use.

A particularly preferred SP22 protein for inclusion in a vaccine is the full length SP22 polypeptide or an SP22 surface peptide, which may be identified, for example, according to the three-tiered analysis described in Example 7. Briefly, functional fragments of the SP22 polypeptide may be identified by: 1) identifying linear epitopes of SP22 via mimotope analysis with an SP22 antibody and via 2) competitive binding experiments using synthetic peptides representing said linear epitopes to ablate immunocytochemical staining and/or to ablate inhibition of fertility when used in combination with SP22 antibody (FIGS. 11 and 12). Peptides corresponding to the epitopes predicted by the mimotope analysis may then be synthesized. The methods described in Examples 7 and 13 may be used to determine if the peptides are exposed. Exemplary SP22 surface peptides include: TVAGLAGKDPVQCSR (SEQ ID NO: 6), GKDPVQCSRDVVICPDTS (SEQ ID NO: 73) LEEAKTQGPYDVVVL (SEQ ID NO: 8), VKEILKEQENRKGLI (SEQ ID NO: 9), QNLSESALVKEILKEQENRKGLI (SEQ ID NO: 74), GFGCK- VTSHPLAKDK (SEQ ID NO: 10), TSFEFALAIVEALSG (SEQ ID NO: 11) and a peptide generated to span multiple surface peptides: SRDVVICPDTSLEEAKTQGPYDVVVLPG-GNLGAQNLSESALVKEILKEQENRKGLI (SEQ ID NO: 12).

Also provided herein are DNA vaccines comprising nucleotide sequences, which encode SP22 peptides. Preferred DNA vaccines encode two or more SP22 surface peptides. The efficacy of candidate vaccines (peptide or DNA) may be tested in appropriate animal models such as rats, mice, guinea pigs, monkeys and baboons. A protective or positive effect of the vaccine should be reflected by reduced fertility in the experimental animals.

Nucleic acids encoding SP22 immunogens may be obtained by polymerase chain reaction (PCR), amplification of gene segments from genomic DNA, cDNA, RNA (e.g. by RT-PCR), or cloned sequences. PCR primers are chosen, based on the known sequences of the genes or cDNA, so that they result in the amplification of relatively unique fragments. Computer programs may be used in the design of primers with required specificity and optimal amplification purposes. See e.g., Oligo version 5.0 (National Biosciences). Factors which apply to the design and selection of primers for amplification are described for example, by Rylchik, W. (1993) "Selection of Primers for Polymerase Chain Reaction." In *Methods in Molecular Biology*, vol. 15, White B. ed., Humana Press, Totowa, N.J. Sequences may be obtained from GenBank or other public sources. Alternatively, the nucleic acids of this invention may also be synthesized by standard methods known in the art, e.g. by use of an automated DNA synthesizer (such synthesizers are commercially available from Biosearch, Applied Biosystems, etc).

Suitable cloning vectors for expressing SP22 polypeptides in a host or in a cell may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, or may carry genes for a marker that can be used in selecting clones containing the vector. Suitable examples include, but are not limited to, plasmids and bacterial viruses, e.g., pUC18, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen. A number of expression vectors suitable for expression in eukaryotic cells including yeast, avian, and mammalian cells are known in the art. One example of an expression vector is pcDNA3 (Invitrogen, San Diego, Calif.), in which transcription is driven by the cytomegalovirus (CMV) early promoter/enhancer. This vector also contains recognition sites for multiple restriction enzymes for insertion of the polynucleotide of interest. Expression vectors for expressing SP22 polynucleotide immunogens in male or female subjects can be, e.g., virus based vectors or appropriate nucleic acid vaccine vectors (plasmids), which are commercially available (e.g., Vical, San Diego, Calif.). Other appropriate vectors and suitable host cells for expressing SP22 polynucleotides and polypeptides are known in the art and need not be described in detail herein. For example, see Gacesa and Ramji (1994) *Vectors*, John Wiley & Sons.

SP22 sequences may be operatively linked to suitable transcriptional controlling elements, such as promoters, enhancers and terminators. For expression (i.e., translation), one or more translational controlling elements are also usually required, such as ribosome binding sites, translation initiation sites, and stop codons. These controlling elements (transcriptional and translational) may be derived from the target protein of interest, or they may be heterologous (i.e., derived from other genes or other organisms). A polynucleotide sequence encoding a signal peptide can also be included to allow the polypeptide to cross or lodge in cell membranes or be secreted from the cell. Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will grow under selective conditions. The choice of the proper marker gene will depend on the host cell, and appropriate genes for different hosts are known in the art. Cloning and expression vectors typically contain a replication system recognized by the host.

Transformation methods which may vary depending on the type of host cell, may include electroporation; transfection employing calcium chloride, rubidium chloride calcium phosphate, DEAE-dextran, or other substances; microprojectile bombardment; lipofection; infection (where the vector is an infectious agent); and other methods. See generally, *Molecular Cloning: A Laboratory Manual*, 2nd Ed., ed. by Sambrook, Fritsch and Maniatis (Cold Spring Harbor Laboratory Press: 1989). Reference to cells into which the nucleic acids described above have been introduced is meant to also include the progeny of such cells.

SP22 immunogens may alternatively be prepared from enzymatic cleavage of intact SP22 polypeptides. Examples of proteolytic enzymes include, but are not limited to, trypsin, chymotrypsin, pepsin, papain, V8 protease, subtilisin, plasmin, and thrombin. Intact polypeptides can be incubated with one or more proteinases simultaneously or sequentially. Alternatively, or in addition, intact SP22 polypeptides can be treated with disulfide reducing agents. Peptides may then be separated from each other by techniques known in the art, including but not limited to, gel filtration chromatography, gel electrophoresis, and reverse-phase HPLC.

4. SP22 Antibodies and Uses Thereof

To produce SP22 antibodies, host animals may be injected with SP22 polypeptides of overlapping sequence across a desired area of the SP22 protein. For example, peptide antigens that are at least 5, 10, 15, 20, 25, 30, 35, 40, 45, 50, 55, 60, 65, 70, 75, 80, 85, 90, 95, 100, 105, 110, 115, 120, 125, 130, 135, 140, 145 or 150 amino acids maybe designed in tandem order of linear amino acid sequence of a protein, or staggered in linear sequence of the protein as described in Example 7. In addition, antibodies to three dimensional epitopes, i.e., non linear epitopes, can also be prepared, based on, e.g., crystallographic data of proteins. Hosts may also be injected with peptides of different lengths encompassing a desired target sequence. Antibodies obtained from that injection may be screened against the short antigens of SP22. Antibodies prepared against an SP22 peptide may be tested for activity against that peptide as well as the full length SP22 protein. Antibodies may have affinities of at least about $10^{-6}$M, $10^{-7}$M, $10^{-8}$M, $10^{-9}$M, $10^{-10}$M, $10^{-11}$M or $10^{-12}$M toward the SP22 peptide and/or the full length SP22 protein. The antibodies may recognize one or multiple functional fragments of SP22.

Suitable cells for the DNA sequences and host cells for antibody expression and secretion can be obtained from a number of sources, including the American Type Culture Collection ("*Catalogue of Cell Lines and Hybridomas*" 5th edition (1985) Rockville, Md., U.S.A.).

Methods of antibody purification are well known in the art. See, for example, Harlow and Lane (1988) *Antibodies: A Laboratory Manual*, Cold Spring Harbor Laboratory, N.Y. Purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-antibody. Antibodies may also be purified. on affinity columns according to methods known in the art.

Antibodies to SP22 may be prepared as described above for diagnostic and contraceptive uses. In other embodiments, antibodies that recognize functional SP22 fragments may also be used in random peptide phage display technology (Eidne et al., *Biol Reprod.* 63(5):1396-402. (2000)). Briefly, fifteen or twelve-mer random peptide phage display libraries can be used to determine what peptides might interact with functional SP22 peptides by competitive displacement of Fab fragments of SP22 antibodies. For this, fixed sperm are allowed to adhere to wells in multiwell plates, and immunostaining for SP22 may then be evaluated in the absence and presence of unique and random peptides expressed by the phage library. Once the competitive peptides are identified by amino acid sequence analysis, increased amounts of peptide can be synthesized and used as alternative molecular antagonists to antibodies directed against functional fragments. Another alternative is to screen small molecule libraries for their ability to competitively displace Fab fragments to functional SP22 fragments. Molecular antagonists identified in this manner may be used to neutralize the effect of antibodies generated by an immune response to the SP22 polypeptide or polynucleotide vaccine.

In a further embodiment, the antibodies to SP22 (whole antibodies or antibody fragments) may be conjugated to a biocompatible material, such as polyethylene glycol molecules (PEG) according to methods well-known to persons of skill in the art to increase the antibody's half-life. See for example, U.S. Pat. No. 6,468,532. Functionalized PEG polymers are available, for example, from Nektar Therapeutics. Commercially available PEG derivatives include, but are not limited to, amino-PEG, PEG amino acid esters, PEG-hydrazide, PEG-thiol, PEG-succinate, carboxymethylated PEG, PEG-propionic acid, PEG amino acids, PEG succinimidyl succinate, PEG succinimidyl propionate, succinimidyl ester of carboxymethylated PEG, succinimidyl carbonate of PEG, succinimidyl esters of amino acid PEGs, PEG-oxycarbonylimidazole, PEG-nitrophenyl carbonate, PEG tresylate, PEG-glycidyl ether, PEG-aldehyde, PEG vinylsulfone, PEG-maleimide, PEG-orthopyridyl-disulfide, heterofunctional PEGs, PEG vinyl derivatives, PEG silanes, and PEG phospholides. The reaction conditions for coupling these PEG derivatives will vary depending on the polypeptide, the desired degree of PEGylation, and the PEG derivative utilized. Some factors involved in the choice of PEG derivatives include: the desired point of attachment (such as lysine or cysteine R-groups), hydrolytic stability and reactivity of the derivatives, stability, toxicity and antigenicity of the linkage, suitability for analysis, etc.

5. Pharmaceutical Formulations

Purified SP22 polypeptides or nucleic acids may be formulated and introduced as a vaccine through oral, intravaginal, intradermal, intramuscular, intraperitoneal, intravenous, subcutaneous, intranasal, and via scarification (scratching through the top layers of skin, e.g., using a bifurcated needle) or any other standard route of immunization. SP22 polypeptides may further be orally delivered as a vaccine by enteric coated capsules which will dissolve in the gut. SP22 will then be taken up by antigen presenting cells in Peyer's patches. Oral delivery of SP22 polypeptides may supplement injections of SP22 polypeptides.

The amount of SP22 immunogens used in a vaccine can depend upon a variety of factors including the route of administration, species, and use of booster administration. In general, doses of about 0.1 to about 100 micrograms per kg of body weight may be used. In a preferred embodiment, the antifertility vaccines of the present invention are to be administered orally. The vaccine may be formulated into tablets, capsules, granules, powders or syrups. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent. In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated composition.

Vaccine formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject composition can be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

SP22 based vaccines may also be administered intravaginally using suppositories. Suitable suppository bases are, for example, natural or synthetic triglycerides, paraffin hydrocarbons, polyethylene glycols or higher alkanols.

Alternatively, SP22 based vaccines may be administered parenterally as injections (intravenous, intramuscular or subcutaneous). The vaccine compositions of the present invention may optionally contain one or more adjuvants. Any suitable adjuvant can be used, such as aluminum hydroxide, aluminum phosphate, plant and animal oils, and the like, with the amount of adjuvant depending on the nature of the particular adjuvant employed. In addition, the antifertility vaccine compositions may also contain at least one stabilizer, such as carbohydrates such as sorbitol, mannitol, starch, sucrose, dextrin, and glucose, as well as proteins such as albumin or casein, and buffers such as alkali metal phosphates and the like. Preferred adjuvants include the SynerVax™ adjuvant.

The vaccine compositions of the invention that are suitable for parenteral administration may be formulated into pharmaceutically-acceptable sterile isotonic aqueous or non-aqueous solutions, dispersions, suspensions or emulsions, or sterile powder which may be reconstituted into sterile injectable solutions or dispersions just prior to use, and may further contain antioxidants, buffers, bacteriostats, solutes (which render the formulation isotonic with the blood of the intended recipient) or suspending or thickening agents. Examples of suitable aqueous and non-aqueous carriers which may be employed in the vaccine compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants. The formulated SP22 vaccine compositions may be stored in a sterile glass container sealed with a rubber stopper through which liquids may be injected and compositions withdrawn by syringe.

In another embodiment of the invention, SP22 antibodies may also be formulated for parenteral administration as described above.

Alternatively, SP22 immunogens or SP22 antibodies of the present invention may be encapsulated in liposomes and administered via injection. Commercially available liposome delivery systems are available from Novavax, Inc. of Rockville, Md., commercially available under the name Novasomes™. These liposomes are specifically formulated for immunogen or antibody delivery. In an embodiment of the invention, Novasomes™ containing SP22 antibody molecules bound to the surface of these non-phospholipid positively charged liposomes may also be formulated into a spermicide.

The SP22 antibody containing spermicide compositions of the invention are preferably colorless, odorless and non-staining. In addition, such SP22 antibody spermicide compositions should preferably cover the vagina/cervix when applied in a liquid state, be compatible with a male latex condom, and be resistant to elution by aqueous flow. Such spermicide compositions should additionally preferably have a pH similar to that of a healthy vagina (pH 4.0-4.5) and should not affect the normal vaginal flora, especially *Lactobacillus* spp. SP22 antibody spermicide compositions of the invention preferably maintain desired rheological properties under extreme heat and cold conditions.

Suitable excipients for SP22 antibodies in spermicide compositions may be lubricants, cleansing agents, deodorizers, humectants, emollients, plasticizers, binders, emulsifying agents, stabilizing agents, solvents, bioabsorbable materials, antioxidants, solubilizing agents, antimicrobial preservatives, diluents, glidants, suspending agents, extended-release agents, coating agents, adsorbents, disintegrants, chelating agents, and mixtures and combinations thereof.

Exemplary non-limiting humectants can be selected from the group consisting of: glycerin, propylene glycol, sorbitol, triacetin, and mixtures thereof.

Exemplary non-limiting emollients can be selected from the group consisting of cetearyl, lanolin, mineral oil, petrolatum, cetyl esters wax, cholesterol, glycerol, glyceryl monostearate, isopropyl myristate, isopropyl palmitate, lecithin, and mixtures thereof.

Exemplary non-limiting binders can be selected from the group consisting of: acacia, alginic acid, carboxymethylcellulose, hydroxyethylcellulose, hydroxypropylcellulose, dextrin, ethylcellulose, gelatin, liquid glucose, hydrogenated vegetable oil, hydroxypropylmethylcellulose, magnesium aluminum silicate, maltodextrin, methylcellulose, polyethylene oxide, polymethacrylates, povidone, sodium alginate, starch, zein, acrylic and methacrylic acid co-polymers, pharmaceutical glaze, gums such as guar gum, and milk derivatives such as whey and starches, as well as other conventional binders well known to persons skilled in the art.

Exemplary non-limiting stabilizing agents can be selected from the group consisting of acacia, albumin, polyvinyl alcohols, alginic acid, bentonite, carboxymethylcellulose, hydroxypropyl cellulose, colloidal silicon dioxide, cyclodextrins, glyceryl monostearate, hydroxypropyl methylcellulose, magnesium aluminum silicate, propylene glycol, propylene glycol alginate, sodium alginate, wax, xanthan gum, and mixtures thereof.

Exemplary non-limiting solvents can be selected from the group consisting of alcohol, benzyl phenylformate, corn oil, cottonseed oil, diethyl phthalate, ethyl oleate, glycerol, glycofurol, isopropyl alcohol, isopropyl myristate, medium-chain triglycerides, mineral oil, peanut oil, polyethylene glycol, propylene carbonate, propylene glycol, sesame oil, soybean oil, triacetin, and mixtures thereof.

Exemplary non-limiting solubilizing agent can be selected from the group consisting of benzalkonium chloride, castor oil, cyclodextrins, polyoxyethylene ethers, glyceryl monostearate, lecithin, poloxamer, polysorbates, polyoxyethylene stearates, sorbitan esters, stearic acid, and mixtures thereof.

Exemplary non-limiting antimicrobial preservatives can be selected from the group consisting of benzoic acid, EDTA, phenolic acid, sorbic acid, benzyl alcohol, isopropyl alcohol, benzethonium chloride, bronopol, butylparaben, cetrimide, chlorhexidine, chlorobutanol, chlorocresol, cresol, ethylparaben, glycerol, imidurea, methylparaben, phenol, phenoxyethanol, phenylmercuric acetate, phenylmercuric borate, phenylmercuric nitrate, potassium sorbate, propylene glycol, propylparaben, sodium benzoate, sodium propionate, sorbic acid, thimerosol, and mixtures thereof.

Exemplary non-limiting diluents can be selected from the group consisting of calcium phosphate, calcium sulfate, carboxymethylcellulose calcium, cellulose, cellulose acetate, dextrates, dextrin, dextrose, fructose, glyceryl palmitostearate, kaolin, lactitol, lactose, magnesium carbonate, magnesium oxide, maltitol, maltodextrin, maltose, microcrystalline cellulose, polymethacrylates, powdered. cellulose, pregelatinized starch, silicified microcrystalline cellulose, sodium chloride, sorbitol, starch, sucrose, sugar, talc, hydrogenated vegetable oil, and mixtures thereof.

Exemplary non-limiting extended-release agents can be selected from the group consisting of carrageenan, cellulose acetate, glyceryl monostearate, zein, and mixtures thereof.

Suitable suppository bases are, for example, natural or synthetic triglycerides, paraffin hydrocarbons, polyethylene glycols or higher alkanols. Foam compositions may include oily suspensions or aqueous solutions of the active ingredient with suitable foaming agents. Other topical carriers for vaginal applications include pharmaceutically acceptable liquids in which the active ingredient is suspended or dissolved.

Spermicides may be formulated with additional active agents, including for example, antifungal agents, antibacterial agents, antimicrobial agents, antiviral agents, spermicides, hormone agents, antitrichomonial agents, antiprotozoan agents, antimycoplasm agents, antiretroviral agents, nucleoside analogues, reverse transcriptase inhibitors, protease inhibitors, other contraceptive agents and environment modifying agents, such as pH modifiers, and mixtures and combinations thereof.

In a preferred embodiment, the antifungal agent is selected from the group consisting of butoconazole nitrate, clotrimazole, ketoconazole nitrate, miconizole, polyene antifungals, nystatin, amphotericin B, pimaricin, oxiconazole nitrate, terconazole nitrate, tioconazole, flutrimazole, intraconizole, allylamines, terbenafine, butenafine, amorolfine, naftifine, gluconazole, azoles, econazole, voriconizole, fluconazole, posaconazole, sulconazole, diction bis-benzimidazoles, glucan synthesis inhibitor, echinacandins, anidulafungin, caspofungin, micafugin, anti-tb drugs, diaphenylsulfone, ciclopirox olamine, haloprogin, tolnatane and undecylenate.

In another preferred embodiment, the antibacterial agent is selected from the group consisting of clindamycin, sulfonamides, erythromycin, clarithromycin, azythromycin, tetracycline, doxacline, metronidazole, macrolides, ketolides, quinolones, cephalosporins, carbapemnens, penicillins, gentamicin, magainin peptides, dalbavancin, ramoplanin, iseganan, cefoxitin, ceftriaxone and trichloroacetic acid.

In yet another preferred embodiment, the antiviral agent is selected from the group consisting of penciclovir, acylovir, ganciclovir, foscarnet, valaciclovir, pleconaril, and mixtures and combinations thereof.

In still another preferred embodiment, the spermicide is nonoxynol-9.

The present invention also provides for SP22 antibody based spermicide compositions to be formulated and administered as mucoadhesive gels, hydrogels, foams, lotions, ointments, jellys, films, vaginal inserts/suppositories, quick dissolving tablets, douches, lubricants, a lubricant on a intravaginal barrier device, or aerosol. As used herein "intravaginal barrier device" refers to vagina rings, male condoms, female condoms, cervical caps, diaphragms, or the like. Devices such as vaginal rings, are further described in U.S. Pat. No. 3,545,439, U.S. Pat. No.3,920,805, U.S. Pat. No. 4,012,496, U.S. Pat. No. 4,012,497, U.S. Pat. No. 4,237,885, U.S. Pat. No. 4,286,587, U.S. Pat. No. 4,292,965. Other embodiments may include applying the spermicide composition in the form of foam, cream, gel, jelly, lubricant, or lotion on the interior and/or exterior surfaces of the device.

Alternatively, the spermicide composition may be administered with an applicator which is a vaginally insertable elongated object adapted to receive and dispense the spermicide composition. In one embodiment, the applicator is a single use tube containing a single dosage of spermicide composition and has an aperture, preferably equipped with a rupturable removable cap, provided at the distal end thereof, i.e. the end to be disposed adjacent to the patient's cervix on full and proper insertion into the vagina. Another form of applicator is equipped with a plunger which can be operated to empty the internal cavity of the tube through the distal end. opening. The tube is filled. with the appropriate dosage of spermicide composition, inserted fully into the vagina, and the plunger is operated to empty it as it is withdrawn. The length of the applicator ensures that an effective amount of the spermicide composition is disposed at the cervical end of the vagina, for maximum protection. Alternatively, the applicator may be a penis.

The SP22 antibody spermicide composition may additionally be impregnated in vaginal sponges and/or tampons. Alternatively, the sponges and/or tampons may comprise microcapsules or liposomes containing SP22 antibodies and provide sustained release of the antibodies before, during and/or after coitus. See U.S. Pat. No. 3,918,452. The sponges or tampons may additionally be impregnated with antibiotics for control of venereal disease. Such tampons may be inserted into the vagina to cover the cervical area while permitting intercourse to take place. See U.S. Pat. No. 4,309,997.

SP22 antibody spermicide compositions may also be incorporated into sexual lubricants which include glycerin (also called glycerine, glycerol, 1,2,3-propanetriol, and trihydroxypropane) and certain types of polyethylene glycol (PEG), such as PEG 200 or PEG 400 (the numbers indicate different molecular weight averages). Various other polymers (such as polypropylene glycol, polyisobutene, and polyoxyethylene) and behenic acid and behenyl alcohol may also be used. In addition, some sugar-alcohols such as sorbitol, and some silicon compounds such as polydimethylsiloxane, are also used as skin-contacting lubricating agents. Because glycerin, propylene glycol, polyethylene glycol, and polypropylene glycol have long been used in sexual lubricants and other skin-contacting compositions with no adverse effects, they are preferred. for use as lubricating agents in the composition of this invention. The suitability of any other candidate lubricating agent can be determined through routine experimentation in humans to ensure that it will not cause irritation or other adverse effects, and in in vitro cell culture and in in vivo lab animal tests.

A suitable thickening agent which is widely used in genital lubricants may be comprise of chemically treated derivatives of cellulose (such as hydroxyethyl- or hydroxymethyl-cellulose). Other thickening agents which have been used in skin-contacting compounds, and which offer candidate agents for potential use in genital lubricant compositions, include acacia, agar, alginate, carrageenan, gum tragacanth, xanthan gum, collagen, carboxypolymethylene, glyceryl monostearate, polyvinylpyrrolidone, and polyacrylamide. Other components, including preservatives (such as DMDM hydantoin, chlorhexidine gluconate), anti-crystallization agents (such as glucono-delta-lactate), fragrances, sweeteners, odorants, coloring agents, alkaline or acidic or buffering agents to maintain the proper pH (such as EDTA), and soothing, anti-swelling agents (such as lanolin, aloe vera extract, or hydrocortisone), antiviral agents (such as zinc salts; see U.S. Pat. No. 5,785, 054), hormones (such as estrogen) or spermicides can be added to the lubricant composition of the invention described herein. However, at the concentrations used, any such additive should not seriously impede the desired activity of the final spermicide composition and should not irritate or have other adverse effects on the genitals.

The complete mixture must be physiologically safe and acceptable when used repeatedly over a period of months or years, and it must not irritate mucous membranes or other genital surfaces. The composition should also be free of anticoagulants (particularly heparin or dextran sulfate) or other components which could pose a risk of adverse effects in a significant portion of the population.

6. Diagnostics

SP22 antibodies may also be used to quantitatively or qualitatively detect the presence of SP22 polypeptides on sperm. For example, labeled SP22 antibodies may be used in fertility diagnostic for testing vasectomized males to determine the success of the surgery and vasovasostomized males to determine the success of surgical reconnection. Further uses of SP22 antibodies include testing livestock for artificial insemination candidates: the higher the levels of SP22 in the potential donor, the more likely artificial insemination is to be successful. The determination of the presence of SP22 on sperm in a biological sample, either an ejaculate or a sample derived from an ejaculate or from the male reproductive tract will determine a subject's fertility.

A diagnostic test for clinical evaluation of an individuals' response to an SP22 based vaccine may be developed. Such a test will measure the titer of anti-SP22 antibodies and can be developed as a clinical diagnostic kit for monitoring fertility status in individuals receiving an SP22 based vaccine. It may also be necessary to monitor the development of antibodies to the SP22 vaccine, i.e. the SP22 polypeptide or the SP22 polynucleotide. Certain subjects may lack a suitable immune response system, and many subjects may vary in the antibody titer generated in response to any antigen or protocol of antigen administration. Development of an adequate antibody titer may be easily confirmed using the SP22 protein as an antigen standard. Achievement of 100 percent binding suggests an adequate antibody titer. A vaccination program may be conducted under clinical supervision using, for example, ELISA, Western blotting analysis or other established immunoassays to monitor antibody titer in a subject undergoing SP22 vaccination.

The amount of SP22 present on the surface of sperm in a sample (epididymal or ejaculate, animal or human) can be determined using quantitative fluorescence spectroscopy or fluorescent light microscopy. For this, sperm may be incubated with SP22 antibody and then with labeled Rhodamine or FITC-conjugated second antibody. It is first necessary to determine the relationship between fluorescence of a sample in a fluorometer or a microscopic image. The optical density of SP22 may be separated by two dimensional gel electrophoresis. Once this is established, fluorescence intensities may be related to fertility. It is also important to determine the relationship between the number of sperm in a sample which express (SP22) and the degree of the expression or fluorescence with fertility. This is particularly true for men considering assisted reproductive technologies. For example, if only a critical number (X) of sperm is needed to express a threshold amount (Y) of SP22 for a successful attempt at fertility, it is possible to selectively remove those sperm not expressing SP22 in the ejaculate and use only those sperm that do express a sufficient amount of SP22 for assisted reproductive technologies such as intra uterine transfer or IVF. This may be achieved with the dissociation of SP22 expressing sperm from the SP22 antibody. For example, polystyrene microwells may first be precoated with SP22 antibody and sperm in the ejaculate may then be allowed to bind. Unbound sperm may be washed away. Antibody-bound sperm may be recovered following dissociation of the antibody with incubation in 0.1 M lithium diiodosalicylate, and increasing numbers of these SP22 expressing sperm may then be inseminated in utero.

Diagnostic assays for SP22 polypeptides typically involve incubating ejaculate or a sample derived from an ejaculate or from the male reproductive tract in the presence of a detectably labeled antibody capable of identifying an SP22 polypeptide and detecting the antibody by any suitable immunoassay including, without limitation, competitive and noncompetitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradio metric assays, fluorescent immuno assays and protein A immuno assays. Such assays may be carried out in the conventional way using a laboratory analyzer or with point of care or home testing device, such as the lateral flow immunoassay as described in EP291 194.

In one embodiment, SP22-specific antibodies can be detectably labeled by linking the antibodies to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactivity labeling the antibodies, it is possible to detect SP22 through the use of a radioimmunoassay (RIA). A good description of RIA maybe found in Laboratory Techniques and Biochemistry in *Molecular Biology* by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a gamma counter or a scintillation counter or by autoradiography.

It is also possible to label an anti-SP22 antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$EU, or others of the lanthanide series. These metals can be attached to the antibody using such metal chelating groups as diethylenetriamine pentaacetic acid (EDTA).

The antibody also can be detectably labeled by coupling it to a chemiluminescent compound. The presence of the chemiluminescent-tagged. antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule may also be adapted for use in a immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen form the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled. antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, the so-called "simultaneous" and "reverse" assays are used. A simultaneous assay involves a single incubation step as the antibody bound to the solid support or carrier and. labeled. antibody are both added. to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

A screening assay may be used to identify the presence of an antibody that is immunologically reactive with an SP22 antigen. Briefly, a biological sample may be obtained from a subject undergoing vaccination. The sample may then be incubated with a solid support containing bound recombinant SP22 proteins. Finally, the antibody-antigen complex may be detected by conventional means. The term "solid support" is intended to include any support or carrier capable of binding SP22 antigen. Well-known supports or carriers, include glass, polystyrene, polypropylene, polyethylene, dextran, nylon amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen. Thus, the support or carrier configuration may be spherical, as in a bead, or cylindrical, as in the inside surface of a test tube, or the external surface of a rod. Alternatively, the surface may be flat such as a sheet, test strip, etc. Preferred supports or carriers include polystyrene beads. Those skilled in the art will know many other suitable carriers for binding SP22 antigen, or will be able to ascertain the same by use of routine experimentation. Suitable methods and reagents for detecting an antibody-antigen complex in assays of the present invention are commercially available or known in the relevant art.

Diagnostic assays to determine the amount of SP22 on the surface of sperm may be combined with assays that evaluate sperm motility. In one embodiment, the assay selects for a subset of motile sperm from the total sperm population and then determines if the motile sperm subset expresses SP22 on its surface. The subset of motile sperm separated from the sperm sample has an average motility higher than an average motility of sperm from the sperm sample. Thus, combining an assessment of sperm motility with a determination of the amount of SP22 on the surface of sperm may be used to determine the subpopulation or subset of motile sperm that are capable of fertilization providing a more accurate measurement of fertility.

7. Kits

The invention also provides kits for detecting SP22 and SP22 antibodies. The kits of the invention may be used as over-the-counter home test kits. In one embodiment, a kit may comprise one or more reagents for detecting SP22 on sperm in a sperm sample, e.g., an ejaculate, a sample derived from an ejaculate, or a sample from the male reproductive tract. The one or more reagents may comprise an antibody that is immunospecific for SP22 or a fragment thereof. The kit may further comprise one or more reagents (i.e., an antibody) for measuring the level of a second marker indicative of fertility.

In one embodiment, a kit to detect the level of SP22 on sperm may comprise an application zone and a detection zone. The application zone and the detection zone may be contained in a cup-like device for performing the detection reaction. The cup-like device may comprise an application zone, e.g., a first reservoir for the addition of a sperm sample and a detection zone, e.g., a second reservoir comprising a buffer containing an SP22 antibody. The application zone and detection zone may be positioned adjacent to one another and the application zone may be positioned above the detection zone or side-by-side to the detection zone. The kit may optionally contain a cover for the application zone and/or the detection zone, e.g., a first or second reservoir.

The application zone and the detection zone may be separated by a barrier zone. Viable sperm capable of motility may move from the application zone to the detection zone by passing through the barrier zone. The barrier zone may comprise a barrier filter or a chamber.

When the barrier zone comprises a barrier filter, the barrier filter must be porous to allow motile sperm to permeate the barrier-filter. The barrier filter may comprise a nylon mesh filter. The nylon mesh barrier filter may be 5-10 µm, 10-20 µm, 20-30 µm, 30-40 µm, 40-50 µm, 50-60 µm, 60-70 µm, 70-80 µm, 80-90 µm, or 90-100 µm. In one embodiment, the nylon mesh barrier filter is 75 µm. Mesh porosity is ultimately dependent on two factors: 1) the species from which the sperm are evaluated, and 2) the stringency of the motility that one wishes to select for.

A person skilled in the art will appreciate that a barrier filter may comprise pores or apertures derived from substances or materials other than nylon.

In other embodiments, the barrier zone may comprise a chamber. The chamber may be elongate, e.g., in the form of a channel, to separate motile sperm that can swim the length of the chamber from non-motile sperm that cannot swim the length of the chamber. The chamber may comprise obstacles or internal walls, wherein only the motile sperm would be able to navigate the obstacles or internal walls to reach the detection zone. Further, the barrier zone may comprise a chamber that comprises any combination of being elongate with obstacles or internal walls.

In certain embodiments, it may be desirable to determine if SP22 is present on the entire sperm population (i.e., motile and non-motile sperm). In such instances, a more porous barrier may be used to allow sperm to cross the barrier zone by both active and passive diffusion. For example, if the entire sperm population is being tested for the presence of SP22, a cup-like device comprising a single reservoir may be used. A single reservoir may be coated with SP22 antibodies.

The kit may further comprise one or more ports attached to the detection zone. The port may be pre-filled with solution or filled prior to use of the kit with solution. E.g., the port may comprise a diluting buffer and/or a substrate that may be added to the detection zone. A port may also be used to exchange solutions in the detection zone. A port may be separated from the detection zone by a filter. In an exemplary embodiment, a filter separating a port from the detection zone allows solution to be added and/or removed from the reservoir, but does not allow sperm to pass through the filter. The filter may be 0.1-0.5 µm, 0.5-1.0 µm, 1.0-1.5 µm, 1.5-2.0 µm, 2.0-2.5 µm or 2.5-3.0 µm. In one embodiment, the filter separating a port from the detection zone is 0.2 µm. If two or more ports are present, they may be filled with the same or different solutions. Further, one port may be used to add solutions to the detection zone and a second port to remove solution from detection zone. Alternatively, both ports may be used to add or remove solution from the detection zone.

The detection zone into which motile sperm swim may be coated with an SP22 antibody that recognizes at least one SP22 peptide exposed on the sperm surface. The SP22 antibody may recognize a single or multiple exposed SP22 peptides. The SP22 antibody may be chemically activatable such that upon binding of SP22 exposed on the sperm surface a chemical reaction occurs which elicits a color signal. This allows for direct detection of SP22 in the sample. Alternatively, following addition of a sperm sample, motile sperm swim into the detection zone containing a labeled (e.g., peroxidase) antibody. After SP22 antibody binds SP22 exposed on the sperm, excess labeled antibody is removed and reactive substrate (e.g., DAB) binds to the SP22 antibody. The colored reaction product indicates the amount of SP22 exposed on the sperm surface. Detectable markers may include, e.g., a chemiluminescent, enzymatic, fluorescent, dye, or radioactive moiety. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by a calorimetric method, which employ a chromogenic substrate for the enzyme.

The method to detect the presence of SP22 on a sperm sample may comprise the steps of 1) liquifying the sperm sample in an application zone, wherein the viable sperm swim into a detection zone coated with a chemically activatable SP22 antibody; 2) binding SP22 present on the sperm to the SP22 antibody; and 3) dispensing a chromogenic substrate into the detection zone and monitoring a color reaction.

In further embodiments, a kit for detecting SP22 in a sperm sample may still further comprise instructions or a color-coded scale for visual evaluation. A color reaction in the detection zone, e.g., a second (or single) reservoir, indicates the presence of SP22 in the sperm sample. The detection of a color reaction may provide a positive or negative reading of SP22 in the sperm sample. In certain embodiments, the amount of SP22 may be proportional to the intensity of the color reaction and compared against a color scale. Alternatively, a color reaction may be read using a spectrophotometer or an ELISA reader.

In another embodiment, a kit to detect the level of SP22 on sperm may comprise a lateral flow device, e.g., such as the device disclosed in EP291194. In a lateral flow device, such as the one disclosed in EP291194, the device may comprise a hollow casing constructed of moisture-impervious solid material containing a dry porous carrier, which communicates directly or indirectly with the exterior of the casing such that a liquid test sample can be applied to the porous carrier. The device also comprises a labeled specific binding reagent for an analyte which labeled specific binding reagent is freely mobile within the porous carrier (or first zone of the device) when in the moist state, and unlabelled specific binding reagent for the same analyte which unlabelled reagent is permanently immobilized in a detection zone (or second zone of the device) on the carrier material and is therefore not mobile in the moist state, the relative positioning of the labeled reagent and detection zone being such that liquid sample applied to the device can pick up labeled reagent and thereafter permeate into the detection zone, and the device incorporating means enabling the extent (if any) to which the labeled reagent becomes in the detection zone to be observed.

In an exemplary embodiment, SP22 antibody that recognizes at least one exposed SP22 peptide may conjugated to a detectable marker that may be present in first zone of the lateral flow device. Unlabeled substrate (e.g., DAB) may be immobilized in a second zone of the lateral flow device. Upon addition of a sperm containing sample to the lateral flow device, at least one exposed SP22 peptide on the sperm bind the conjugated SP22 antibody in the first zone of the device, permeate into the detection zone, and bind the unlabeled substrate immobilized in the detection zone (second zone) of the device producing a colored reaction product. Alternatively, a direct label (e.g., colloidal gold) may be conjugated to the SP22 antibody This can be used to produce an instant analytical result without the need to add further reagents to develop a detectable signal. Detectable labels that may be used in a lateral flow device include, but are not limited to, gold sols and dye sols, which are robust and stable and can therefore be used readily in an analytical device which is stored in the dry state. Their release on contact with an aqueous sample can be modulated, for example by the use of soluble glazes.

Another kit of the invention may detect vaginal SP22 antibodies. Said kit may comprise a device for collecting a vaginal sample and a monitoring device comprising SP22 conjugated to a detectable marker, e.g., a chemiluminescent, enzymatic, fluorescent, dye, or radioactive moiety. The kit may further comprise a device for storing the vaginal sample. The kit may additionally comprise one or more reagents for measuring the level of a second marker indicative of fertility.

In one embodiment, the device for collecting a vaginal sample may comprise a polyurethane or polyester (e.g., Dacron) swab (on a polystyrene or polypropylene plastic shaft). The swab should be inserted preferably 6 cm (3 cm to 9 cm) deep from the opening of the vagina and rotated several times for at least 10 seconds before removal.

In another embodiment, the device for collecting a vaginal sample may comprise a tampon or a tampon-like device, wherein vaginal fluid can be collected or absorbed and removed from the vagina. A tampon-like device may comprise a tubular body comprising a plunger slidably housed inside the tubular body and having an absorptive material for collecting a vaginal sample on the distal end.

In one embodiment, the monitoring device comprises a cup-like device containing a reservoir coated with chemically activatable SP22. The reservoir may be pre-filled or filled prior to use of the kit with a buffer for performing the reaction. Alternatively, the reservoir may be uncoated and filled with a solution comprising chemically-activatable SP22. The cup-like device may further comprise one or more ports for adding and/or removing solution to the reservoir as described above. Further, one or more ports may be separated from a reservoir by a filter as described above.

In certain embodiments, the one or more ports may contain buffer comprising a substrate, e.g., a chromogenic substrate like DAB. The port may be used to add substrate to the reservoir following addition of the vaginal sample to the reservoir coated with SP22 and filled with conjugated antibody against the Fc fragment of the SP22 antibodies in the sample (e.g., peroxidase conjugated anti-human Ig, Fc specific).

The cup-like device may additionally comprise a cover. Further, a kit for detecting SP22 antibodies in a vaginal sample may comprise instructions or a color-coded scale for visual evaluation.

In an exemplary embodiment, a vaginal sample is collected and added to the cup-like device containing a reservoir coated with unlabeled SP22. Unlabeled SP22 is coated on the reservoir, and labeled antibody that recognizes the Fc fragment of the anti-SP22 Ig is added to the reservoir prior to the addition of vaginal sample. Unlabeled SP22 will complex SP22 antibody and the labeled Fc specific antibody will in turn bind to the SP22 antibody. Unbound antibody is then removed from the reservoir and chromogenic substrate (e.g., DAB) is added to the reservoir, e.g., through a port. A color reaction in the reservoir indicates the presence of SP22 antibodies in the vaginal sample. The detection of a color reaction may provide a positive or negative reading of SP22 antibodies in the vaginal sample. In certain embodiments, the amount of SP22 antibodies may be proportional to the intensity of the color reaction and compared against a color scale. Alternatively, a color reaction may be read using a spectrophotometer or an ELISA reader.

In another embodiment, the monitoring device comprising SP22 is a lateral flow device, e.g., such as the device disclosed in EP291194. In a lateral flow device, such as the one disclosed in EP291194 and described above, SP22 conjugated to a detectable marker (e.g. peroxidase) may be present in first zone of the lateral flow device. Peroxidase substrate may be immobilized in a second zone of the lateral flow device. Upon addition of the vaginal sample to the lateral flow device, SP22 antibodies present in the sample bind the conjugated SP22 in the first zone of the device, permeate into the detection zone, bind to peroxidase substrate (e.g., DAB) immobilized in the detection zone (second zone) of the device, and a colored reaction product occurs. If a direct label (e.g., colloidal gold) is conjugated to SP22 in the first zone, it can be used to produce an instant analytical result after permeation into the second zone without the need to add further reagents to develop a detectable signal. Direct labels that may be used in a lateral flow device include, but are not limited to, gold sols and dye sols, which are robust and stable and can therefore be used readily in an analytical device which is stored in the dry state. Their release on contact with an aqueous sample can be modulated, for example by the use of soluble glazes.

A kit of the invention may additionally comprise one or more of the following: (1) instructions for using the kit for detecting the presence of SP22; (2) a label or insert indicating regulatory approval for diagnostic, prognostic, or therapeutic use or any combination thereof.

All publications and patents mentioned herein are hereby incorporated by reference in their entirety as if each individual publication or patent was specifically and individually indicated to be incorporated by reference. In case of conflict, the present application, including any definitions herein, will control.

Exemplification

The invention, having been generally described, may be more readily understood by reference to the following examples, which are included merely for purposes of illustration of certain aspects and embodiments of the present invention, and are not intended to limit the invention in any way.

EXAMPLE 1

Identification and Cloning of SP22

Cauda epididymal sperm extracts were prepared as described previously (Klinefelter et al., *J Androl.* 18(2):139-50 (1997)) using 80 mM n-octyl-beta-glucopyranoside (OBG) in 10 mM Tris, pH 7.2, to which 0.2 mM phenylmethylsulfonyl fluoride was freshly added. The extract was then concentrated, desalted, and assayed for protein prior to HPLC separation. Fractions highly enriched in SP22 were obtained by reverse phase C4 HPLC using a linear gradient of 20-80% acetonitrile in water with 0.1% trifluoroacetic acid (TFA). SP22-containing fractions were pooled and aliquots equivalent to 60 µg of protein were loaded for separation on two dimensional 14% SDS-PAGE. Gels were then stained with Coomassie Blue and the SP22 spots punched out and frozen for use in subsequent peptide sequencing.

Isolated SP22 protein was then subjected to tryptic digestion, and the resulting peptide mixture was separated by HPLC. Peaks representing homogeneous peptides were selected for sequence determination by Edman degradation, and the resulting peptide sequences were matched against NCBI GenBank protein sequences using the BLAST program.

The partial amino acids identified for SP22 were substantially homologous with human DJ-1 (Nagakubo et al., *Biochem Biophys Res Commun.* 231(2):509-13 (1997)). A rat testis cDNA library (Stratagene, LaJolla, Calif.) was then screened with an EST cDNA (Accession No. AA388672) encoding a mouse DJ-1 gene. The mouse DJ-1 cDNA probe was prepared by random primer labeling with [$^{32}$P]-dCTP (Amersham, Arlington Heights, Ill.) using a Prime-It 11 kit (Stratagene). Library screening and bacteriophage isolation was carried out using the method of Benton and Davis, *Science.* 196(4286):180-2 (1977).

SP22 insert DNA was sequenced using the dideoxynucleotide termination method of Sanger et al., *Proc Natl Acad Sci USA.* 74(12):5463-7 (1977), using the SequiTherm Excel Kit (Epicenter Technologies, Madison, Wis.). Sequence data were assembled using the MacVector analysis package (Oxford Molecular Products, Oxford, England).

To evaluate the tissue specificity of SP22, total RNA was isolated from multiple reproductive and somatic tissues. Northern blotting to 10 µg total RNA was performed as described by Welch et al., *Biol Reprod.* 46(5):869-78 (1992), with a stringent wash at 60 degree C. and an exposure time of 20 hours.

Results

The nucleotide and amino acid sequences of SP22 are represented in FIG. 1A. Four peptide sequences were obtained from peptide sequencing as shown in FIG. 1B. Each peptide was relatively short in length and each was flanked by trypsin cleavage sites at Lys (K) or Arg (R). Peptides #1, 2, and 4 matched sequences in the DJ-1 protein recently described in human HeLa cells (Nagakubo et al., *Biochem Biophys Res Commun.* 231(2):509-13 (1997)). Moreover, five of the seven amino acids contained within peptide #3 following Edman degradation matched the DJ-1 sequence. Of the two amino acids in peptide #3 which did not match DJ-1 sequence, one is now known to be erroneous (i.e., G should be H), and the other represents a T (human DJ-1) to S (rat SP22) substitution in the DNA sequence (FIG. 1B). The 3' untranslated region of the SP22 cDNAs contained a typical polyadenylation signal (AATAAA), although separate sites of polyadenylation were observed. Comparisons of human DJ-1 with expressed sequence tagged cloned from mouse indicated that these peptides were also perfectly conserved between human and mouse. Database searches using the SP22 sequence indicated a substantial homology (91% identity) with the human DJ-1 protein (FIG. 1B) and suggest that SP22 and DJ-1 are members of the same protein family.

Sequencing of SP22 cDNAs obtained from a rat testis cDNA library further indicated that SP22 was encoded by two distinct mRNA sequences with divergent 5' sequences (FIG. 2). The presence of SP22 sequences with divergent 5' ends was not unexpected. Northern blotting of rat tissue (testis, epididymis, brain, liver and kidney) RNAs, detected a 1 kB mRNA in all tissues and an additional 1.5 kB transcript found only in the testis. While a specific tissue or cell type has not been assigned to each sequence at this time, the unique 5' untranslated region of SP22 shows some similarity to the 5' untranslated region of mouse somatic expressed tag sequences homologous with rat SP22. Similarly, the longer 5' untranslated regions of SP22A, shown in FIG. 2, suggested that those sequences encode the 1.5 kB mRNA. This unique untranslated sequence may serve to impart mRNA stability for the subsequent expression of SP22 in the testis. Northern blotting with sequence specific probes is needed to relate the different SP22 sequences to their respective mRNAs and to their relative tissue abundance.

EXAMPLE 2

Recombinant SP22 Protein

A recombinant SP22 expression cassette encoding the entire SP22 protein was synthesized by PCR amplification of the coding region from the SP22 cDNA. This cassette was cloned into a pQE8 plasmid containing a prokaryotic lac promoter region and the Shine-Delgado ribosome binding site to facilitate expression in *E. coli*. The plasmid also contained a sequence encoding a series of six histidine residues (6×His) to allow rapid purification of the recombinant protein. Once transfected into *E. coli*, SP22 production was induced by the addition of isopropyl-thio-beta-D-galactopyranoside (IPTG) to activate the lac promoter. The 6×His tag has a pH-dependent high affinity for nickel and is capable of binding in the presence of high concentration of urea and guanidinium salts.

After growth in culture for 5-6 hours, cells were harvested by centrifugation and solubilized in 6M guanidine hydrochloride, 100 mM phosphate at pH 8.0. The nickel agarose column was washed stepwise in 8M urea, 100 mM phosphate butter at pH 8.0, pH 6.3, pH 5.9, and finally pH 4.5. The bacterial proteins were either not retained on the column or were eluted in the first three washes, while recombinant SP22 (rSP22) was eluted at pH 4.5. The purified rSP22 yields for one liter of bacterial culture were in the milligram range.

EXAMPLE 3

Purification of Native SP22 Protein

A detergent extract of cauda epididymal sperm was chromatographed by reverse-phase HPLC and fractions enriched in SP22 were run in analytical two dimensional gels. Coomassie-stained SP22 punches were subsequently subjected to electroelution and electroeluted material was desalted, concentrated, and assayed for protein.

EXAMPLE 4

SP22 Antibodies

A. Preparation of Monoclonal Antibodies Against Full Length SP22

BALB/c mice were immunized initially via intraperitoneal injections with 50 µg of full length recombinant SP22 and later boosted similarly with native SP22. Services were provided by BioCon, Inc. (Rockville, Md.). Specifically, the mice were immunized with SP22 adjuvant emulsion described above. Each mouse first received 0.2 mL of this emulsion intraperitoneally, and then was reinjected in similar fashion with 0.1 mL six weeks later. Mouse serum was obtained then days after the second injection and then tested for anti-HRP activity via ELISA. The mouse which had serum that exhibited the highest possible anti-HRP activity was chosen for cell fusion. Spleens were collected and cell suspensions were prepared by perfusion with Dulbecco's Modified Eagle Medium (DMEM).

Spleen cell suspension containing B-lymphocytes and macrophages was prepared by perfusion of the spleen. The cell suspension was washed and collected by centrifugation; myeloma cells were also washed in this manner. Live cells were counted and the cells placed into a 37 degree C. water bath. One mL of 50% polyethylene glycol (PEG) was added slowly to DMEM. The BLAB/c spleen cells were fused with SP 2/0-Ag 14 mouse myeloma cells by PEG and the resultant hybridomas were grown in hypoxanthine (H), aminopterin (A) and thymidine (T) (HAT) selected tissue culture media plus 20% fetal calf serum. The surviving cells were allowed to grow to confluence. The spent culture medium was checked for antibody titer, specificity, and affinity. The cells were incubated in the PEG for one to 1.5 minutes at 37 degree C., after which the PEG was diluted by the slow addition of DMEM media. The cells were pelleted and 35 to 40 mL of DMEM containing 10% fetal bovine serum was added. The cells were then dispensed into tissue culture plates and incubated overnight in a 37 degree C., 5% $CO_2$, humidified incubator.

The next day, DMEM-FCS containing hypoxanthine (H), aminopterin (A) and thymidine (T) medium (HAT medium) was added to each well. The concentration of HAT in the medium to be added was twice the final concentration required, i.e., $H_{final}$=1 times $10^{-4}$M $A_{final}$=4 times $10^{-7}$M, and $T_{final}$=1.6 times $10^{-5}$M.

Subsequently, the plates were incubated with HAT medium every three to four days for two weeks. Fused cells were then grown in DMEM-FCS containing HAT medium. As cell growth became ½ to ¾ confluent on the bottom of the wells, supernatant tissue culture fluid was taken and tested for SP22 specific antibody by ELISA. Positive wells were cloned by limiting dilution over macrophage or thymocyte feeder plates, and cultured in DMEM-FCS. Cloned wells were tested and recloned three times before a statistically significant monoclonal antibody was obtained. Spent culture media from the chosen clone contained antibody which binds SP22 in all dilutions tested.

B. Preparation of Polyclonal Antibodies Against Full Length SP22

Unconjugated purified recombinant SP22 (rSP22) was used as an antigen to immunize two four year old Border Leicester Merino sheep (service provided by Chrion Mimotopes, Clayton Victoria, Australia). Briefly, 1 mg of rSP22 was resuspended in 1 ml of phosphate buffered saline and emulsified with an equal volume of Complete Freund's Adjuvant and approximately 1 ml (half of the total volume) was injected into each sheep intramuscularly. A second and third immunization followed two and three weeks later, using Incomplete Freund's Adjuvant. Sera was tested using enzyme-linked immunosorbent assay (ELISA) to determine rSP22-specific antibody titer. Anti-rSP22 containing sera that exhibited high titer based on ELISA results was purified by affinity chromatography on a Sepharose column conjugated with 25 mg of rSP22. Anti-rSP22 Ig was later tested for the ability to inhibit fertility in in utero and in vitro fertilization experiments.

C. Preparation of Polyclonal Antibodies Against SP22 Peptides

Peptides #1 (VTVAGLAGKDPVQCSR) and #4 (DG-LILTSR) (FIG. 1B) obtained. by Edman degradation were used together as antigens to generate polyclonal antibodies in sheep. For this, each peptide was synthesized and conjugated to carrier protein. The peptide conjugates were then used to immunize two four year old female Broder Leicester Merino Sheep (service provided by Chiron Technologies, Raleigh, N.C.). Specifically, each conjugate was emulsified in 1 ml of Freund's complete adjuvant (approximately 0.3 mg each peptide) followed by intramuscular injection. Similar injections were administered two and six weeks later using Freund's incomplete adjuvant. Serum was collected two weeks after the final injection.

Peptides #1 and #4 (2 mg each) were also coupled to CNBr-activated Sepharose and used for affinity purification of anti-SP22 peptide antibody. Briefly, 10 ml of immune serum was mixed with 1 ml peptide-linked Thiopropyl-Sepharose 6B overnight at 4 degree C. Bound anti-SP22 peptide IgG was eluted with 0.1 M glycine-HCl, pH 2.5. IgG was subsequently neutralized, desalted, concentrated, and assayed.

Affinity-purified anti-SP22 peptide antibody (2 mg/ml) was used to immunolocalize SP22 in two dimensional gels. For immunoblotting, sperm proteins in sperm extracts were first resolved by mini-two dimensional gel electrophoresis, and subsequently transferred onto PVDF membranes. The blotted membranes were incubated for one hour at 34 degree C. in Dulbecco's Phosphate Buffered Saline (DPBS) with 1% BSA containing 10% normal rabbit scrum. Next, affinity purified anti-SP22 peptide IgG (1:1000) was added and blots were allowed to shake overnight at 4 degree C. Biotinylated rabbit anti-sheep IgG and ABC reagents were added as per Vectastain instructions and the peroxides reaction product was visualized using the VIP substrate kit. To control for nonspecific binding, pre-immune serum was used in place of the affinity-purified anti-SP22 peptide IgG.

Results

Affinity-purified anti-SP22 peptide recognized SP22 in the detergent extract of cauda epididymal sperm, solubilized membranes isolated from cauda epididymal sperm, and a detergent extract of sperm recovered from the rat testis 18 hours after efferent duct ligation (FIG. 3A). No signal was detected. on blots incubated with preimmune serum.

Figure 3B:
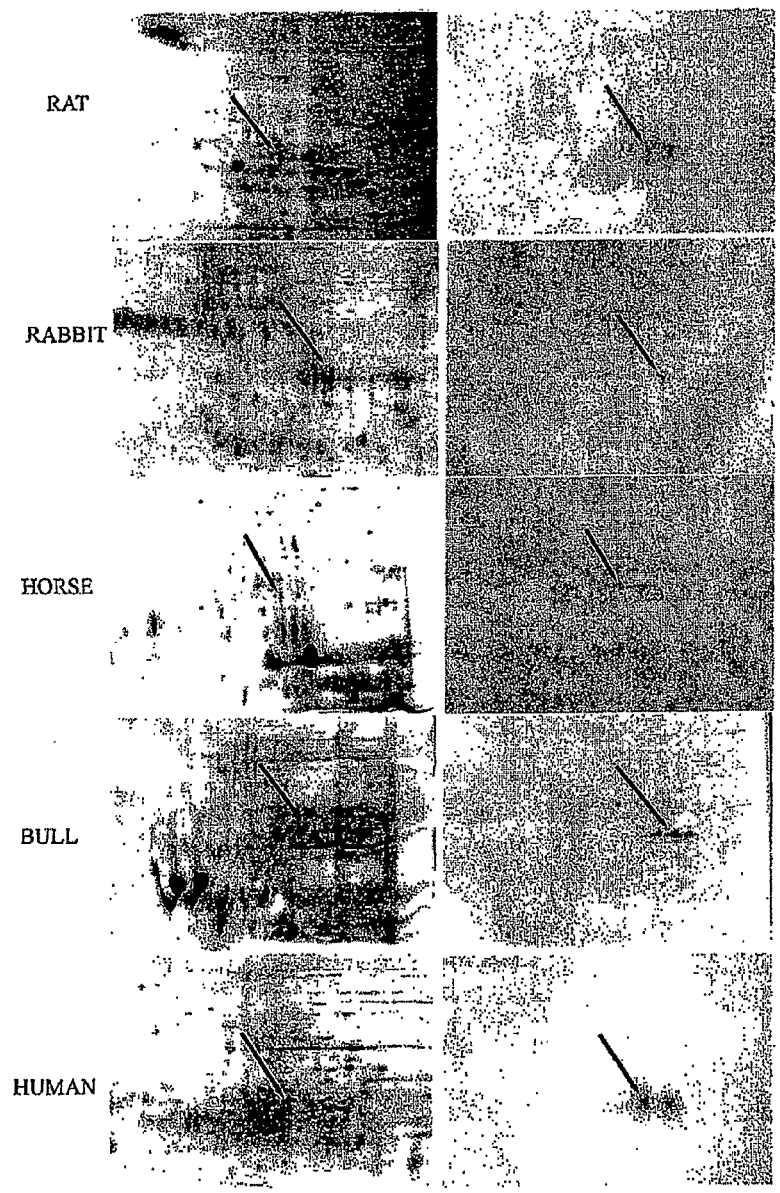
FIG. 3B shows silver stained two dimensional gels and corresponding immunoblots showing the immunolocalization of SP22 in detergent extracts of sperm from rat, rabbit, horse, bull and human. SP22 was localized with anti-SP22 peptide Ig.

The fact that a slightly more basic protein at the same apparent molecular weight was also recognized by the affinity-purified anti-SP22 peptide suggests that post-translationally modified variants of SP22 exist. When affinity-purified anti-SP22 peptide was used to probe immunoblots of detergent extracts of bull, rabbit, stallion, and human sperm a pattern of immunorecognition identical to that seen for the rat was evident (FIG. 3B), suggesting that SP22 and its isoform(s) are present in the sperm membrane regardless of species.

EXAMPLE 5

Correlation Between SP22 Protein Levels and Fertility

It is known that sperm proteins are affected by toxicants and pollutants. In Klinefelter et al., *J. Androl.* 18(2):139-50 (1997), it was demonstrated that endocrine-disruptive chemicals decreased the fertilizing ability of cauda epidiymal sperm. Experiments were then performed to determine if this infertility was related to decrease of SP22 sperm protein levels.

Adult (90 to 120 day old) male Sprague-Dawley rats were housed two to three per cage with laboratory-grade pine shavings as bedding. The rats were maintained under controlled temperature (22° C.) and humidity (40-50%) conditions, and were given Purina laboratory rat chow and tap water ad libitum. Males were maintained in a 14-hour light, 10-hour dark schedule. Each male was numbered and randomly assigned to a treatment group. The test toxicant was administered either as a single intraperitoneal injection or as four daily injections. After four days, the rats were killed, and the caudal epididymis of each rat was placed in a 35-mm culture dish containing 2 mL of Medium 199. Detergent extracts representing 10-40 times $10^6$ sperm, depending on the experiment, were prepared and aliquots equivalent to 30 micrograms were electrophoresed in a mini, two-dimensional electrophoresis system (Bio-Rad) for quantitative analysis of SP22. Specifically, sperm extracts were prepared by first transferring sperm to a microcentrifuge tube. The sperm was then washed twice by centrifugation (300×g, five minutes) in Dulbecco's phosphate buffered saline, pH 7.2, with freshly added 0.2 mM phenylmethylsulfonyl fluoride (PMSF). After the final wash, the sperm was extracted for one hour at room temperature with 1 mL of 80 mM extracted n-octyl-B-glucopyranoside in 10 ml Tris, pH 7.2 and PMSF. Following a final centrifugation at 3000×g, the supernatant was removed and frozen at −70 degree C.

Upon thawing, each extract was concentrated and further extracted in a Tris buffer by two centrifugations (3000×g for 45 minutes at 4 degree C.) in Centricon-10 units (Amicon). Protein concentration was determined using a Pierce protein assay kit. Sample volumes containing 30 microgram protein were lyophilized, and protein was solubilized for 30 minutes at room temperature in 45 µL of sample buffer consisting of 5.7 g urea, 4 mL 10% NP-40, 0.5 mL ampholytes (3-10) and 0.1 g dithiothreitol per 10 mL. Isoelectric focusing (750 V, 3.5 hours) was conducted in gels consisting of 6.24 g urea, 1.5 g acrylamide (30% acrylamide, 1.2% bisacrylamide), 2.25 mL 10% NO-40, and 0.65 mL ampholytes (3-10) per 10 mL. Molecular weight separation was conducted in 11% methanol and silver stained. A Kepler two dimensional gel analysis system (Large Scale Biology Corp., Rockville, Md.) was used for background correlations, spot matching, and spot area quantitation. Images were acquired by transmittance at 80 µm spatial resolution and 4096 gray levels on an Ektron 1412 scanner and converted to 256 gray levels. Quantitation was done by fitting two-dimensional Gaussian distributions to the density distribution of the spot area following background subtraction.

It has been determined that insemination (in utero) of 5 times $10^6$ epididymal sperm from a control rat results in approximately 75% fertility, thereby providing relatively greater sensitivity than insemination of a number of sperm that would result in 100% fertility.

The various data (fertility and SP22, as well as other endpoints such as motility parameters and testosterone concentrations) was collected and analyzed using two-way analysis of variance for both black and treatment effects. An initial analysis was performed to determine whether experimental block differences influenced the parameters measured. Where overall block effects are significant ($p<0.05$), the least-square means were compared for significant ($p<0.05$) treatment differences. A correlation analysis was performed to determine whether significant ($p<0.01$) correlations exist between each of the measured endpoints, and fertilizing ability and Pearson correlation coefficients (R) were calculated.

In a subsequent study, the insemination procedure was modified to permit assessment of fertility (implants/corpora lutea) rather than fertilizing ability (percentage of eggs fertilized). In this study, multiple chemicals that disrupted endocrine status were tested. Adult males were exposed either to 25 or 50 mg/kg of Ethane dimethanesulphonate (EDS), 3 or 6 mg/kg of epichlorohydrin, or 12.5 or 25.0 mg/kg of hydroflutamide or 12.5 or 18.75 mg/kg of chloroethylmethanesulfonate. Each of these compounds perturbs the endocrine balance of the male reproductive system. The animals exposed to the known antiandrogen hydroyflutamide, were castrated and implanted with testosterone implants just prior to the first injection. The vehicle controls for all treatments except hydroxyflutamide treatment experiments received daily injections of 30% DMSO in water. The vehicle controls for the hydroxyflutamide animals were castrated, implanted with testosterone implants, and given daily injection of 15% ethanol.

Four days after the onset of dosing, the males were killed and the epididymides were removed. The caput-corpus was frozen on dry ice for subsequent steroid extraction and testosterone assay. Sperm were released from the epididymal tubule into insemination medium and placed in the $CO_2$ incubator at 34 degree C. for no more than 15 minutes until insemination. Adult, estrus-synchronized female rats were monitored for lordosis behavior just after lights out on the day of insemination. Females displaying mating behavior were cervically stimulated with vasectomized teaser males at least 15 minutes prior to insemination. A volume equal to 5 times $10^6$ sperm was inseminated into each uterine horn at day 0. On day 9, the females were killed and fertility was assessed.

The discovery that SP22 originates in the testis prompted another study in which animals were exposed for 14 days to a testicular toxicant, bromochloroacetic acid. Bromochloroacetic acid is a by-product of drinking water disinfection, currently being investigated by the U.S. Environmental Protection Agency. Previous studies on dibromoacetic acid (Linder et al., *Fundam Appl Toxicol.* 28(1):9-170 (1995); Linder et al., *Reprod Toxicol.* 11(1):47-56 (1997)) and dichloroacetic acid (Linder et al., *Reprod Toxicol.* 11(5):681-8 (1997)) revealed that di-substituted haloacetic acids perturbed spermatogenesis, and that within fourteen days, defects (i.e., alterations in sperm motion and morphology) manifested in epididymal sperm. Therefore, it was hypothesized that bromochloroacetic acid would act similarly.

SP22 levels on sperm were not evaluated in early haloacetic acid studies. Both a quantitative evaluation of SP22 in extracts of epididymal sperm and fertility following in utero insemination was incorporated in a study of bromochloroacetic acid.

Bromochloroacetic acid (BCA) was administered to adult male rats in water by gavage in graded doses, i.e., 0, 8, 24, and 72 mg/kg body weight. The rats were dosed daily for fourteen days. On day fifteen, sperm from the proximal cauda epididymis were prepared for artificial insemination. The sperm remaining after insemination were washed and extracted with 80 mM n-octyl-beta-glucopyranoside (OBG) in 10 mM Tris, pH 7.2. The extract was then concentrated, desalted, and protein concentration was determined prior to separation on 14% mini, two-dimensional SDS-PAGE gels. The silver-stained SP22 protein was background corrected and the integrated optical density was correlated with the fertility of these sperm.

Results

Of the 125 proteins (spots) that were identified in the 50 gel data set, 22 were common to gels representative of sperm extracts of vehicle-treated animals. Of these 22 proteins, only SP22 was affected by all test chemicals in a dose-related fashion. In fact, SP22 was the only one, of the 124 that were identified, that changed in either a dose or treatment-related fashion.

Measurements of sperm motion and sperm morphology were not significantly affected by any of the treatments. Based on scatter plot of the data relating the amount of SP22 to fertility (frequent), fertility classes greater and less than n=50% were chosen. Variables were then entered into the discriminant analyst to predict fertility by class, as shown in Table 1. Since, in this study, fertility for the control animals was targeted at 68%+/− a standard deviation of 18%; 50% represented a reasonable cutoff for the fertile class.

TABLE 1

Discrimination Analysis Based on SP22

| CLASS | PERCENTAGE CORRECTLY PREDICTED |
|---|---|
| Fertile (>50%) | 90 (17/19) |
| Subfertile (<50%) | 94 (29/31) |

A regression analysis showed that the amount of SP22 was significantly correlated to fertility ($p<0.0001$; $r^2$−0.83). A nonlinear fit of the data was indicated, since a threshold of 10,000 integrated optical density units of SP22 was necessary to achieve greater than 50% fertility.

Thus, by entering the level of SP22 of a sperm sample into an appropriate mathematical model, it is possible to predict the fertility of the sperm sample with a reasonably high degree (i.e., p>90%) of success. An antibody to SP22 can be used to evaluate the fertility of sperm in an epididymal sperm sample or an ejaculate. Since the antibody to SP22 recognizes a single protein on immunoblots of cells of both human and stallion sperm extracts, this antibody will most likely be applicable to evaluation of animals in which maximum fertility is important, e.g., cattle, horses, dogs, and humans among other animals.

It was observed that SP22 levels were diminished in detergent extracts of epididymal sperm in a dose-related manner. Significant diminished levels of SP22 was achieved at even the lowest dosage. The fertility of sperm from the treated rats was also significantly decreased and this was highly correlated ($r^2$=0.90) with the SP22 levels.

Figure 5:
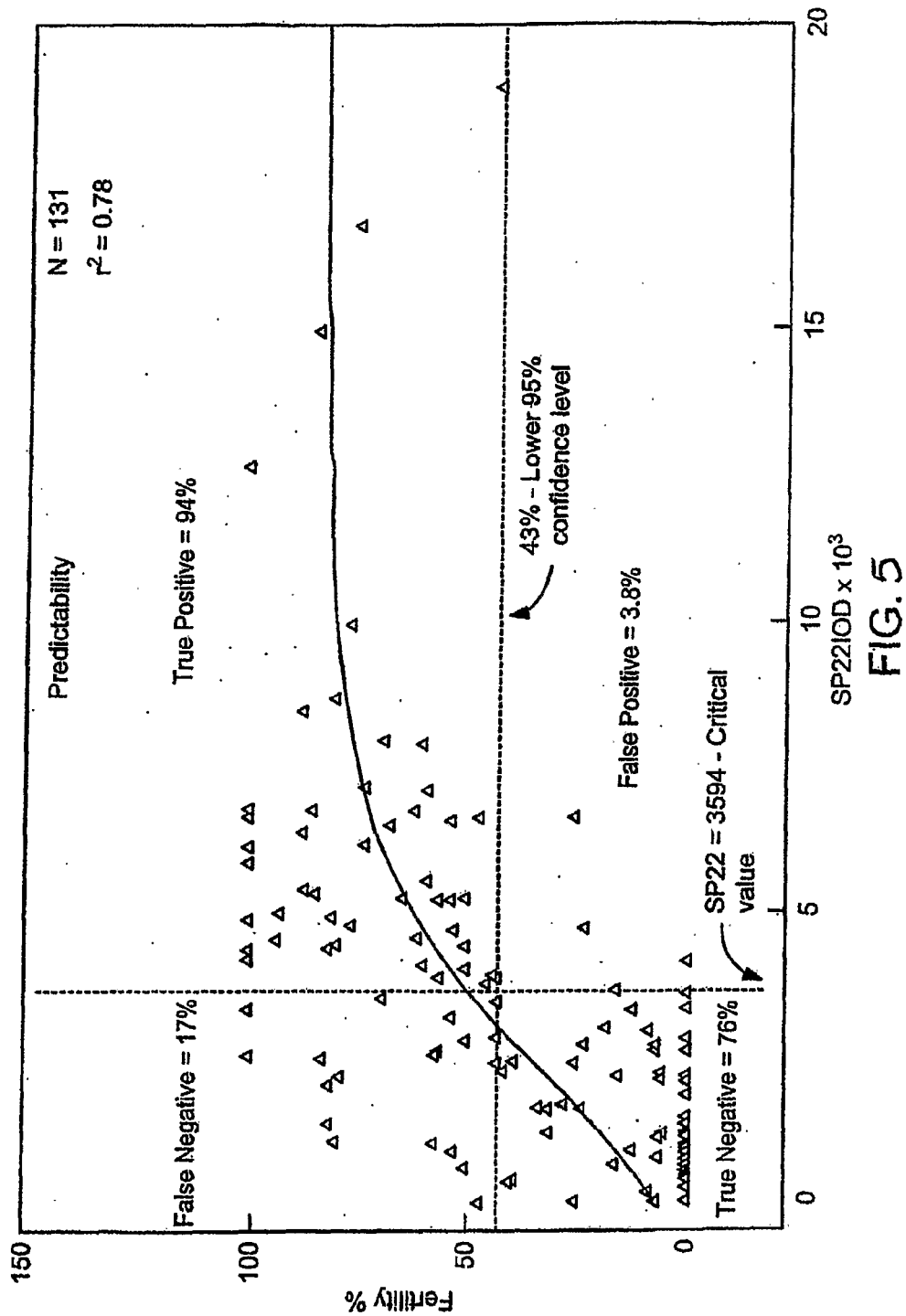
FIG. 5 is a graph demonstrating the correlation between SP22 protein levels and fertility. The data represented in this graph was pooled from a total of 131 animals exposed to either testicular toxicants or epididymal toxicants.

To date, four epididymal toxicants and two testicular toxicants have been evaluated with respect to their ability to compromise both SP22 expression on sperm and the fertility of these sperm. It is clear from FIG. 4 that the relationship between SP22 levels and fertility is similar, i.e., non-linear and threshold-like, and the correlation between these endpoints is quite high. From a diagnostic perspective these data are meaningful only if both the overall correlation and predictability values are good. FIG. 5 represents all data from the 131 animals studied to date following either testicular or epididymal insults. It is clear that the correlation remains quite high ($r^2$=0.78), but more importantly, the predictive value of SP22 can be evaluated as follows: (1) establish a threshold value for the background-corrected, integrated optimal density of SP22 based on the point on the predicted line with the smallest 95% confidence interval (i.e., the least error); the threshold value for SP22 is 3594 at this point; and (2) establish a threshold for fertility at the lower 95% confidence interval at this point; the value for fertility is 43% at this point. Using these criteria, the true positive rate is 94% and the false positive rate is only 3.8%.

Thus, it has now successfully been demonstrated that SP22 levels on epididymal sperm are compromised by chemicals which compromise both testicular and epididymal function. These results established the feasibility of an SP22-based assay of epididymal and ejaculated sperm as a diagnostic indicator of compromised sperm quality, i.e., fertility, in either toxicological or epidemiological settings. Additionally, the existence of SP22 on ejaculated sperm from multiple species (i.e., bull, stallion, human) (FIG. 3) established the feasibility of using such an SP22-based diagnostic to evaluate the fertility of sperm from these species when artificial breeding, herd sires, and assisted reproductive technologies (in vitro fertilization vs. in utero insemination) are considered. This is also of particular importance in breeding endangered species. The toxicants tested above do perturb the endocrine balance of the male reproductive system. Other environmentally relevant endocrine disruptors, such as dioxin, could also compromise the expression of SP22. The present invention thus includes a screening kit to test such chemicals.

EXAMPLE 6

Modulation of Fertility with SP22 Antibodies

Artificial (in utero) insemination in the rat was conducted as previously described (Klinefelter et al., *J. Androl.* 18(2): 139-50 (1997)). Briefly, 10 times $10^6$ cauda epididymal sperm were incubated for five minutes at 34 degree C. either with or without 10 μl of the affinity-purified anti-SP22 peptide (1:50), and 5 times $10^6$ incubated epididymal sperm were injected into each uterine horn of LHRH-synchronized, cervically-stimulated adult females while under halothane anesthesia. Nine days later, the inseminated females were sacrificed and the number of implants and corpora lutea were enumerated. Fertility was expressed as the number of implants relative to the number of corpora lutea.

For in utero inseminations, 10 microliters (equivalent to 60 micrograms) of anti-recombinant SP22 Ig (1:50) was incubated with rat cauda epididymal sperm for five minutes prior to insemination. Fertility was assessed in vivo on day 9 of gestation by the number of fetal implants relative to the number of corpora lutea. For in vitro fertilization, a similar antibody concentration was incubated with cauda epididymal sperm in the presence of eggs overnight. Fertilization was assessed in vitro by the percentage of eggs containing a sperm tail the next morning. In addition the relative number of sperm binding to the zona after insemination was evaluated.

Results

Figure 6:
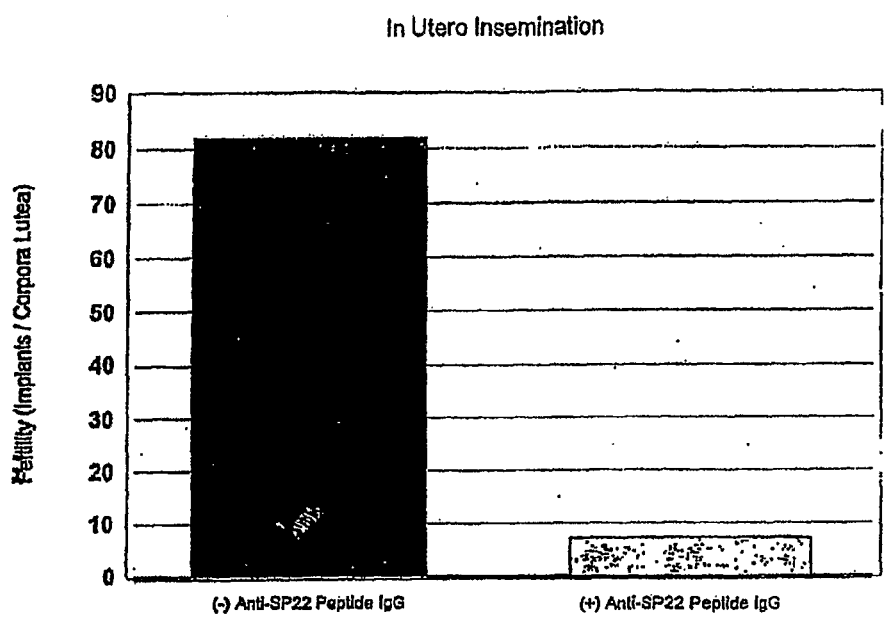
FIG. 6 is a bar graph showing fertility levels in rats inseminated with sperm previously incubated with or without affinity-purified anti-SP22 peptide Ig. Fertility level is expressed as the number of fetal implants relative to the number of corpora lutea on day 9 of gestation. Female rats inseminated with rat cauda epididymal sperm that were not incubated with anti-peptide Ig had a 83% fertility level. Female rats inseminated with sperm that were incubated for five minutes with 10 microliters of affinity purified anti-SP22 peptide Ig prior to insemination in utero, had a 7% fertility level (only one of six females had fetal implants). Anti-SP22 peptide Ig was diluted 1:50 prior to use.

When cauda epididymal sperm was incubated for five minutes with anti-SP22 peptide antibody (1:50) prior to insemination into the uterine horns of receptive females, fertility was significantly reduced (FIG. 6). Indeed, while fertility of sperm that was not incubated with antibody averaged 83% (ranging from 64 to 100%), only one of the six females inseminated with sperm that were incubated with antibody had any implants. The fertility of this one female was below normal (44%).

Figure 7:
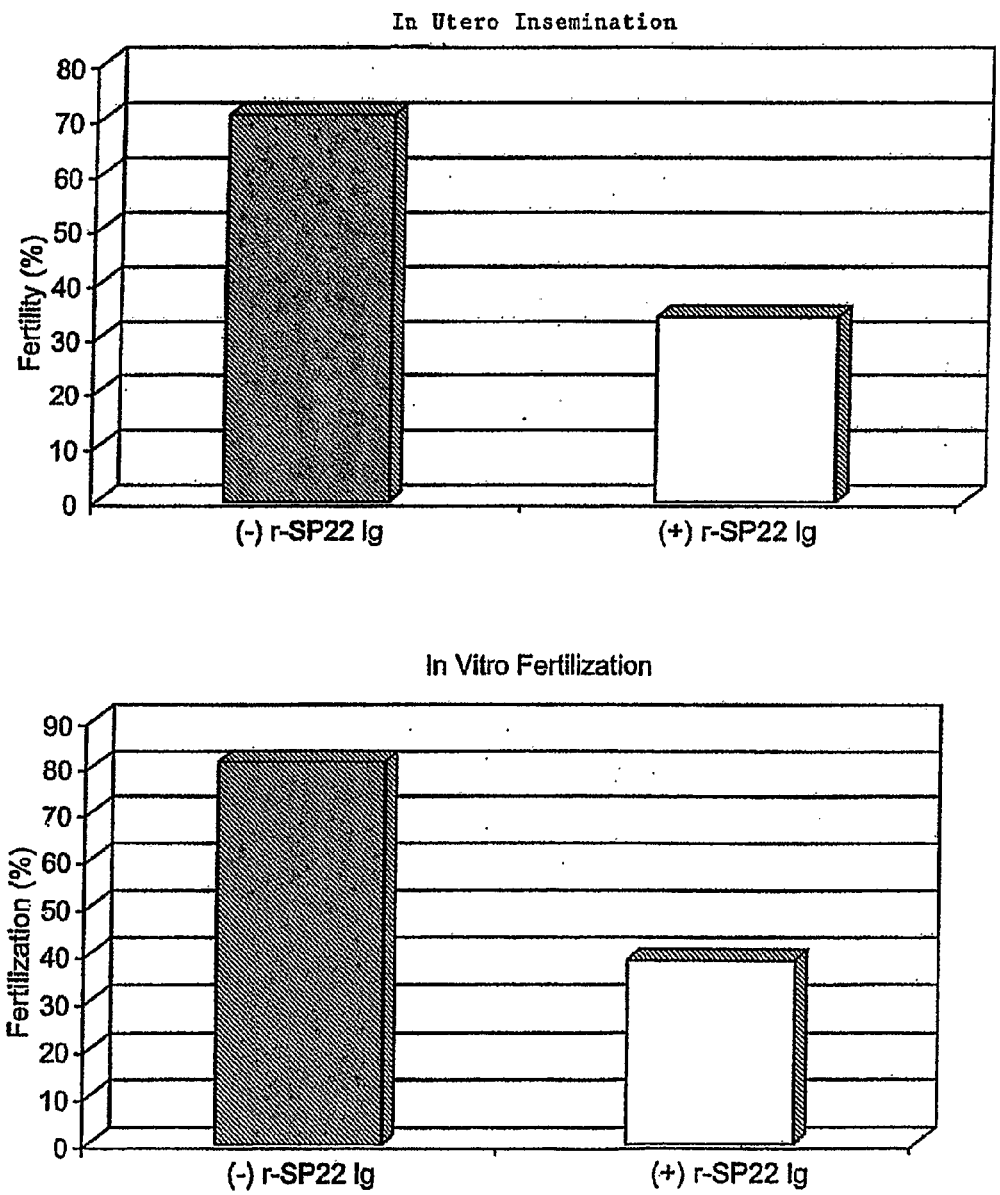
FIG. 7 provides bar graphs showing fertility levels of in utero insemination (top) experiments using rats inseminated with cauda epididymal sperm. previously incubated with the presence or absence of affinity-purified anti-recombinant SP22 Ig and in vitro (bottom) fertilization experiments using rat eggs incubated with cauda epididymal sperm previously incubated in the presence or absence of affinity-purified anti-recombinant SP22 Ig. Anti-recombinant SP22 Ig was diluted 1:50 prior to use.

Similar results were obtained when cauda epididymal sperm was incubated for five minutes with anti-recombinant SP22 antibody (1:50) prior to insemination into the uterine horns of receptive females. Fertility of sperm incubated with the antibody was reduced to 34% whereas fertility of sperm not incubated with the antibody averaged 71% (FIG. 7). In in vitro experiments, 80% of the eggs were fertilized when only sperm was incubated overnight with the eggs. In contrast, only 39% of the eggs were fertilized when sperm was incubated in the presence of anti-recombinant SP22 antibody (FIG. 7). A significant reduction in the number of sperm binding to the zona pellucida of the egg was also observed in experiments where sperm was previously incubated with antibodies.

EXAMPLE 7

Identification of SP22 Functional Fragments for Use as Antigens for Contraceptive Antibodies or as Antifertility Vaccines For the mimotope analysis of SP22 polypeptide, the 189 amino acids comprising SP22 were subdivided into 59 overlapping 15 amino acid peptides, with each peptide overlapping by three amino acids. The 59 peptides were biotinylated and allowed to bind to streptavidin-coated wells in 96-well plates. The reactivity of various antisera was detected by enzyme-linked immunosorbent assay (ELISA). Briefly, after blocking non-specific binding, SP22 antibody was added sequentially (i.e., either affinity-purified anti-SP22 peptide or affinity-purified anti-full-length recombinant SP22), followed by the sequential addition of peroxidase-conjugated secondary antibody, and peroxidase substrate.

Figure 8:
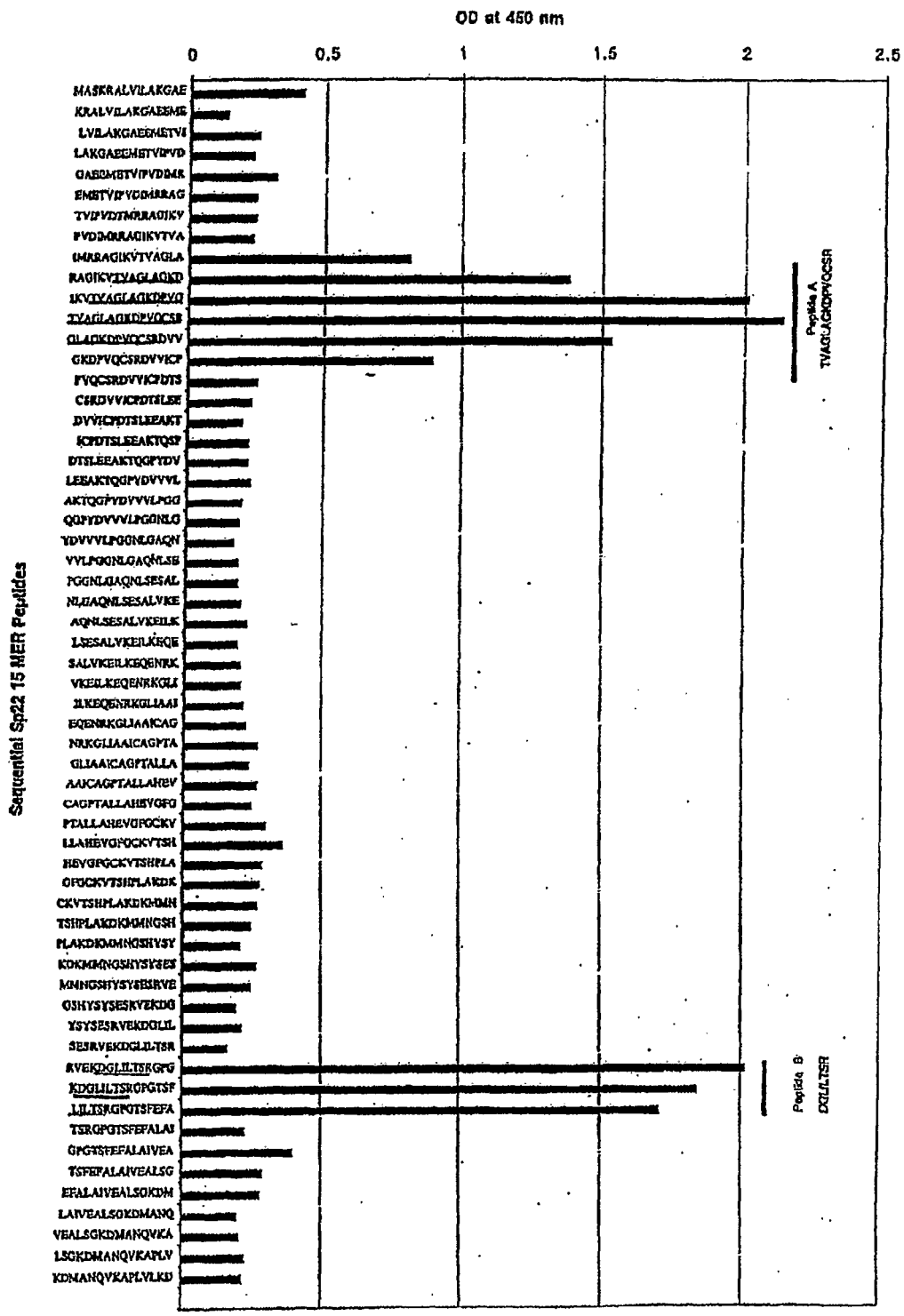
FIG. 8 is a bar graph illustrating the immunoreactivity of overlapping 15 mer SP22 peptides with affinity-purified anti-SP22 peptide Ig. Antiserum was affinity-purified and diluted 1:100 prior to use. The two reactive peaks within the 189 amino acid SP22 sequence are: Peptide A (TVAGLAGKD-PVQCSR) (SEQ ID NO: 6) and Peptide B (DGLILTSR) (SEQ ID NO: 7).
Figure 13:
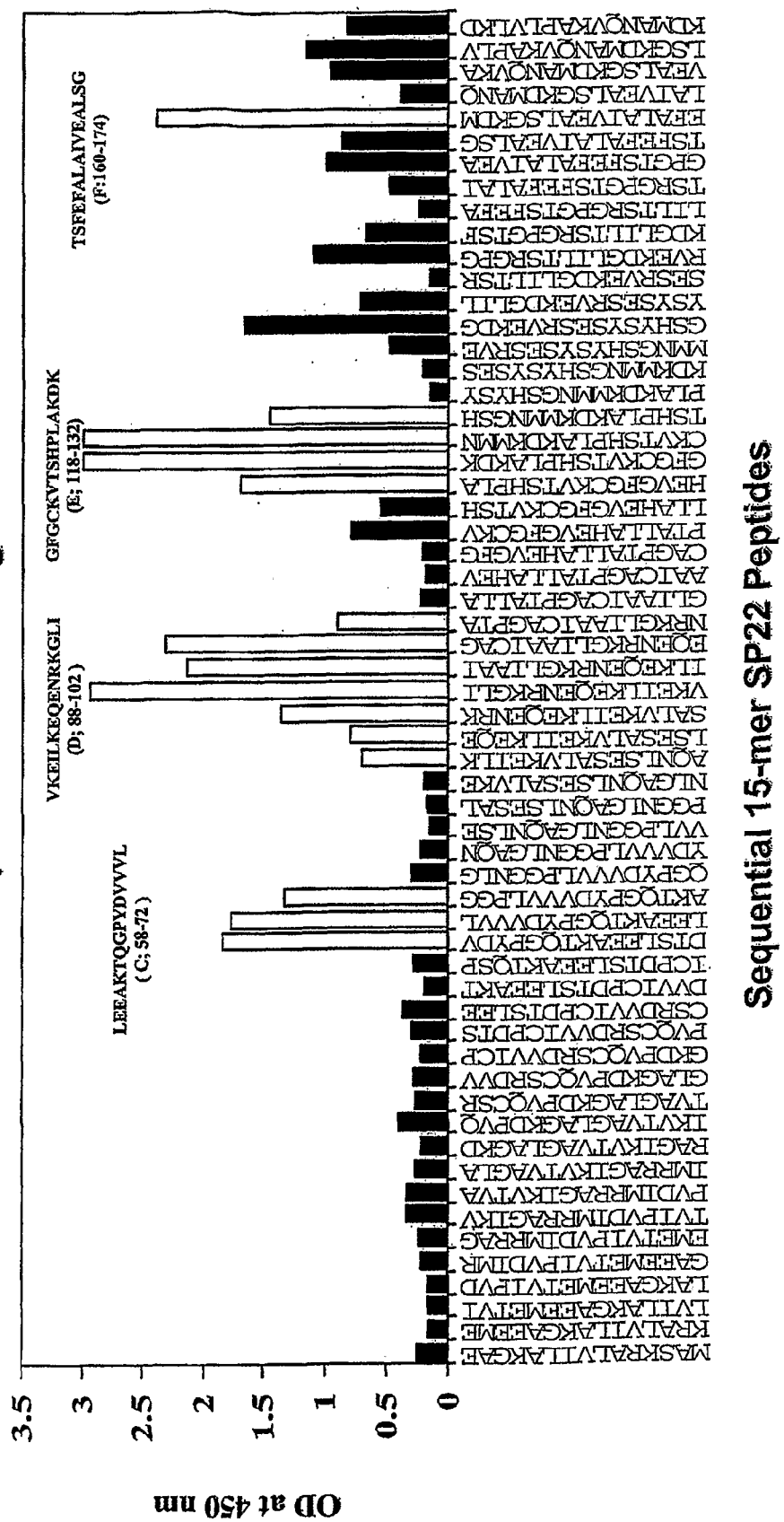
FIG. 13A-B is a bar graph illustrating the immunoreactivity of overlapping 15 mer SP22 peptides with sheep anti-rSP22 Ig (A) and with an Fab preparation of sheep anti-rSP22 (B).
FIG. 13C is a bar graph showing fertility levels of in vitro fertilization experiments using zona-intact hamster eggs incubated in vitro with sperm previously incubated with anti-rSP22 Ig Fab preparation. The additional incubation of peptides C (LEEAKTQGPYDVVVL) (SEQ ID NO: 8), D (VKEILKEQENRKGLI) (SEQ ID NO: 9), and E (GFGCK-VTSHPLAKDK) (SEQ ID NO: 10) with anti-rSP22 Fab preparation and hamster sperm partially alleviates the inhibition in fertilization of hamster eggs.
Figure 13:
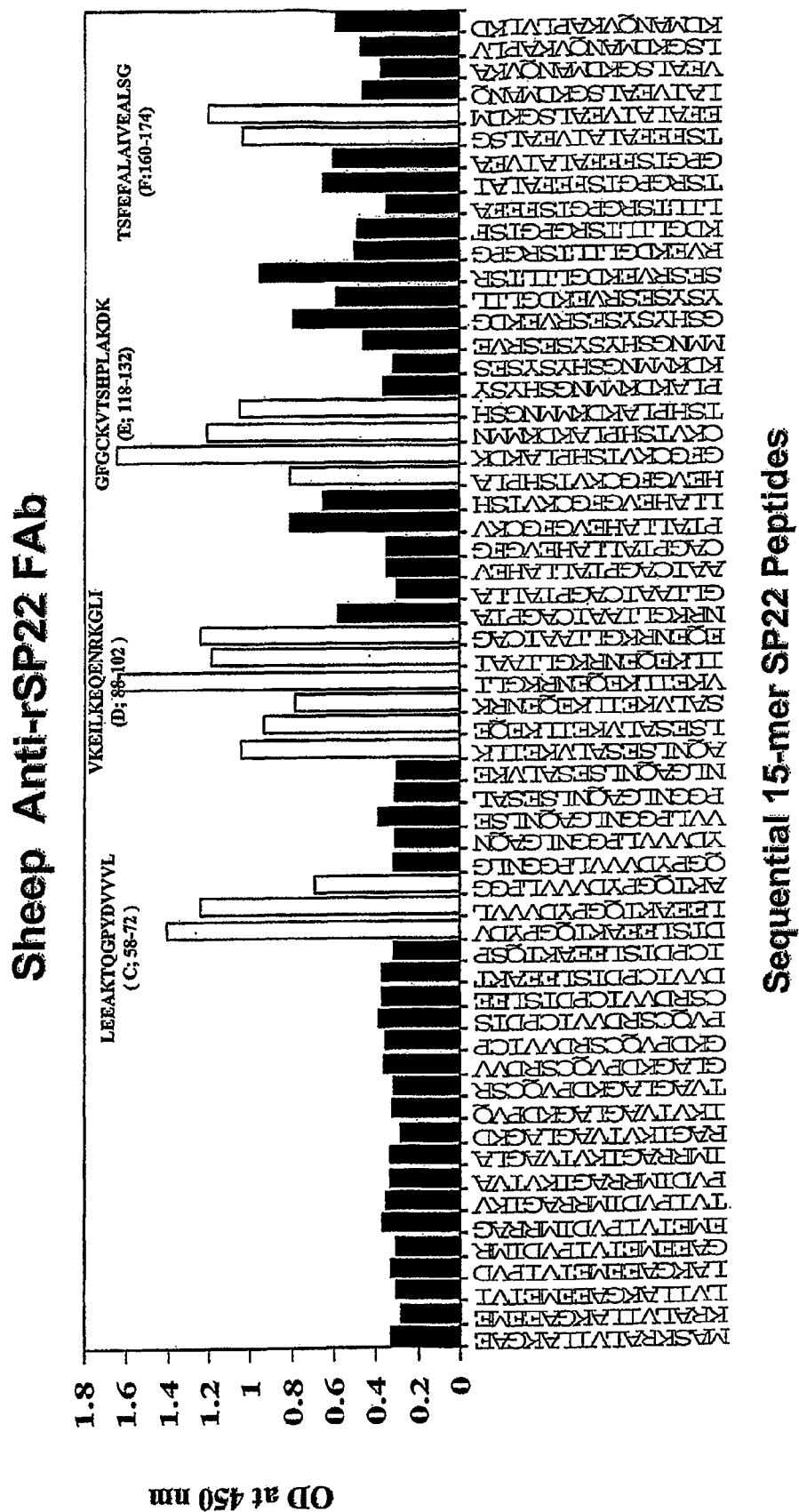

The optical density of each well was read at 450 nm and duplicate wells were averaged. The average value obtained from a similar ELISA using control serum (i.e., preimmune serum) was subtracted from the test Ig values and the resultant values were plotted to determine which linear epitopes were recognized by the Ig (see FIGS. 8 and 13, which represent the mimotope analysis for the anti-SP22 peptide Ig and recombinant SP22 Ig, respectively).

The second and third components in the strategy to identify functional fragments of SP22 relied on the synthesis of non-biotinylated peptides corresponding to the epitopes (peptides) predicted by the mimotope analysis. To determine whether any of the epitopes recognized by mimotope analysis are exposed. on the surface of the sperm membrane, immunocytochemical staining with the Ig, without and with each of the peptides, was performed.

Briefly, cauda epididymal (rat) or ejaculated sperm (bull, human) was washed twice with Dulbecco's Phosphate Buffered Saline (DPBS) and either fixed in Zamboni's fixative containing 0.1% Triton X-100 for one hour at 4 degree C. or incubated directly in blocking buffer (DPBS containing 1% BSA and 10% normal rabbit serum) for one hour at 34 degree C. Fixed sperm was incubated. in blocking buffer after fixation. Blocking buffer was removed after centrifugation and 10 times $10^6$ sperm were incubated in 1 ml of Dulbecco's Phosphate Buffered Saline (DPBS) containing 20 μg of affinity-purified anti-SP22 peptide (1:100) for one hour. After washing, FITC-labeled rabbit anti-sheep (1:25) was added for one hour. Sperm were washed again and mounted using anti-fade mounting medium. The specificity of immunostaining was verified by adding a 20 μg mixture of peptides #1 (10 μg) and #4 (10 μg) (equivalent to Peptide A and B respectively) in conjunction with the affinity-purified. anti-SP22 peptide.

Results

Figure 9:
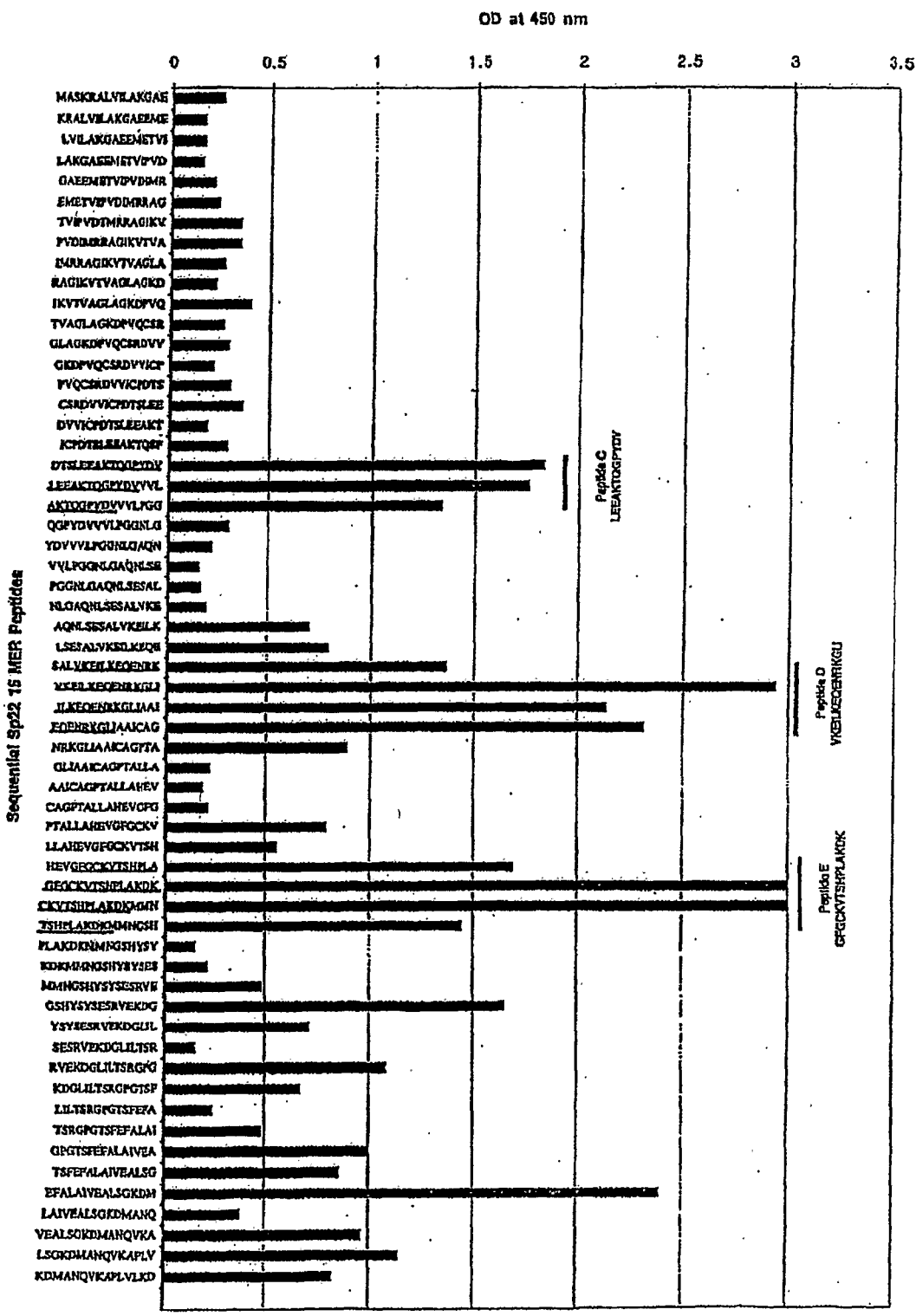
FIG. 9 is a bar graph illustrating the immunoreactivity of overlapping 15 mer SP22 peptides with affinity-purified anti-recombinant SP22 Ig. Antiserum was affinity-purified and diluted 1:100 prior to use. The four reactive peaks within the 189 amino acid SP22 sequence are: Peptide C (LEEAKTQG-PYDVVVL) (SEQ ID NO: 8), Peptide D (VKEILKEQEN-RKGLI) (SEQ ID NO: 9), Peptide E (GFGCKVTSH-PLAKDK) (SEQ ID NO: 10) and Peptide F (TSFEFALAIVEALSG) (SEQ ID NO: 11).

The mimotope analysis of the anti-SP22 peptide (shown in FIG. 8) revealed two peptide epitopes: Peptide A (TVAGLAGKDPVQCSR) and Peptide B (DGLILTSR). The mimotope analysis of anti-recombinant SP22 antibody (shown in FIG. 9) revealed three peptide epitopes: Peptide C (LEEAKTQGPYDV), Peptide D (VKEILKEQENRKGLI), and Peptide E (GFGCKVTSHPLAKDK).

Figure 10:
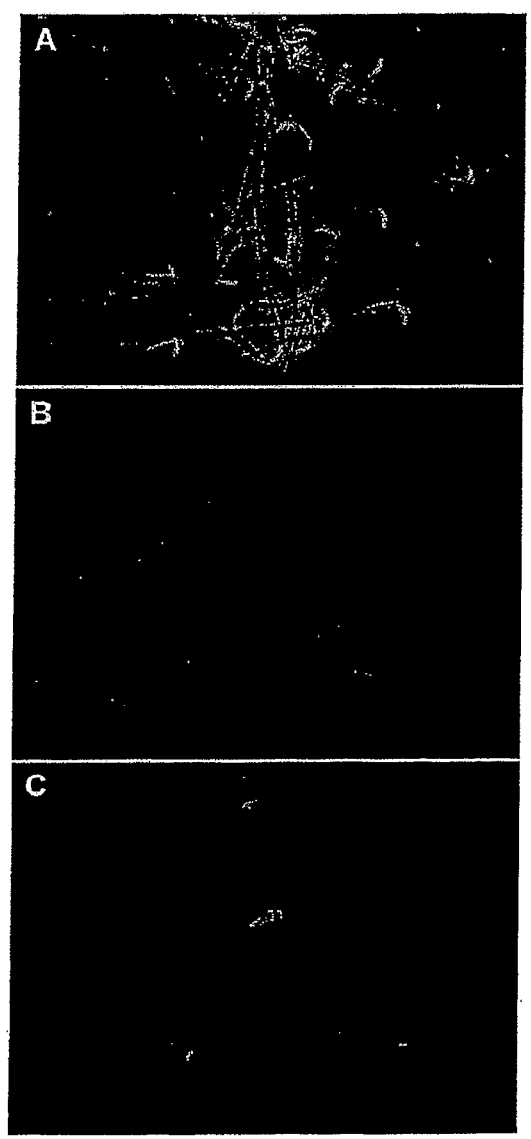
FIG. 10A is a micrograph depicting immunolocalization of SP22 on the equatorial segment of the head of fresh, unfixed cauda epididymal rat sperm using affinity-purified anti-SP22 peptide Ig.
FIG. 10B is a micrograph depicting the absence of immunostained SP22 when affinity-purified anti-SP22 peptide Ig was coincubated with 20 micrograms (10 micrograms each) of a mixture of the 15 mer (Peptide A—TVAGLAGKD-PVQCSR) (SEQ ID NO: 6) and 8 mer (Peptide B—DG-LILTSR) (SEQ ID NO: 7) peptides perviously used as immunogen.
FIG. 10C is a micrograph showing the immunolocalization of SP22 on the head of human sperm using anti-SP22 peptide Ig. In a separate experiment SP22 was immunolocalized to the equatorial segment of the head of sperm using anti-recombinant SP22 Ig (data not shown).

Affinity-purified anti-SP22 peptide localized over the anterior ventral, i.e., equatorial, region of the head on either fixed or fresh, unfixed cauda epididymal rat sperm (FIG. 10A). Immunostaining was completely ablated by coincubating the anti-SP22 peptide with a mixture of the immunogenic SP22 peptides, i.e., peptides #1 and #4 (equivalent to peptides A and B from the mimotope analysis described above) (FIG. 10B). When peptides #1/A and #4/B were tested separately during coincubation with the anti-SP22 peptide, the results indicated that only peptide #1 was exposed on fresh sperm. Coincubation with peptide #1/A ablated all immunostaining, while coincubation with peptide #4/B did not influence the level of immunostaining (FIGS. 11B and 11C). Staining was also evident over the head of human sperm (FIG. 10A). Using the affinity-purified anti-recombinant SP22, this staining was restricted to the equatorial segment of sperm from all species examined, including human (data not shown). The results as described above clearly indicates that the 15 amino acid sequence of peptide A is an exposed. domain, while the 8 amino acid sequence of peptide B is not exposed.

The third component of the strategy is predicated on the hypothesis that only epitopes having exposed domains play functional roles in fertility. To test this, cauda epididymal sperm was inseminated in utero following incubation with anti-SP22 peptide alone, or incubation with anti-SP22 peptide and individual peptides (i.e., peptide A and peptide B). Indeed, while the anti-SP22 peptide almost completely inhibited fertility, coincubation of anti-SP22 peptide and peptide A resulted in no alteration in fertility relative to historical values. In contrast therewith, coincubation of anti-SP22 peptide and peptide B also resulted in near complete inhibition of fertility, as shown in FIG. 12.

To repeat and to extend these results, affinity-purified anti-SP22 peptide (10 microliters, equivalent to 20 micrograms Ig) was incubated 1:50 (0.04 microgram/microliter) with cauda epididymal sperm five minutes prior to insemination. Fertility was once again reduced to less than 10% (FIG. 12). In contrast thereto, when 20 micrograms of peptide #1, equivalent to Peptide A from mimotope analysis, was added to the antibody and sperm for five minutes prior to insemination, the resultant fertility was equivalent to historical control values. However, when 20 micrograms of peptide #4, equivalent to Peptide B from mimotope analysis, was added to the antibody and sperm for five minutes prior to insemination, the reduction in fertility was as significant as when sperm were incubated with antibody alone. These data clearly demonstrate that the SP22 fragment peptide #1 (i.e., Peptide A from immunotope analysis) is a functional fragment in the modulation of fertility.

Collectively, these data clearly demonstrate that the exposed 15 amino acids of Peptide A represent a functional fragment of the SP22 molecule. In a similar fashion, any peptide can be assayed to determine if it, too, is a functional fragment of SP22. As indicated above, any fragments can readily be tested without undue experimentation to identify those fragments which modulate fertility. Targeting functional fragments is likely to effectively reduce fertility to 0% and makes the use of site-directed antagonists more feasible across many species, including humans.

Figure 13C:
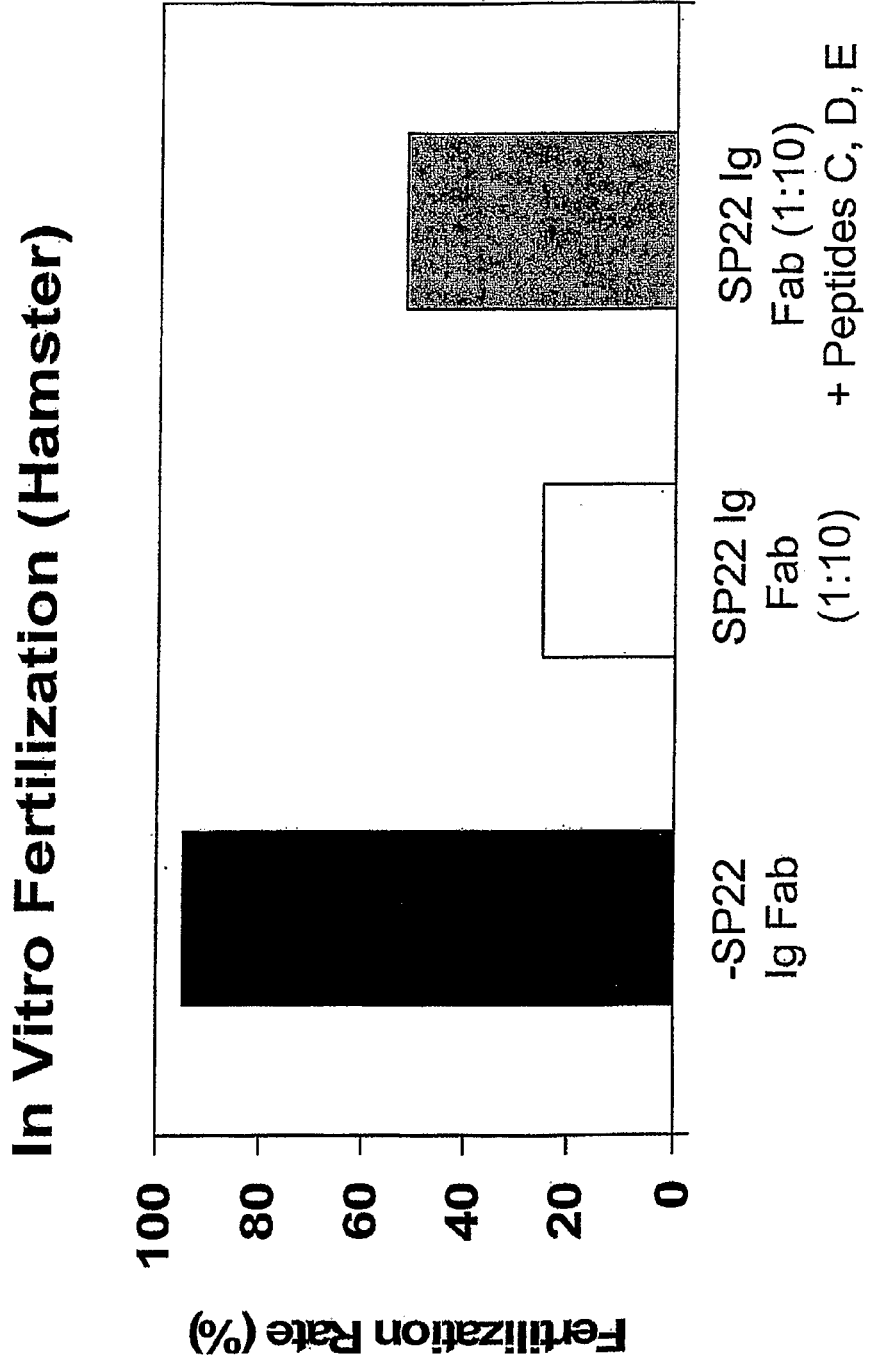

It could be argued that the effective inhibition of fertility with anti-SP22 Ig represents an inhibition mediated by steric hindrance rather than a molecular specific mechanism. To address this we prepared Fab fragments of the affinity purified Ig and repeated the fertility inhibition tests as well as the epitope mapping. FIGS. 13A-B show that the Fab preparation recognized the same linear epitopes as the intact Ig, and addition of the Fab preparation to sperm inhibited fertilization in vitro significantly (FIG. 13C). Moreover, the addition of peptides C, D, and E partially restored this inhibition suggesting that these are exposed functional SP22 peptide fragments (FIG. 13C).

EXAMPLE 8

Successful SP22 Vaccination of Mice and Rabbits

Adult male and female CD-1 mice at 60 and 40 days of age respectively, were allowed to acclimate to room conditions of 12 hour light/dark, 22±1° C., 50±10% relative humidity in an AAALAC-approved animal facility. 25 female mice were acclimated for one week, weighed, and randomized into one of the following groups: adjuvant control or recombinant SP22. Animals were assigned a number and identified with corresponding ear punches.

Mice were injected subcutaneously every 3 weeks for a total of three injections. Each injection represented 50 μg of purified full length rSP22 diluted 1:1 with monophosphoryl lipid A (MPL)+trehalose dimycolate (TDM)+Cell-wall skeleton (CWS) adjuvant. One week after the third injection, vaginal lavage samples were obtained using warm DPBS (100 ul) and an eye dropper. The ELISA was performed immediately following this procedure to obtain a pre-mating ELISA value for each female. One week later, males were introduced to females and allowed to cohabitate for five days of mating. Females were examined for the presence of vaginal plugs daily during cohabitation to confirm mating. Approximately three weeks later, females began delivering and the pups counted and litter weighed. Two weeks after all females gave birth vaginal lavage samples were obtained again for linear epitopes analysis. To obtain a sufficient sample volume for analysis, lavage samples from all non-pregnant females were pooled.

Figure 14A:
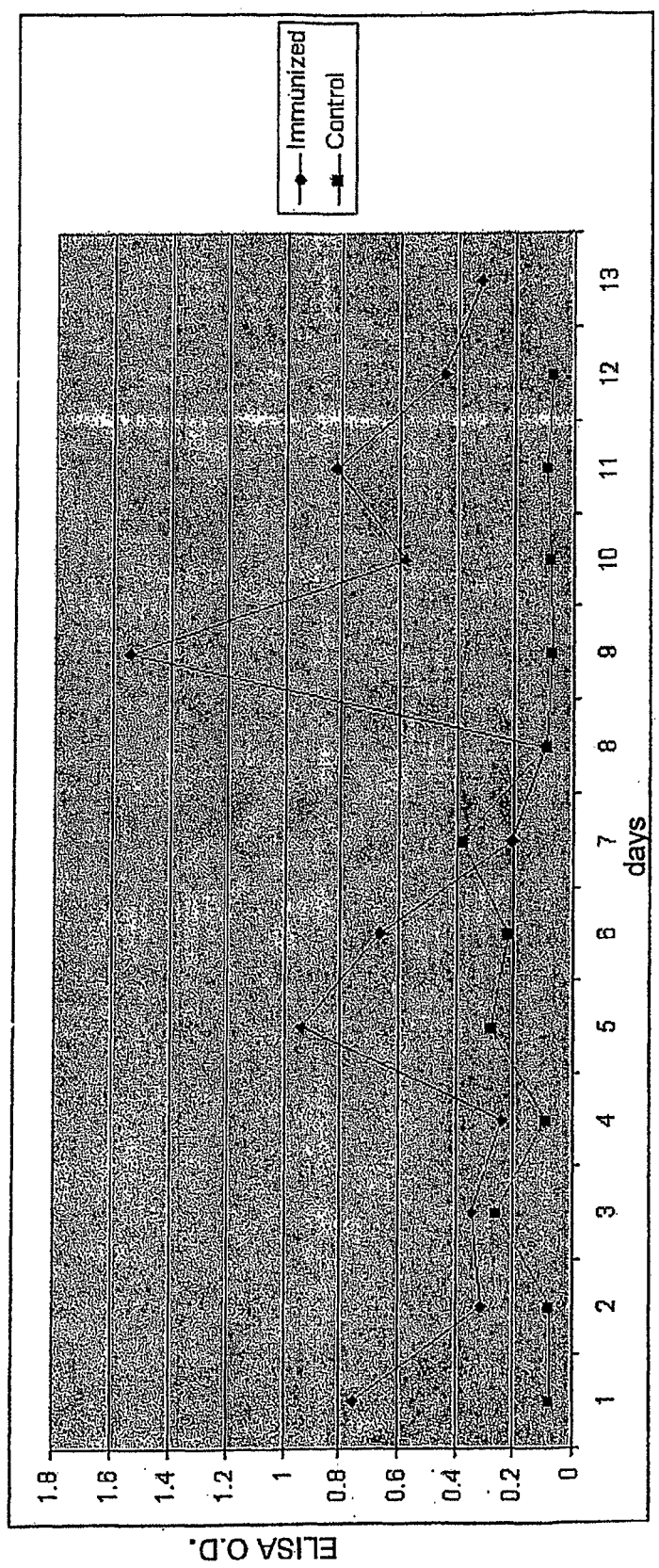
FIG. 14A is a graph showing levels of vaginal anti-rSP22 Ig in immunized and control (non-immunized) mice.
Figure 14B:
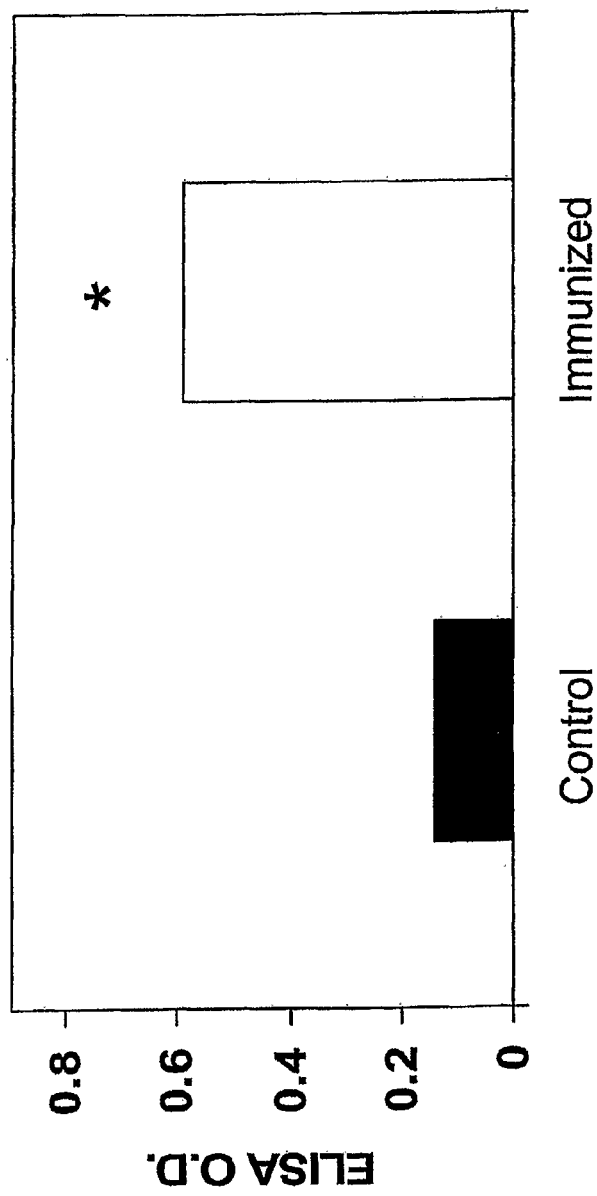
FIG. 14B is a bar graph comparing the average levels of vaginal anti-rSP22 Ig in vaginal lavage samples of female mice immunized with full length rSP22 (3×50 ug injections over 9 weeks) to average levels of vaginal anti-rSP22 Ig in mice immunized with adjuvant alone.
Figure 14C:
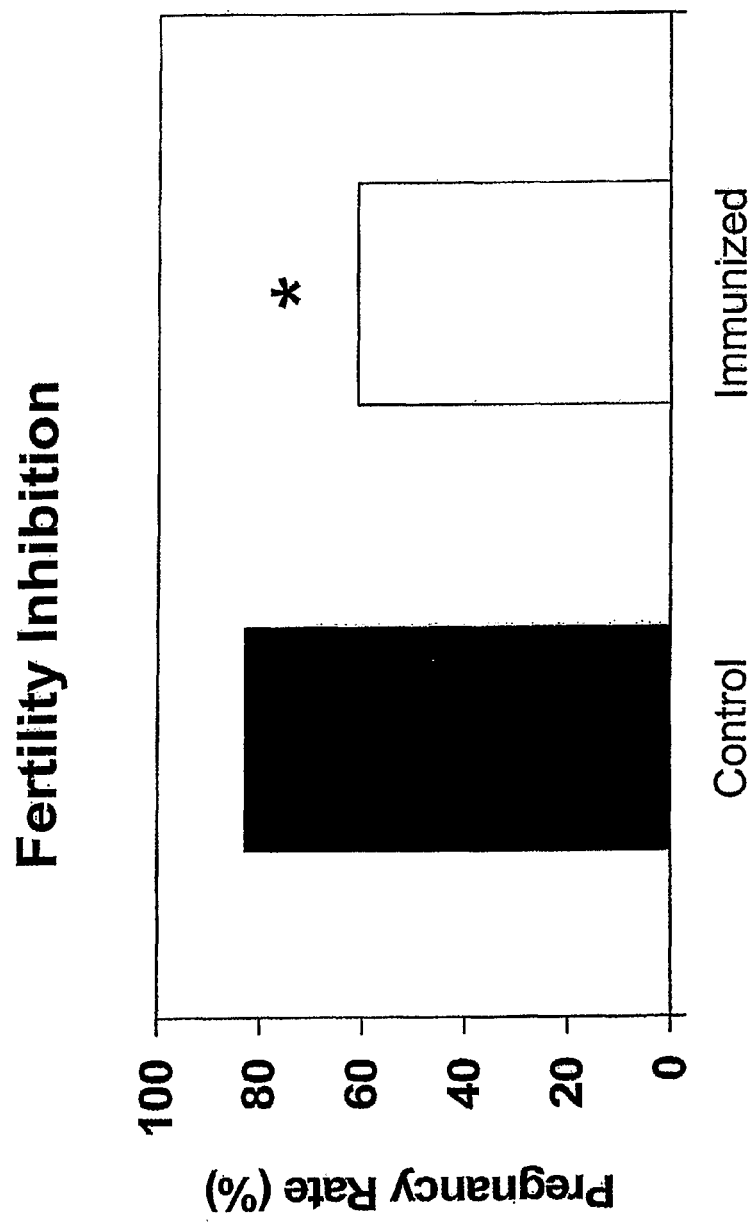
FIG. 14C is a bar graph comparing the pregnancy rates (%) of female mice immunized with full length recombinant SP22 when mated over the course of 4 days with naive males. It is important to note that immunized females with a pre-mating vaginal lavage Ig level greater than 0.7 did not become pregnant. This suggests that an effective level of anti-SP22 Ig in the vaginal mucosa can be determined and achieved.
Figure 14:
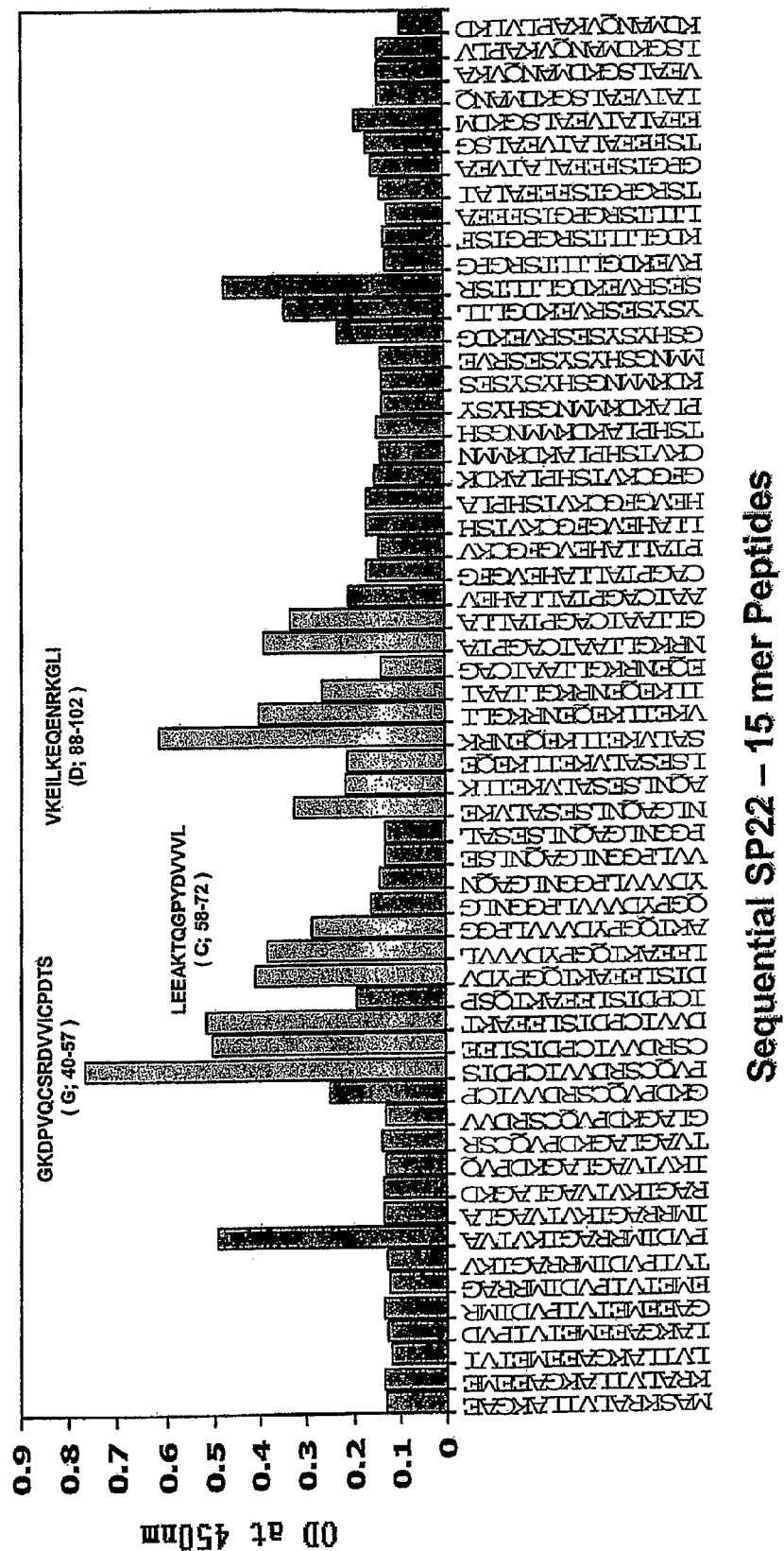
FIG. 14D is a bar graph illustrating the immunoreactivity of overlapping 15 mer SP22 peptides with affinity purified serum from rabbits immunized with full length rSP22 formulated with Synervax adjuvant.
FIG. 14E illustrates the immunoreactivity of overlapping 15 mer SP22 peptides with antibodies recovered from vaginal lavage samples of non-pregnant mice immunized with full length rSP22.
Figure 14:
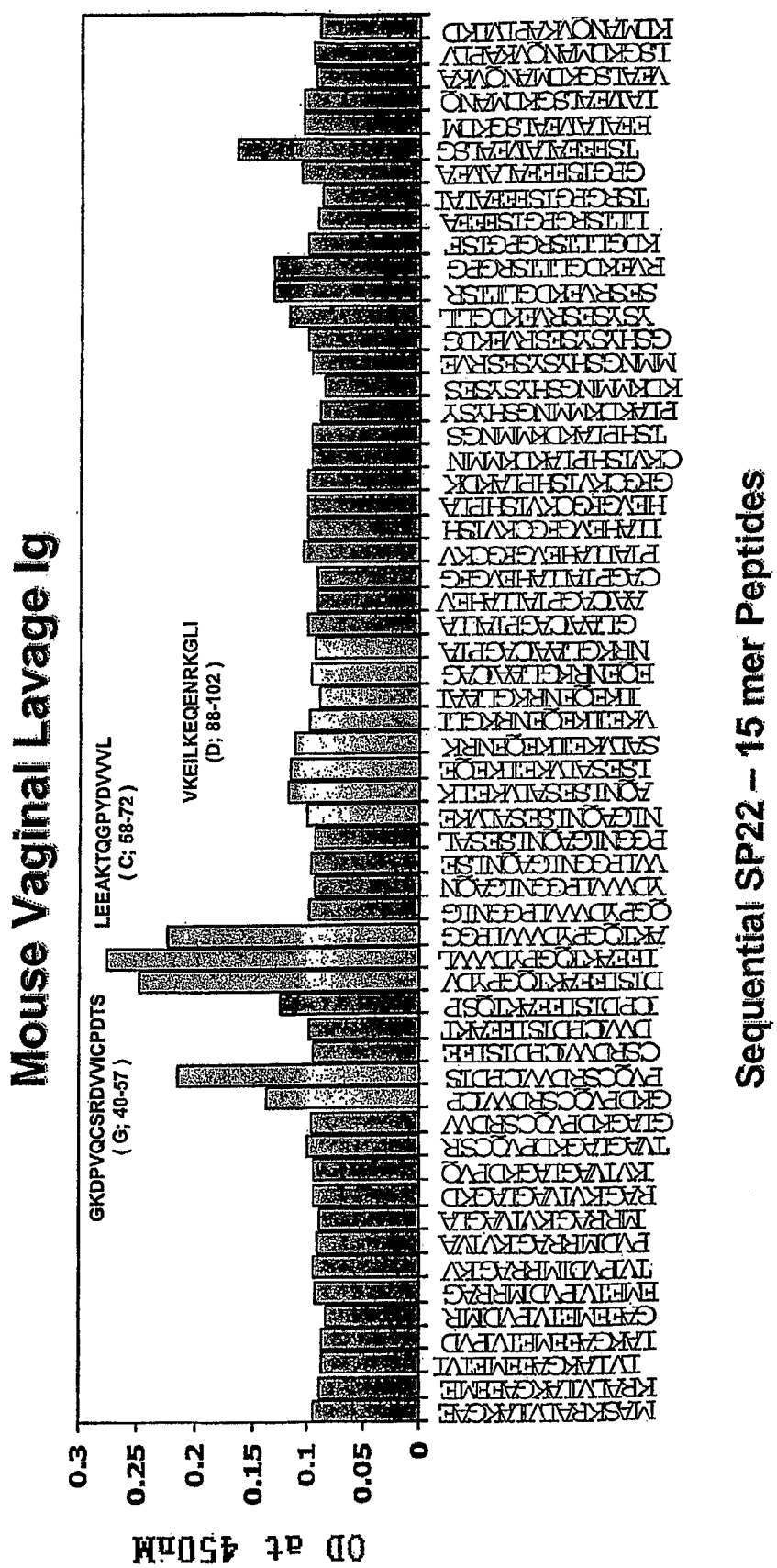

A significant reduction in fertility was observed in female mice immunized with full length recombinant SP22 (FIG. 14C). In summary, 77% of the immunized female mice expressed anti-SP22 Ig in vaginal lavage samples collected prior to mating, and the average vaginal Ig level was 0.59 compared to 0.14 in the control group (FIG. 14B). There was a significant 22% reduction in fertility in the group of immunized females. Importantly, each of the 3 females that had a pre-mating vaginal Ig level of 0.70 or greater failed to become pregnant) (Table 1). Post-partum vaginal lavage samples were obtained and pooled for linear epitope mapping. Epitope mapping revealed that the vaginal Ig obtained from non-pregnant immunized females recognized the same epitopes as the rabbit Ig shown to inhibit fertilization following in utero insemination (FIG. 14D-E).

The SynerVax™ vaccine adjuvant, which is a novel adjuvant that is entirely natural and has no toxicity associated with it was recently tested in combination with recombinant SP22. SynerVax™ adjuvant has been found to dramatically increase immunogenicity of antigens when co-administered and the adjuvant also acts to protect the antigens from proteolysis until the antigens are delivered, in a receptor-specific fashion, to the antigen presenting cells of the immune system. Active immunization of female rabbits with SynerVax™-SP22 complexes was found to produce antibodies in rabbits at doses of SP22 which were are approximately 20-100-fold lower than required when immunization was attempted using conventional immunization (i.e., Freunds' Complete Adjuvant [CFA]). Importantly, the epitope mapping revealed that the antibodies generated in rabbits using the SynerVax-SP22 complex recognized the same epitopes and reduced fertility following in utero insemination to the same extent as the rabbit antibody raised using conventional immunization. Moreover, the antibodies obtained from the vaginal lavage samples of non-pregnant immunized mice also recognized the same epitopes as the rabbit antibody that inhibited fertility. These epitopes correspond to Peptide G (SEQ ID NO: 73), Peptide C (SEQ ID NO: 8), and Peptide D (SEQ ID NO: 9) (see FIG. 14D-E).

In subsequent experiments, SP22 antibodies recovered from immunized rabbits were as effective in inhibiting fertilization in vivo and ex vivo fertility experiments as sheep Ig. Furthermore, in comparing FIG. 13B and FIG. 14D, we observed that the SP22 antibodies produced by the immunized rabbit recognized. amino acids 58-72 (peptide C) and amino acids 88-102 of SP22 (peptide D).

EXAMPLE 9

Vaccination using Truncated rSP22 (SEQ ID NO: 12; Amino Acids 47-102 of SEQ ID NO: 2) Compared to Full Length rSP22

Figure 17:
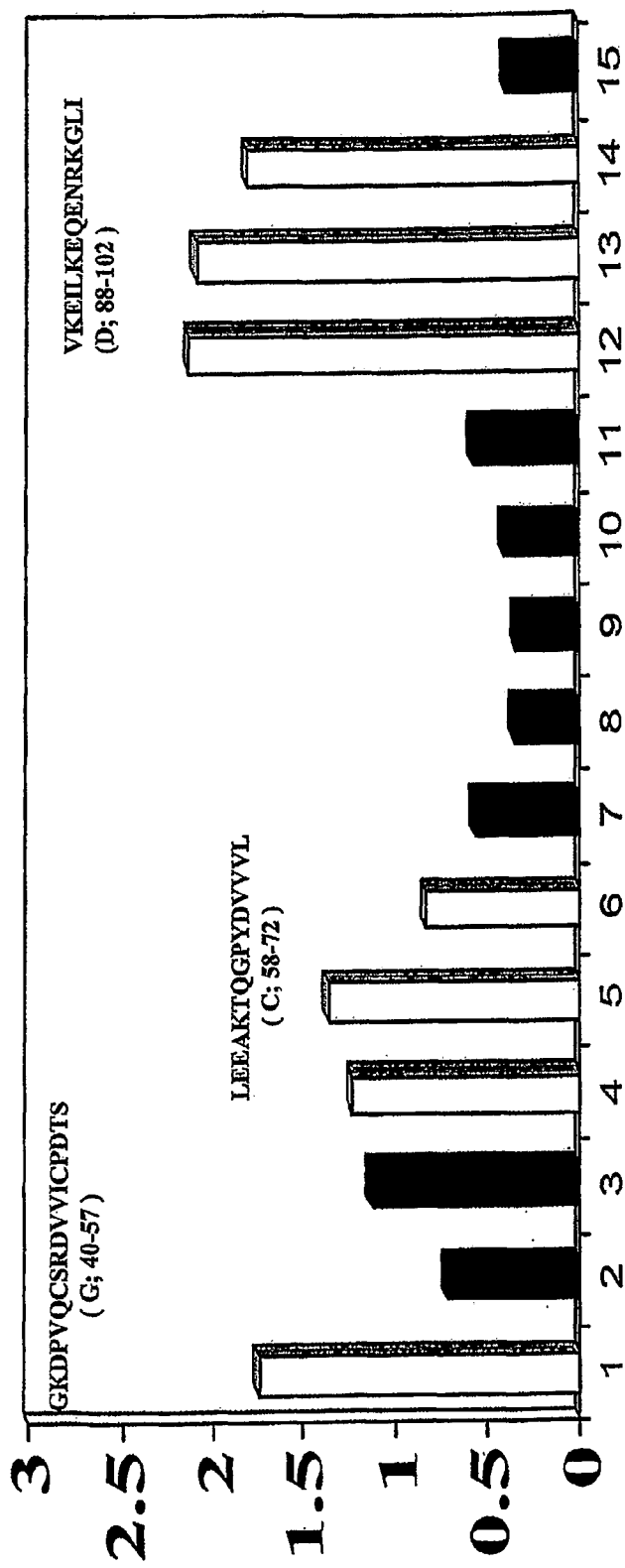
FIG. 17 is a bar graph showing antibody peptide recognition in serum of rabbits with 0% fertility following immunization with a truncated recombinant SP22 (SRDVVICP-DTSLEEAKTQGPYDVVVLPGGNLGAQNLSESALVK-EILKEQENRKGLI) (SEQ ID NO: 12). The serum for the epitope map was at a 1:32 dilution. The truncated rSP22 epitope map is compromised of 15 overlapping 15-mer sequences represented on the X axis as 1-15. Note that peaks of epitope recognition are observed at sequences 1, 4-6, and 12-14. These sequences correspond to Peptide G (SEQ ID NO: 73), Peptide C (SEQ ID NO: 8), and Peptide D (SEQ ID NO: 9).

Based on the above findings, a truncated rSP22 (SRDVVICPDTSLEEAKTQGP YDVVVLPGGNLGAQNLSESALVKEILKEQENRKGLI, SEQ ID NO: 12; amino acids 47-102 of SEQ ID NO: 2) was generated and used to immunize female rabbits. The truncated SP22 was significantly more effective in producing antibody in the serum of rabbits. Peptide recognition by antibody in serum of rabbits with 0% fertility following immunization with truncated rSP22 is shown in FIG. 17. The epitopes correspond to Peptide G (SEQ ID NO: 73), Peptide C (SEQ ID NO: 8), and Peptide D (SEQ ID NO: 9). Fertility appeared to be correlated to levels of antibody in vaginal lavage samples recognizing Peptide D (not shown).

Antibody was also generated in sheep using truncated recombinant SP22. Using both the pepset corresponding to the full length SP22 molecule, as well as the 15 sequence pepset corresponding to the truncated recombinant SP22, it was observed that the same epitopes (peptides) were recognized (data not shown). These peptides were once again Peptide G (GKDPVQCSRDVVICPDTS), Peptide C (LEEAKTQGPYDVVVL), Peptide X (QNLSESALVKEILKEQENRKGLI) and Peptide D (VKEILKEQENRKGLI). Peptide X represents Peptide D plus a few amino acids on the N-terminal side of Peptide D. Further, antibody to the truncated recombinant SP22 localized to the sperm head similar to antibody against the full length SP22 (data not shown).

Figure 18:
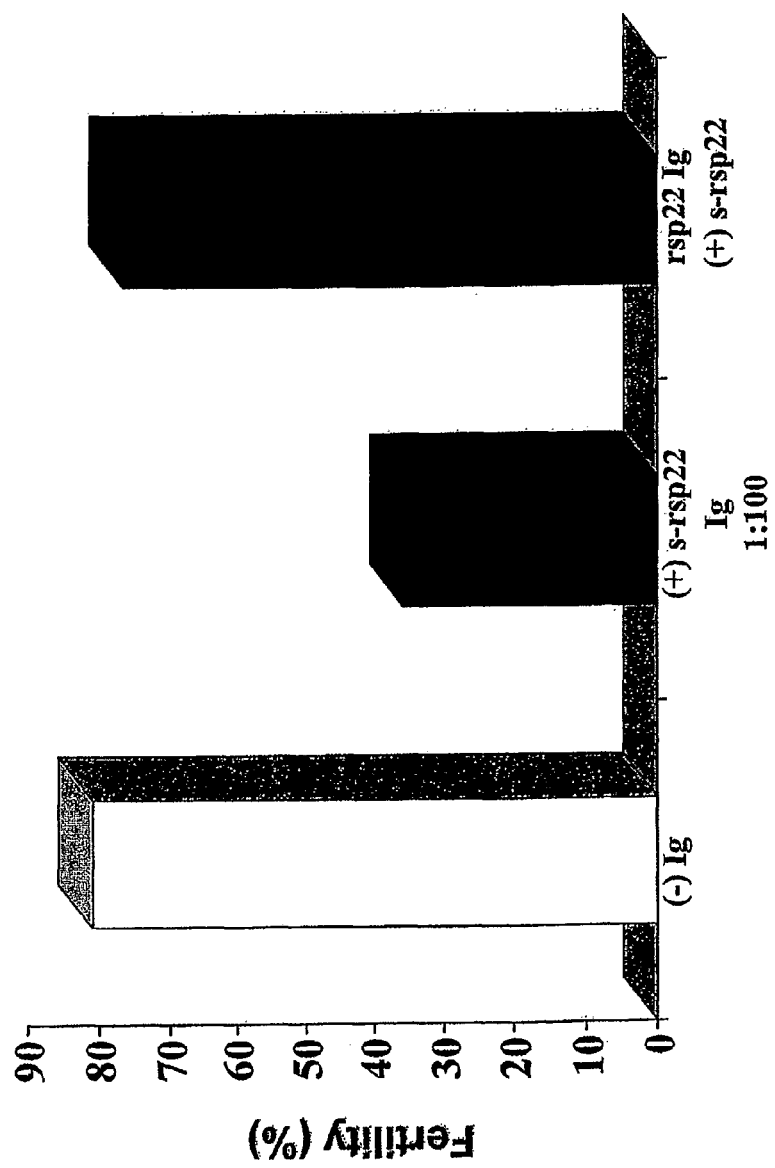
FIG. 18 is a bar graph showing percent fertility following in utero insemination under control conditions (no antibody); antibody to truncated rSP22 (SEQ ID NO: 12) diluted 1:100; and antibody to truncated rSP22 plus the truncated rSP22 peptide.

In subsequent experiments, antibodies against truncated rSP22 were characterized to determine ability to inhibit fertility and exposed epitopes. In utero insemination experiments using affinity purified antibody to truncated recombinant SP22 at a 1:100 dilution inhibited fertilizing ability as shown in FIG. 18. This level of inhibition was previously observed using antibody to full length SP22 only at a 1:10 dilution. Truncated recombinant SP22 competed effectively with the Ig to restore fertility similar to the control (see FIG. 18). Additional experiments using both rabbit and rat sperm showed. that this antibody to the truncated SP22 immunostained the sperm head only when the Peptide X (QNLSESALVKEILKEQENRKGLI) epitope is exposed as incubation of sperm with Ig+Peptide X completely ablated immunostaining (data not shown).

EXAMPLE 10

Vaccination in Mice using Peptide X

Figure 19:
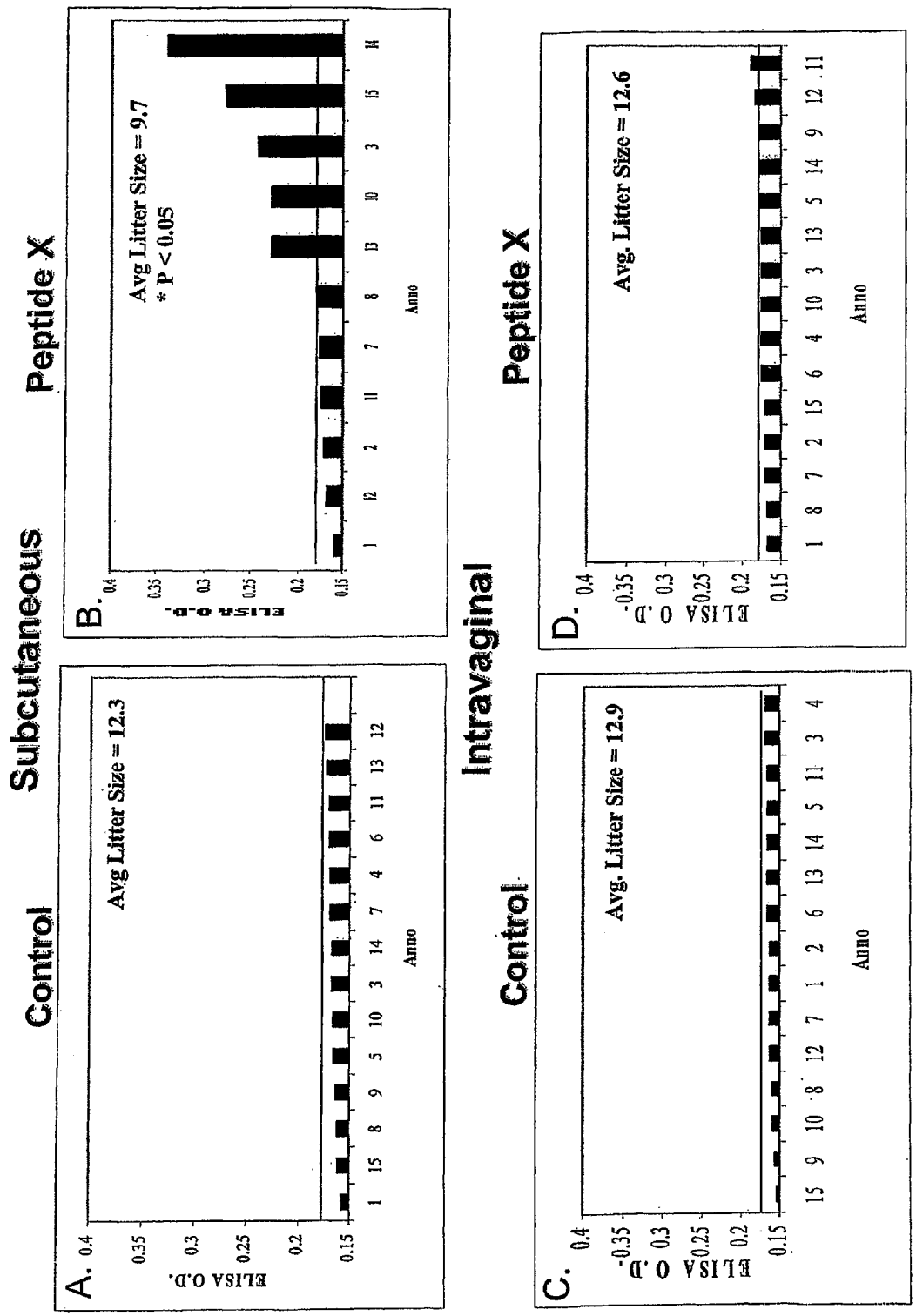
FIG. 19A-D is a series of bar graphs showing antibody levels and fertility following immunization.
Figure 20A:
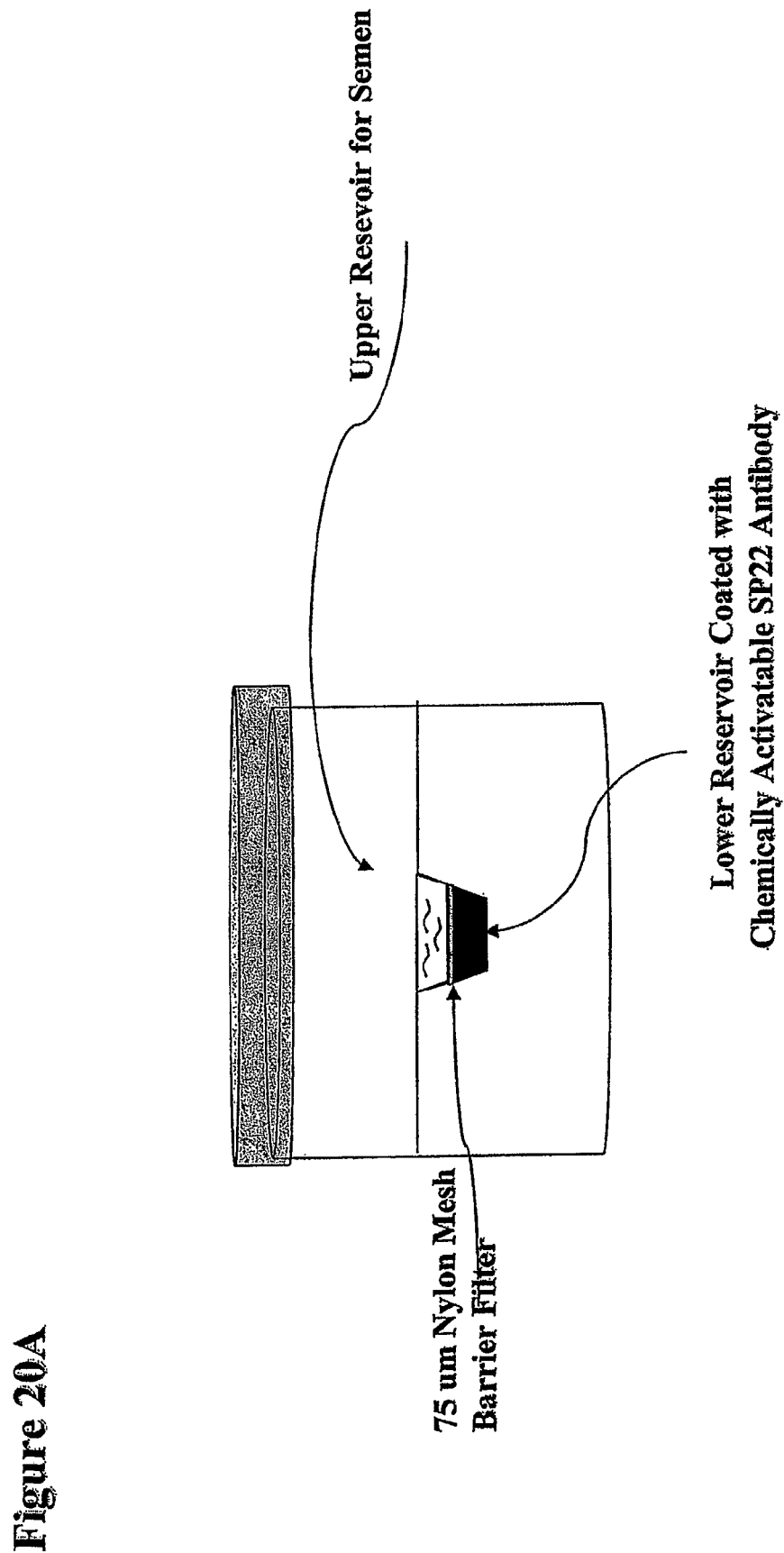
FIGS. 20A and B are schematic diagrams of SP22 diagnostic kits for detecting the presence of SP22 in a sperm sample. Both A and B depict a removable application zone (a first reservoir) for adding the sperm sample and a detection zone (a second reservoir) comprising SP22 antibody, separated by a nylon mesh barrier filter. A cover for the application zone is shown in both A and B. In A, the detection zone is coated with a chemically activatable SP22 antibody. In B, there is a side port for adding solution to the detection zone. Also depicted is a second port separated from the detection zone with filter for exchanging solutions in the detection zone.
Figure 20B:
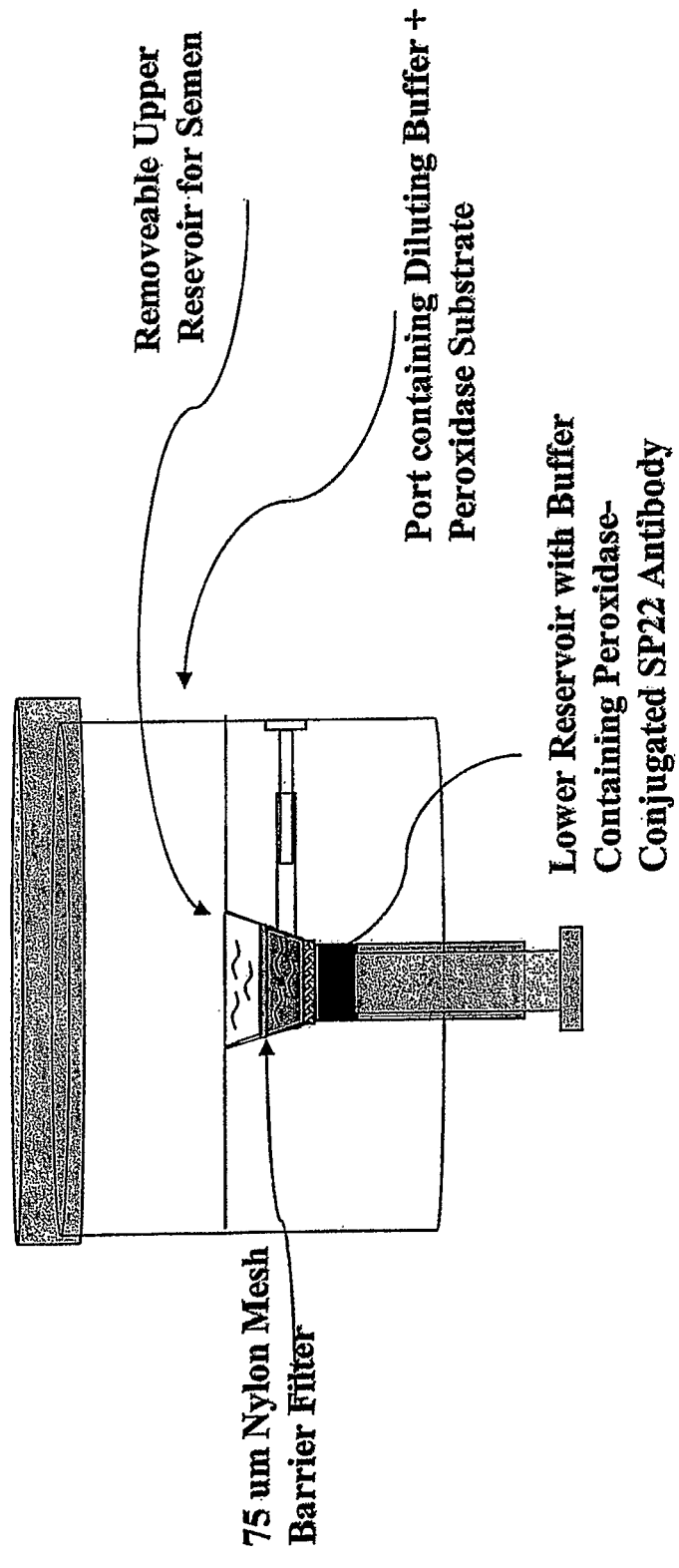
Figure 21:
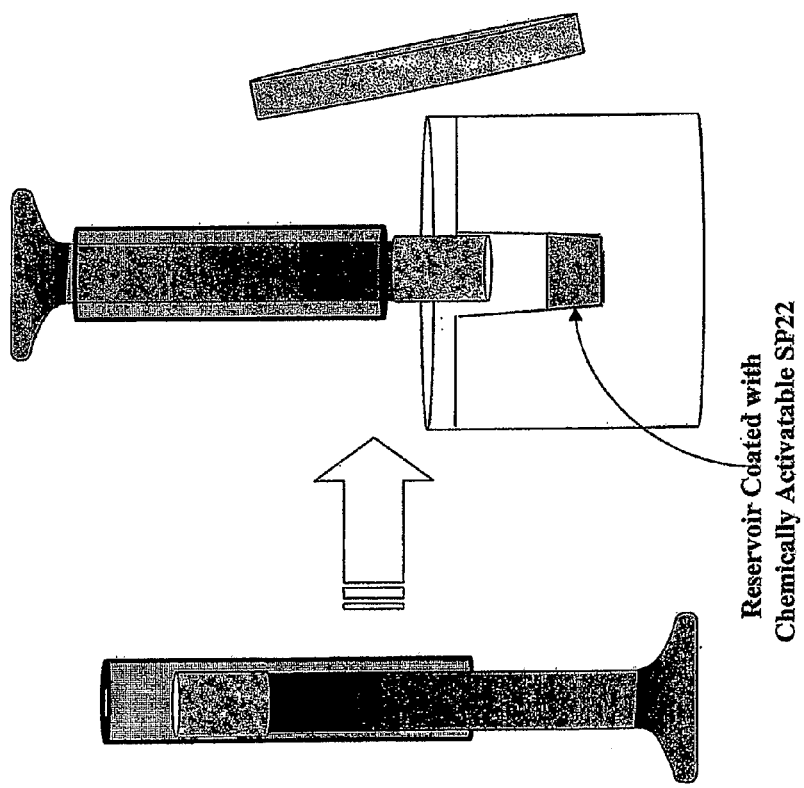
FIGS. 21A and B are schematic diagrams of SP22 diagnostic kits for detecting the presence of SP22 antibodies in a vaginal sample. Both A and B depict a tampon-like device for collecting a vaginal sample and a monitoring device. As depicted in both A and B, the collection device is added to the monitoring device to transfer the vaginal sample to a reservoir in the monitoring device. In A and B, the reservoir is coated with a chemically activatable SP22. In B, there is a side port for adding solution to the reservoir. Also depicted is a second port separated from the reservoir with filter for exchanging solutions in the reservoir.
Figure 21B:
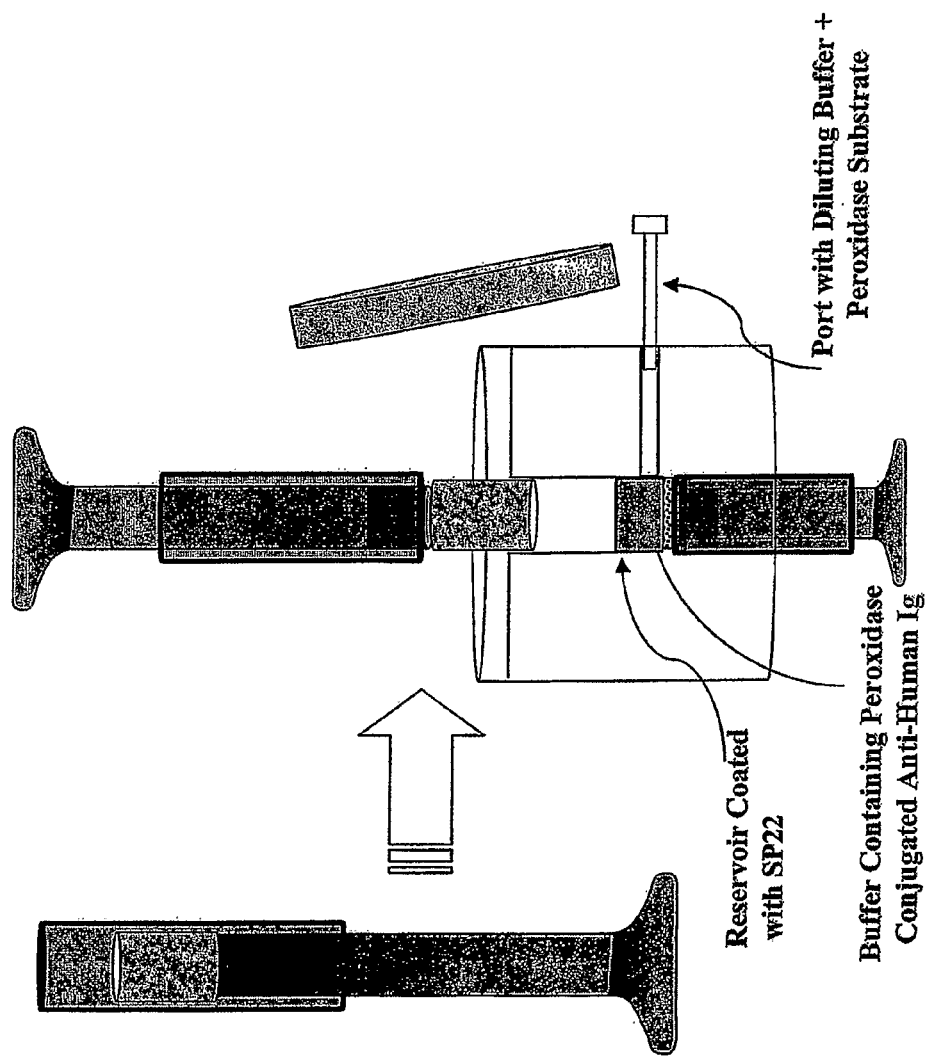

Female mice were immunized with peptide X (QNLSESALVKEILKEQENRKGLI; amino acids 80-102 of SEQ ID NO: 2) alone to determine if this peptide alone is sufficient to reduce fertility. Peptide X was delivered using two different routes, subcutaneous injection or intravaginal swabs. Only subcutaneous administration resulted in significantly elevated levels of vaginal lavage Ig as shown in FIG. 19. Litter size was significantly reduced in the group of females immunized with Peptide X alone via subcutaneous delivery. Moreover, females with the highest levels of Ig in serum tended to have the smaller litters (not shown).

EXAMPLE 11

Successful Development of an ELISA Assay to Quantitate SP22 Levels in Sperm Extracts and SP22 Ig Levels in Immunized Females Briefly, adult male rats were treated with hydroxyflutamide as previously described. Caput sperm was used for a quantitative sperm membrane protein evaluation. For this, sperm ($10-40 \times 10^6$) were transferred to a microcentrifuge tube and washed twice by centrifugation (3000 g, 10 min) in sperm isolation buffer with freshly-added 0.2 mM phenylmethylsulphonyl fluoride (PMSF; Sigma, #P-7626). After the final wash, sperm were extracted for 1 hr at room temperature with 1 ml of 80 mM n-octyl-B-glucopyranoside (OBG) in 10 mM Tris, pH 7.2 containing freshly-added PMSF. Following a final centrifugation (10,000×g, 5 min), the supernatant was removed and frozen (–70° C.). Samples were thawed and each extract was concentrated with 1 mM Tris buffer, pH 7.2, by two centrifugations (3,000×g, 45 min, 4° C.) in Ultrafree-4 centrifugation filter units (Millipore). Protein concentration was determined using a Pierce protein assay kit. Sample volumes containing 30 ug protein were lyophilized and protein was solubilized for 30 min at room temperature in 45 µl of sample buffer consisting of 5.7 g urea, 4 ml 10% NP-40, 0.5 ml ampholytes (Serva; 3-10 only), and 0.1 g dithiothreitol per 10 ml.

The caput sperm extract and caput luminal fluid was used for SP22 quantitation via ELISA. For this, 96-well tissue culture plates (Costar 3595 96-well cell culture; Corning Inc., Corning, N.Y.) were used. A standard curve was generated using serial dilutions of antigen, i.e. full length rat recombinant SP22 (rSP22; Klinefelter et al., 2002b); 0, 0.01, 0.05 0.1, 0.5, 1, 5, and 10 µg in 50 µl/well; all dilutions were in NaHCO$_3$ pH 9.5. Initially, sperm extracts diluted in Dubecco's Phosphate Buffered Saline (DPBS; Gibco, Grand Island, N.Y.) were plated at 0, 0.01, 0.5, 0.1, 0.5, 1, 5, and 10 µg in 50 µL/well. Evaluation of the response in control extracts indicated 10 µg provided a maximal response with the least variance so 10 µg protein loading was used for all samples subsequently. Duplicate wells were used for both the SP22 standards and each sperm extract. The plates were stored overnight at 4° C. to maximize antigen absorption. The following day, unbound antigen was removed by inverting the plate and shaking gently. A blocking step consisted of addition of milk protein (caseinate or dry milk powder) in DPBS (150 µg/well) followed by incubation for 1 h at 37° C. Sheep anti-rSP22 diluted 1:1000 in DPBS+1% BSA was added (50 ul/well) and allowed to bind during incubation for 1 h at 37° C. After 3 washes with DPBS+1% BSA (200 ul/well), peroxidase conjugated rabbit anti-sheep antibody (Pierce Immunopure 31480, Rockford, Ill.) diluted 1:500 in DPBS+1% BSA was added (50 ul/well) and allowed to incubate for 1 h at 37° C. After 4 washes with DPBS w/1% BSA, the peroxidase substrate ABTS (Pierce, #37615) was added (100 µl/well). The reaction was allowed to develop over a 15-20 min period. Absorbance was read using FLUOstar Galaxy software (BMG Labtechnologies Inc., Durham, N.C.) at 405 nm excitation, no emission.

For quantitation of antibody to SP22 in vaginal lavage samples, affinity-purified sheep anti-rSP22 diluted 1:5000 in DPBS+1% BSA was added (50 µl/well) to rSP22 standard lanes, while 1:4 and 1:8 dilutions of mouse lavage samples were added (50 µl/well). Antibody was allowed to bind during incubation for 1 h at 37° C. After 4 washes with DPBS+1% BSA (200 µL/well), peroxidase conjugated rabbit anti-sheep antibody (Pierce Immunopure 31480, Rockford, Ill.) diluted 1:500 in DPBS +1% BSA was added (50 µl/well) to rSP22 standard lanes, and peroxidase-conjugated rabbit anti-mouse antibody (Pierce Immunopure 31457) diluted 1:500 in DPBS+1% BSA was added (50 µl/well) to vaginal lavage sample wells and allowed to incubate for 1 h at 37° C. After 4 washes with DPBS w/1% BSA, the peroxidase substrate ABTS (Pierce, #37615, Rockford, Ill.) was added (100 µl/well). The reaction was allowed to develop over a 15-20 min period. Absorbance was read using FLUOstar Galaxy software (BMG Labtechnologies Inc., Durham, N.C.) at 405 nm excitation, no emission.

Figure 15:
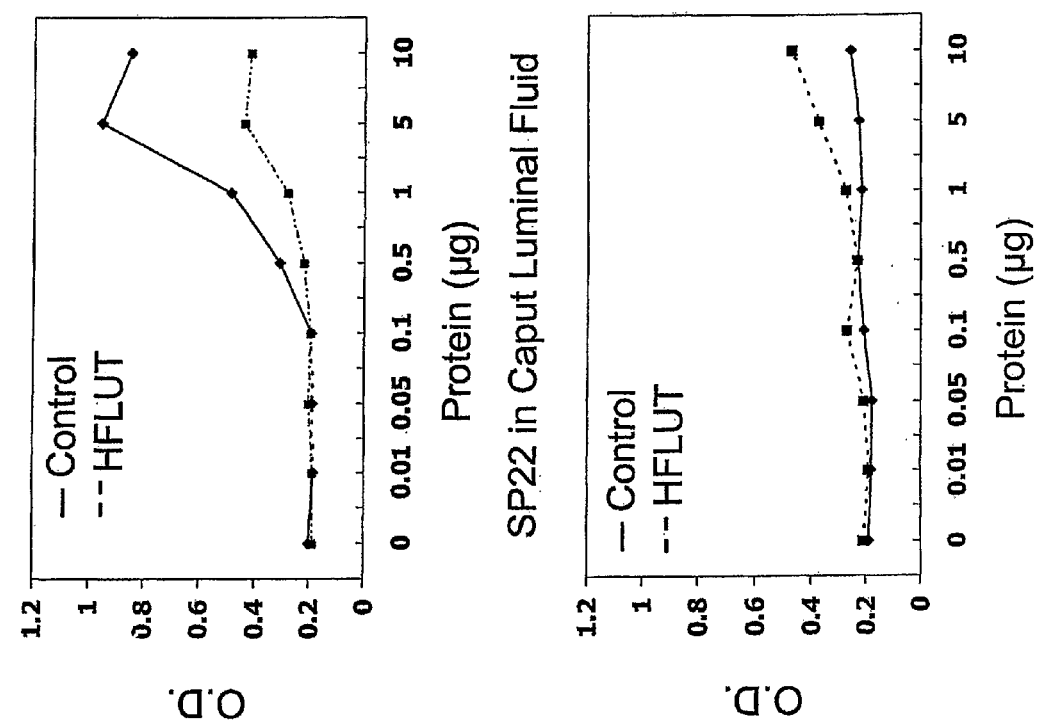
FIG. 15 are graphs showing levels of SP22 in caput sperm extracts and caput luminal fluid in rats treated with or without hydroxyflutamide (HFLUT) as quantified by ELISA.
Figure 16:
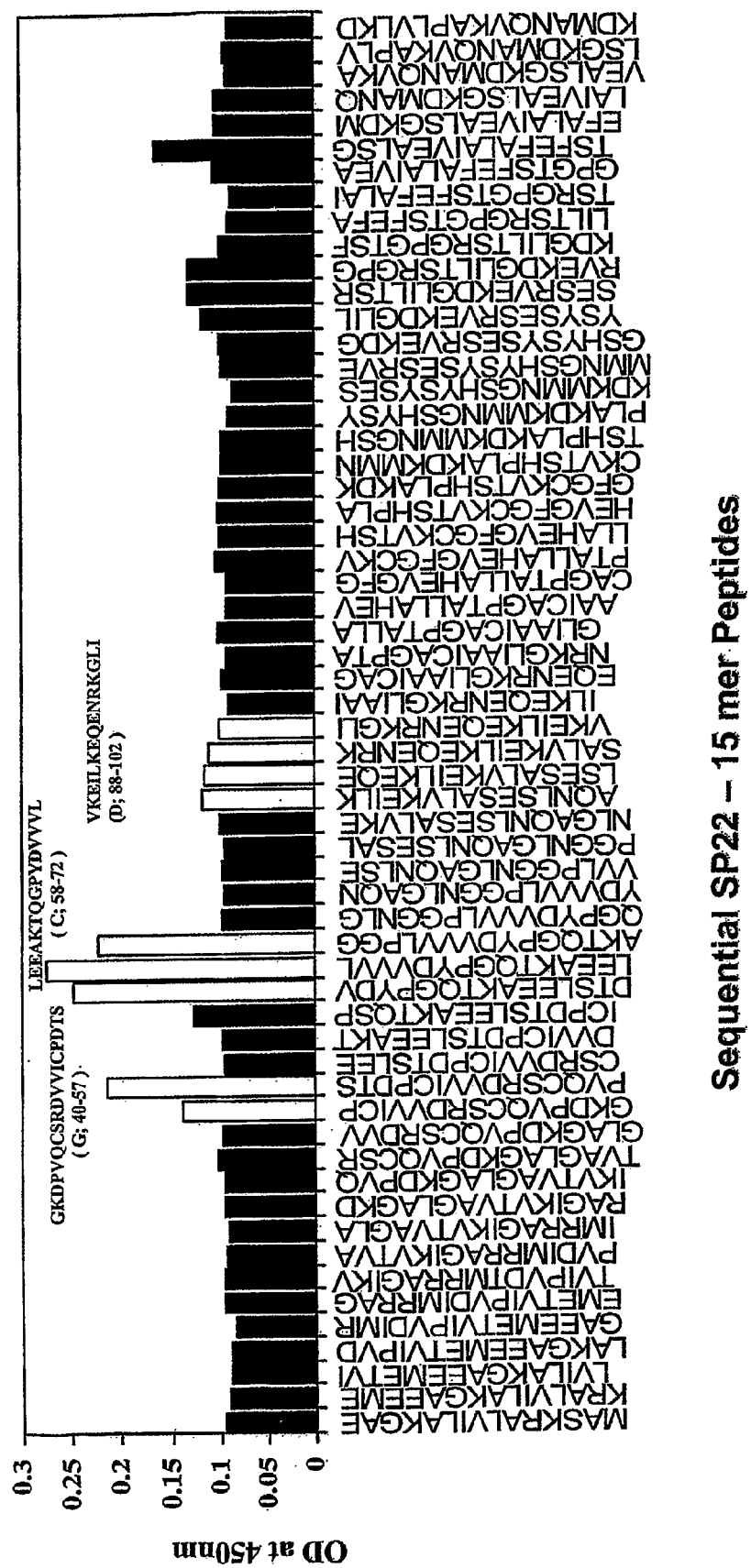
FIG. 16A is a bar graph illustrating the immunoreactivity of overlapping 15 mer SP22 peptides with affinity purified serum from mice immunized with full length rSP22.
FIG. 16B illustrates the immunoreactivity of overlapping 15 mer SP22 peptides with antibodies recovered from vaginal lavage samples of non-pregnant mice immunized with a truncated rSP22 (SRDVVICPDTSLEEAKTQGPYDVVVLPG-GNLGAQNLSESALVKEIL KEQENRKGLI) (SEQ ID NO: 12).
Figure 16:
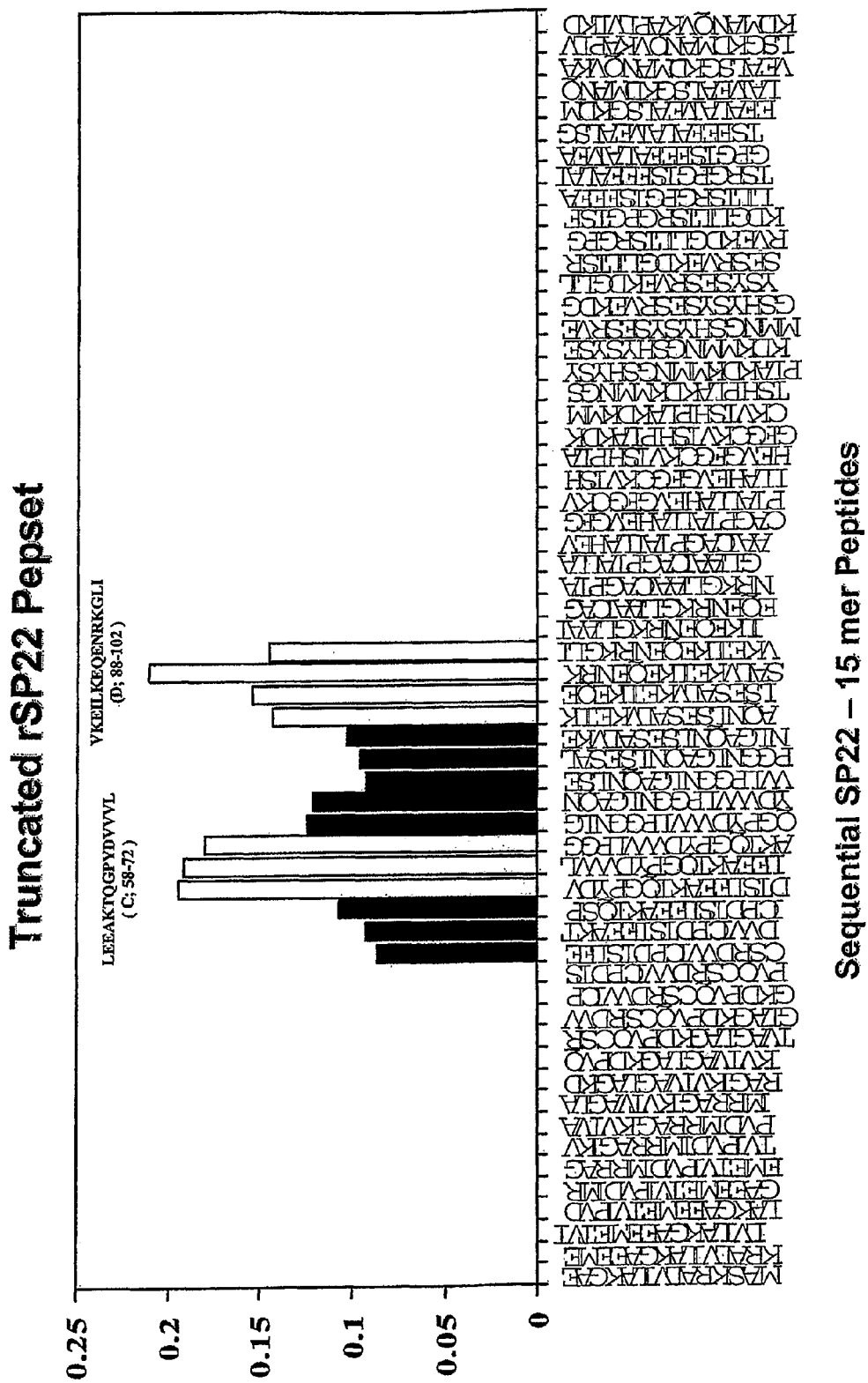

As observed in FIG. 15, quantitation of SP22 in caput sperm extracts by ELISA revealed that SP22 was significantly decreased in males exposed to hydroxyflutamide (HFLUT) compared to SP22 levels in control, untreated adult male rats. This is consistent with previous studies demonstrating that chemical insults can result in the shedding of SP22 from the sperm membrane. FIG. 15 also shows that immunoreactive SP22 increases in the epididymal fluid (sperm free) compartment consistent with the notion that as SP22 is shed from the sperm membrane it accumulates in the fluid compartment. By analogy, it is reasonable to assume that a similar association occurs in ejaculates. If so, men whose sperm quality is compromised might be expected to have increased levels of SP22 in seminal plasma as SP22 levels on sperm are decreased.

This is consistent with previous studies demonstrating that chemical insults can result in the shedding of SP22 from the sperm membrane. Likewise, the Figure shows that immunoreactive SP22 increases in the epididymal fluid (sperm free) compartment consistent with the notion that as SP22 is shed from the sperm membrane it accumulates in the fluid compartment. By analogy, it is reasonable to assume that a similar association occurs in ejaculates. If so, men whose sperm quality is compromised might be expected to have increased levels of SP22 in seminal plasma as SP22 levels on sperm are decreased.

EXAMPLE 12

The Relative Expression Levels of SP22 on Sperm may be used as a Valid Measure of Sperm Quality and Fertility Quantification of SP22 on epididymal sperm or ejaculated sperm may be accomplished using a site-directed primary antibody that is either conjugated for direct signal detection or derivitized upon binding to enable signal detection. Ideally, such an antibody will recognize one or more exposed functional epitopes. Further, since the amino acid sequence is highly conserved across species, such an antibody will be useful as a biomarker of fertility in men, domestic animals, and laboratory animal models.

We used an antibody to full length SP22 to detect differences in expression on cauda epididymal rodent sperm. However, when identical methodology was applied to ejaculated sperm (e.g. rabbit, stallion) immunostaining patterns were more variable and generally less intense. This proved to be a function of handling and processing prior to the addition of antibody to the sample. By reducing the washings and fixation time we were able to markedly improve the level and consistency of immunostaining.

Figure 22:
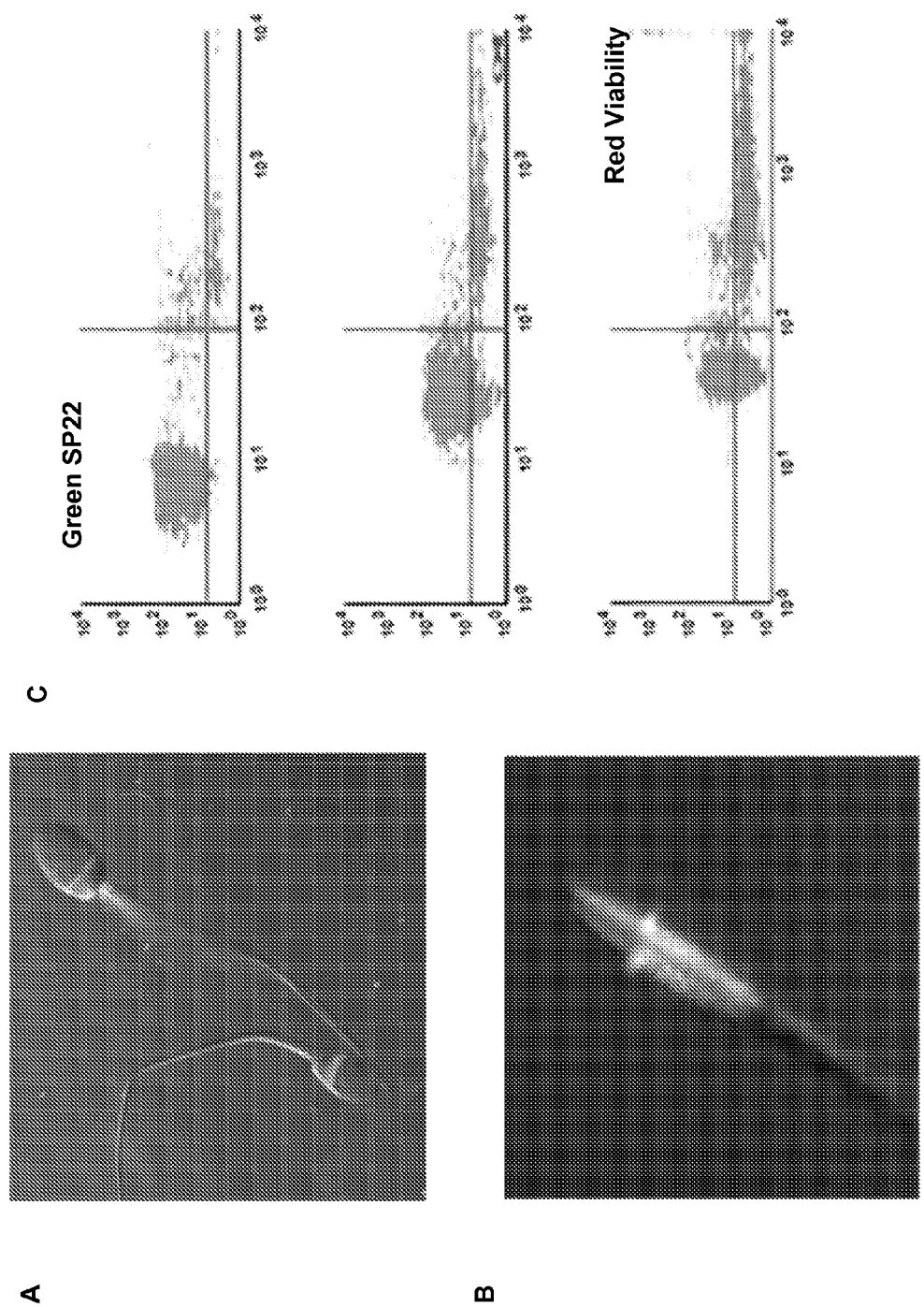
FIGS. 22A and B depict rabbit sperm immunostained with affinity purified full-length rSP22 antibody showing equatorial localization from two different views.
FIG. 22C shows that when ejaculated rabbit sperm are labeled with a red viability dye prior to fixation and then immunostained for SP22 after fixation both the red staining sperm reflecting membrane damage and the green SP22 staining can be evaluated by flow cytometry. The three cytograms depicted represent this dual labeling of ejaculated sperm from three rabbits. The sperm from the first rabbit (top cytogram) has very little red staining and the highest green SP22 staining. By contrast, sperm from the third rabbit (bottom cytogram) has the greatest amount of red staining indicating significant membrane damage and the least SP22 staining. The sperm in the second rabbit's ejaculate (middle cytogram) is intermediate in quality, with less SP22 staining that the first rabbit, but less red viability dye than the third rabbit. These data indicate the relative expression of SP22 on sperm can be used as a valid measure of sperm quality, and presumably fertility.

FIGS. 22A and B depicts SP22 localization over the equatorial region of the head of ejaculated rabbit sperm. When ejaculated sperm are allowed to swim through a nylon mesh culture well insert into buffer and then fixed briefly, the integrity of SP22 expression is maintained and reflects its expression at the time of ejaculation. By incorporating a fixable viability dye, one can evaluate both SP22 expression and viability of sperm in an ejaculate. FIG. 22C depicts cytograms of ejaculated sperm from three different rabbits stained for both SP22 and viability; the viability dye is taken up by sperm with membrane damage. As the percentage of sperm in an ejaculate with membrane damage increases, the SP22 (green) signal decreases as the viability (red) signal increases. Whether the level of SP22 immunostaining on ejaculated motile sperm correlates with the level of SP22 in a detergent extract of these sperm as measured by either ELISA or 2D SDS-PAGE and with the fertility of sperm will be determined.

EXAMPLE 13

Identification of Additional SP22 Functional Fragments for use as Antigens for Contraceptive Antibodies or as Antifertility Vaccines Synthetic peptides corresponding to linear epitope sequences Peptides C, D and X were used to determine which, if any, of the sequences were actually exposed on the sperm surface. When rabbit sperm were incubated with affinity purified antibody to N-terminal truncated (NT) rSP22 the typical pattern of immunostaining over the equatorial segment of the head was observed (FIG. 23A). This suggested that the third epitopic sequence, i.e. peptide E, recognized by the antibody to full-length rSP22 may not be exposed. That the antibody to NT-rSP22 effectively inhibited fertility, coupled with the notion that Peptide E may not be exposed, prompted us to speculate the NT-rSP22 antibody recognized an exposed and functional domain(s). When Peptide C was added to antibody to NT-rSP22, immunostaining of SP22 over the equatorial segment was somewhat reduced (FIG. 23B). However, a much greater reduction in immunostaining was observed when Peptide X was added to the antibody (FIG. 23C); a comparable reduction also was observed when Peptide D was added to the antibody (not shown). These results indicate that while a portion of Peptide C seems to be exposed, most if not all of the linear sequence comprising Peptide D is exposed on the sperm surface.

TABLE 1

ELISA data and Pregnancy Rates in Control and Immunized Mice

| Treatment | Elisa Data | Non-Pregnant | # Pups |
|---|---|---|---|
| C1 | 0.08 | | 11 |
| C2 | 0.08 | | 16 |
| C3 | 0.26 | | 11 |
| C4 | 0.09 | | 11 |
| C5 | 0.28 | | 12 |
| C6 | 0.22 | | 11 |
| C7 | 0.38 | | 14 |
| C8 | 0.09 | NP | ? |
| C9 | 0.07 | | 14 |
| C10 | 0.08 | | 13 |
| C11 | 0.09 | NP | ? |
| C12 | 0.07 | | 10 |
| I1 | 0.76 | NP | |
| I2 | 0.31 | | 14 |
| I3 | 0.34 | | 13 |
| I4 | 0.24 | NP | ? |
| I5 | 0.94 | NP | |
| I6 | 0.67 | | 14 |
| I7 | 0.21 | | 8 |
| I8 | 0.1 | | 12 |
| I9 | 1.54 | NP | |
| I10 | 0.58 | | 13 |
| I11 | 0.82 | NP | |
| I12 | 0.45 | | 9 |
| I13 | 0.32 | | 12 |

The practice of the present invention will employ, unless otherwise indicated, conventional techniques of virology, protein chemistry, cell biology, cell culture, molecular biology, microbiology, and recombinant DNA, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); The Treatise, *Methods In Enzymology* (Academic Press, Inc., N.Y.); and *Methods In Enzymology,* Vols. 154 and 155 (Wu et al. eds.); The Handbook of Experimental Immunology, Volumes 1 to 4, (D. N. Weir, editor); Gacesa and Ramji *Vectors* (1994) John Wiley & Sons; *Tissue Culture,* Academic Press, Kruse and Patterson, eds. (1973); Harlow and Lane, *Antibodies: A Laboratory Manual* Cold Spring Harbor Laboratory pps 224-227 (1988); Goding, *Monoclonal Antibodies: Principles and Practice,* pp. 59-103 (Academic Press, 1986);

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A kit for detecting a SP22 polypeptide on a motile sperm in a semen sample comprising:
    an application zone for adding a sperm sample,
    a detection zone comprising an SP22 antibody for determining if the SP22 polypeptide is present on the surface of the motile sperm in the semen sample, wherein said SP22 antibody binds to a portion of said SP22 polypeptide selected from the group consisting of amino acids 40-57, 58-72, 88-102, 80-102, 118-132, 160-174, and 47-102 of SEQ ID NO: 2.

2. The kit of claim 1, further comprising a barrier zone separating the application zone and the detection zone.

3. The kit of claim 2, wherein barrier zone separates a subset of sperm having an average motility higher than an average motility of sperm of the sample.

4. The kit of claim 3, wherein the barrier zone comprises a barrier filter.

5. The kit of claim 4, wherein the barrier filter is porous.

6. The kit of claim 4, wherein the barrier filter is a nylon mesh barrier.

7. The kit of claim 1, wherein the detection zone comprises an SP22 antibody.

8. The kit of claim 7, wherein the SP22 antibody is conjugated to a detectable marker.

9. The kit of claim 8, wherein the detectable marker is chemiluminescent.

10. The kit of claim 1, further comprising one or more ports for adding solution directly to the detection zone.

11. The kit of claim 1, further comprising instructions for using the kit to detect the presence of SP22.

12. The kit of claim 1, wherein the detection zone contains a subset of sperm having an average motility higher than an average motility of sperm of the sample.

* * * * *